US008188116B2

(12) United States Patent
Bornhop et al.

(10) Patent No.: US 8,188,116 B2
(45) Date of Patent: *May 29, 2012

(54) AGENTS FOR THERAPY EFFICACY MONITORING AND DEEP TISSUE IMAGING

(75) Inventors: Darryl J. Bornhop, Nashville, TN (US); H. Charles Manning, Nashville, TN (US); Mingfeng Bai, St. Louis, MO (US); Shelby K. Wyatt, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 1142 days.

This patent is subject to a terminal disclaimer.

(21) Appl. No.: 11/777,752

(22) Filed: Jul. 13, 2007

(65) Prior Publication Data

US 2008/0031823 A1 Feb. 7, 2008

Related U.S. Application Data

(63) Continuation-in-part of application No. 11/149,602, filed on Jun. 10, 2005, now Pat. No. 7,754,884, which is a continuation-in-part of application No. 10/233,672, filed on Sep. 4, 2002, now Pat. No. 7,338,651.

(60) Provisional application No. 60/868,697, filed on Dec. 5, 2006.

(51) Int. Cl.
*C07D 209/56* (2006.01)
*A61K 31/47* (2006.01)

(52) U.S. Cl. .................. 514/307; 514/172; 514/252.06; 514/411; 514/616; 540/501; 544/234; 546/144; 548/427; 564/192

(58) Field of Classification Search ........................ None
See application file for complete search history.

(56) References Cited

U.S. PATENT DOCUMENTS

| | | | |
|---|---|---|---|
| 5,091,381 | A | 2/1992 | Kim et al. |
| 5,268,486 | A | 12/1993 | Waggner et al. |
| 5,928,627 | A | 7/1999 | Kiefer et al. |
| 6,027,709 | A | 2/2000 | Little et al. |
| 6,379,649 | B1 | 4/2002 | Katsifies et al. |
| 7,338,651 | B2 | 3/2008 | Bornhop et al. |
| 7,754,884 | B2 * | 7/2010 | Bornhop et al. ............ 546/146 |
| 2003/0129579 | A1 | 7/2003 | Bornhop et al. |
| 2003/0130575 | A1 | 7/2003 | Desai |
| 2003/0152518 | A1 | 8/2003 | Tidmarsh et al. |
| 2004/0266746 | A1 | 12/2004 | Rosen et al. |
| 2008/0031823 | A1 | 2/2008 | Bornhop et al. |
| 2008/0241074 | A1 | 10/2008 | Bornhop et al. |
| 2008/0241873 | A1 | 10/2008 | Bornhop et al. |
| 2009/0105128 | A1 | 4/2009 | Bornhop et al. |
| 2010/0278739 | A1 | 11/2010 | Bornhop et al. |
| 2010/0324130 | A1 | 12/2010 | Bornhop et al. |

FOREIGN PATENT DOCUMENTS

| | | |
|---|---|---|
| AU | 2002323528 | 3/2008 |
| CA | 2459724 | 2/2011 |
| EP | 1429783 | 6/2004 |
| EP | 1841466 | 10/2007 |
| WO | WO03020701 | 3/2003 |
| WO | WO2006074129 | 7/2006 |

OTHER PUBLICATIONS

Ahmad, et al.; Major liver resection in the elderly; ASGBI: Br. J. Surg. vol. 89, Suppl. 1; Jun. 2002; pp. 62-64.
Alho, et al.; Expression of Mitochondrial Benzodiazepine Receptor and Its Putative Endogenous Ligand in Cultured Primary Astrocytes and C-6 Cells—Relation to Cell-Growth. Cell Growth & Differentiation 1994;5:1005-1014.
Benavides, et al. Imaging of Human-Brain Lesions with an Omega-3 Site Radioligand. Annals of Neurology 1988;24:708-712.
Black, et al.; Imaging of Brain-Tumors Using Peripheral Benzodiazepine Receptor Ligands. Journal of Neurosurgery 1989;71:113-118.
Broaddus, et al.; Department of Neurosurgery UoVHSCC. Peripheral-type benzodiazepine receptors in human glioblastomas: pharmacologic characterization and photoaffinity labeling of ligand recognition site. Brain research. 1990;518(1-2):199-208.
Bromiley, et al. Attenuation correction in PET using consistency conditions and a three-dimensional template. Ieee Transactions on Nuclear Science 2001;48:1371-1377.
Casellas, et al.; Peripheral benzodiazepine receptors and mitochondrial function. Neurochemistry International 2002;40:475-486.
Cornu, et al.; Increase in Omega-3 (Peripheral-Type Benzodiazepine) Binding-Site Densities in Different Types of Human Brain-Tumors—a Quantitative Autoradiography Study. Acta Neurochirurgica 1992;119:146-152.
Czernin, et al.; *Annu Rev Med* 2002, 53, 89-112.
Dehdashti, et al.; Positron emission tomographic assessment of "metabolic flare" to predict response of metastatic breast cancer to antiestrogen therapy. European Journal of Nuclear Medicine 1999;26:51-56.
Diorio, et al.; Peripheral Benzodiazepine Binding-Sites in Alzheimers-Disease Frontal and Temporal Cortex. Neurobiology of Aging 1991;12:255-258.
Ernst, et al., Cytometry 10:3-10 (1989). Faulkner, et al.; Lanthanide-sensitized lanthanide luminescence: Terbium-sensitized ytterbium luminescence in a trinuclear complex. Journal of the American Chemical Society 2003;125: 10526-10527.
Fennell, et al.; Bcl-2 resistant mitochondrial toxicity mediated by the isoquinoline carboxamide PK11195 involves de novo generation of reactive oxygen species. British Journal of Cancer 2001;84:1397-1404.
Francis et al. *Eur J Nucl Med Mol Imaging* 2003, 30, 988-994.
Gaietta, et al. Multicolor and electron microscopic imaging of connexin trafficking. Science 2002;296:503-507.
Gonzalez-Polo, et al.; PK11195 potently sensitizes to apoptosis induction independently from the peripheral benzodiazepine receptor; Oncogene 2005; 24; 7503-7513.

(Continued)

*Primary Examiner* — Zinna Northington Davis
(74) *Attorney, Agent, or Firm* — Stites & Harbison PLLC; Richard S. Myers, Jr.

(57) ABSTRACT

Compounds and methods related to NIR molecular imaging, in-vitro and in-vivo functional imaging, therapy/efficacy monitoring, and cancer and metastatic activity imaging. Compounds and methods demonstrated pertain to the field of peripheral benzodiazepine receptor imaging, metabolic imaging, cellular respiration imaging, cellular proliferation imaging as targeted agents that incorporate signaling agents.

16 Claims, 8 Drawing Sheets

OTHER PUBLICATIONS

Griffin, et al.; Simple, high yielding synthesis of trifunctional fluorescent lanthanide chelates. Tetrahedron Letters 2001;42:3823-3825.

Hardwick, et al.; Peripheral-type benzodiazepine receptor (PBR) in human breast cancer: Correlation of breast cancer cell aggressive phenotype with PBR expression, nuclear localization, and PBR-mediated cell proliferation and nuclear transport of cholesterol. Cancer Research 1999;59:831-842.

Hawrysz, et al.; Developments toward diagnostic breast cancer imaging using near-infrared optical measurements and fluorescent contrast agents. Neoplasia 2000;2:388-417.

Jakubikova, et al.; PK11195, an isoquinoline carboxamide ligand of the mitochondrial benzodiazepine receptor, increased drug uptake and facilitated drug-induced apoptosis in human multidrug-resistant leukemia cells in vitro. Neoplasma 2002;49:231-236.

Kozikowski; et al. Papadopoulos V. Synthesis and Biology of a 7-Nitro-2,1,3-benzoxadiazol-4-yl Derivative of 2-Phenylindole-3-acetamide: A Fluorescent Probe for the Peripheral-Type Benzodiazepine Receptor. Journal of Medicinal Chemistry 1997;40:2435-2439.

Lemieux, et al.; Exploiting differences in sialoside expression for selective targeting of MRI contrast reagents. Journal of the American Chemical Society 1999;121:4278-4279.

Licha, et al.; Hydrophilic cyanine dyes as contrast agents for near-infrared tumor imaging: Synthesis, photophysical properties and spectroscopic in vivo characterization. Photochemistry and Photobiology 2000;72:392-398.

Louie, et al. In vivo visualization of gene expression using magnetic resonance imaging. Nature Biotechnology 2000;18:321-325.

Maaser, et al. Specific ligands of the peripheral benzodiazepine receptor induce apoptosis and cell cycle arrest in human colorectal cancer cells. British journal of cancer. 2001;85(11):1771-80.

Manning, et al. Facile, efficient conjugation of a trifunctional lanthanide chelate to a peripheral benzodiazepine receptor ligand. Organic Letters 2002;4:1075-1078.

Manning, et al. Targeted Molecular Imaging Agent for Cellular-Scale Bi-modal Imaging. Bioconjugate Chemistry 2004, 15, 1488-1495.

Medina, et al.;. Biol Res 2002, 35, 9-26.

Messmer, et al. Increased peripheral benzodiazepine binding sites in the brain of patients with Huntington's disease. Neuroscience Letters 1998;241:53-56.

Narayanan, et al.; J. Org. Chem. 60:2391-5 (1995).

Ntziachristos, et al.; Probing physiology and molecular function using optical imaging: applications to breast cancer. Breast Cancer Research 2001;3:41-46.

Okaro, et al.; PK11195 a mitochondrial benzodiazepine receptor antagonist, reduces apoptosis threshold in Bcl-Xl and Mcl-1 expressing human cholangiocarcinoma cells. Gut 2002;51:556-561.

Okaro, et al. ; Pk11195, a mitochondrial benzodiazepine receptor antagonist, reduces apoptosis threshold in Bcl-X-L and Mcl-1 expressing human cholangiocarcinoma cells. Gut 2002;51:556-561.

Oyama, et al. MicroPET assessment of androgenic control of glucose and acetate uptake in the rat prostate and a prostate cancer tumor model. Nuclear Medicine and Biology 2002;29:783-790.

Oyama, et al. C-11-acetate PET imaging of prostate cancer: Detection of recurrent disease at PSA relapse. Journal of Nuclear Medicine 2003;44:549-555.

Papadopoulos V. Peripheral-Type Benzodiazepine Diazepam Binding Inhibitor Receptor—Biological Role in Steroidogenic Cell-Function. Endocrine Reviews 1993;14:222-240.

Shavaleev, et al. Bell ZR, Faulkner S, Ward MD. Visible-light sensitisation of near-infrared luminescence from Yb(III), Nd(III) and Er(III) complexes of 3,6-bis(2-pyridyl)tetrazine. Dalton Transactions 2003:808-814.

Starosta-Rubinstein, et al.; Imaging of a glioma using peripheral benzodiazepine receptor ligands. proceedings of the national academy of sciences of the United States of America 1987;84:891-5.

Sutter, et al.; Specific ligands of the peripheral benzodiazepine receptor induce apoptosis and cell cycle arrest in human esophageal cancer cells. International journal of cancer. Journal international du cancer. 2002;102(4):318-27.

Vejdelek, et al.; Synthesis of 7-Chloro-5-(4-Chlorophenyl)-1-Methyl-1,3-Dihydro-1,4-Benzodiazepin-2-One. Collection of Czechoslovak Chemical Communications 1985;50:1064-1069.

Vowinckel, et al. PK11195 binding to the peripheral benzodiazepine receptor as a marker of microglia activation in multiple sclerosis and experimental autoimmune encephalomyelitis. Journal of Neuroscience Research 1997;50:345-353.

Walker, et al.,; PK11195, a peripheral benzodiazepine receptor (pBR) ligand, broadly blocks drug efflux to chemosensitize leukemia and myeloma cells by a pBR-independent, direct transporter-modulating mechanism; Blood 2005; 106:10; 3584-3593.

Weissleder, et al.; Molecular imaging. Radiology 2001;219:316-333.

Werts, et al. Fluorescein and eosin as sensitizing chromophores in near-infrared luminescent ytterbium(III), neodymium(III) and erbium(III) chelates. Chemical Physics Letters 1997;276:196-201.

Werts, et al., Efficient visible light sensitisation of water-soluble near-infrared luminescent lanthanide complexes. Journal of the Chemical Society-Perkin Transactions 2 2000:433-439.

Wolfe, et al. In vivo imaging of human colon cancer xenografts in immunodeficient mice using a guanylyl cyclase C-specific ligand. Journal of Nuclear Medicine 2002;43:392-399.

Zhang, et al. Pyropheophorbide 2-deoxyglucosamide: A new photosensitizer targeting glucose transporters. Bioconjugate Chemistry 2003;14:709-714.

Zhang, et al. [F-18]FMDAA1106 and [F-18]FED106: Two position-emitter labeled ligands for peripheral benzodiazepine receptor (PBR). Bioorganic & Medicinal Chemistry Letters 2003;13:201-204.

* cited by examiner (A) white light picture of dosed cells; (B) fluorescence picture of dosed cells;
(C) white light picture of un-dosed cells; (D) fluorescence picture of un-dosed cells Figure 3.8 (A) white light picture of dosed cells; (B) fluorescence picture of dosed cells; (C) white light picture of un-dosed cells; (D) fluorescence picture of un-dosed cells control	Smad3KO Day 6 disease
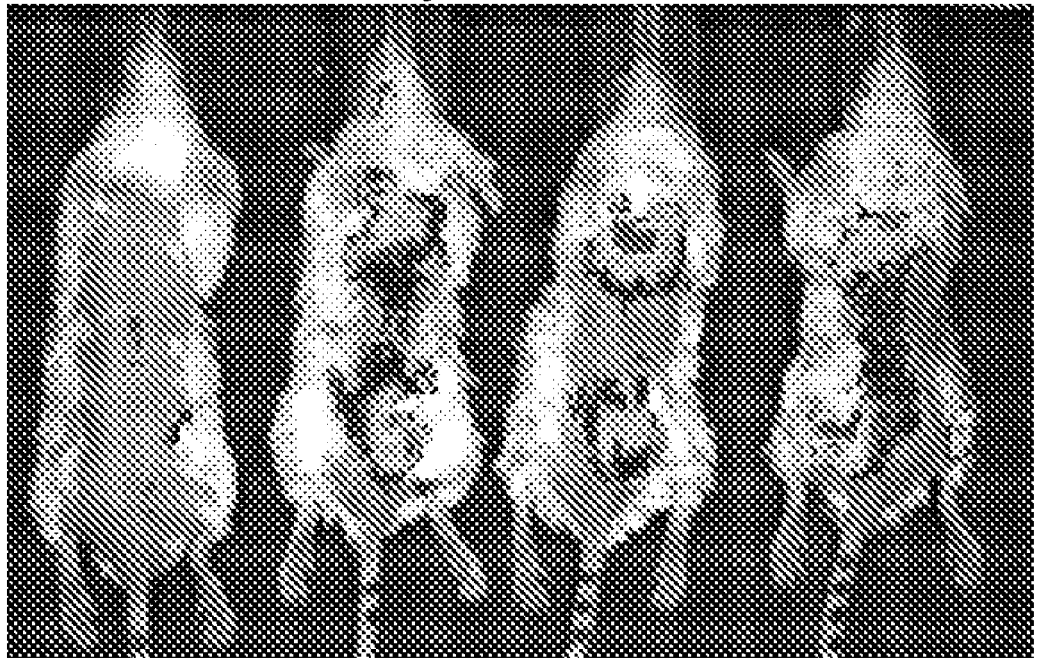
Control  EAE  EAE/treated  EAE
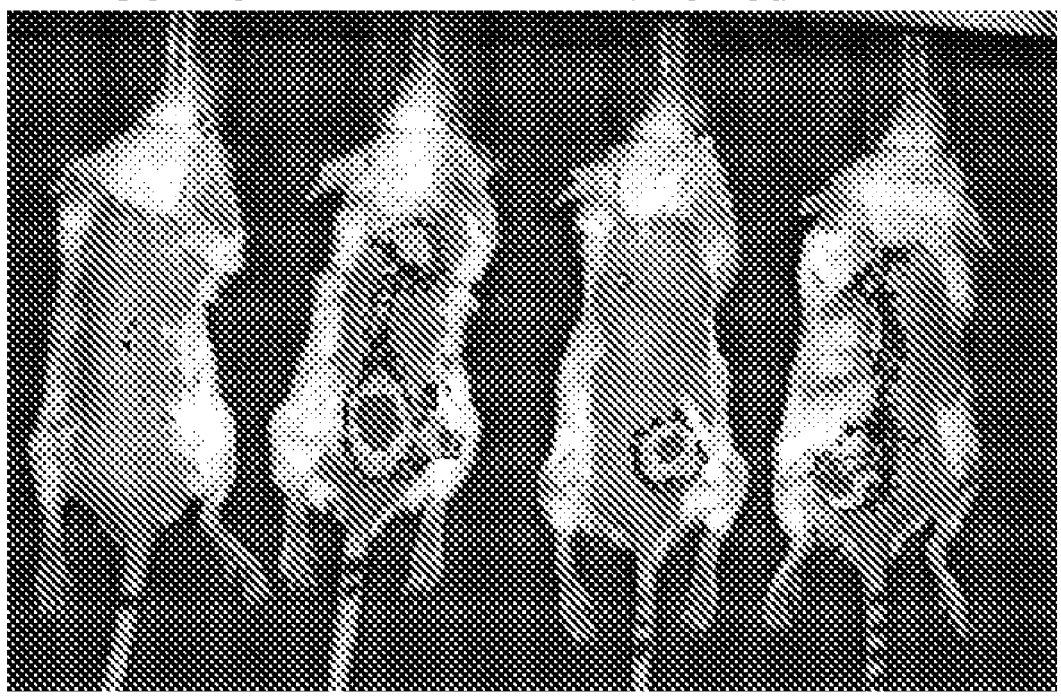
Day 12 disease
*FIG. 4*

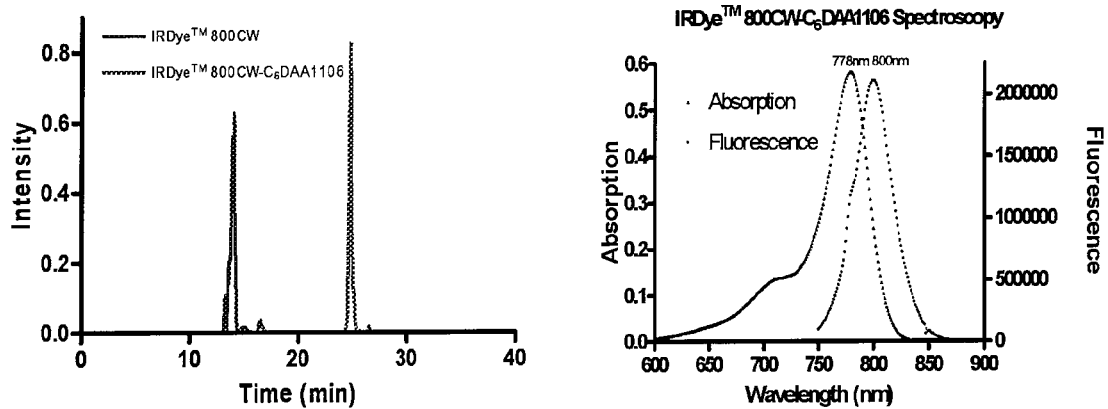
Figure 5 Left: HPLC chromatograph of IRDye™ 800CW and NIRDAA at 780 nm; Right: Absorption and emission spectra of NIRDAA in methanol
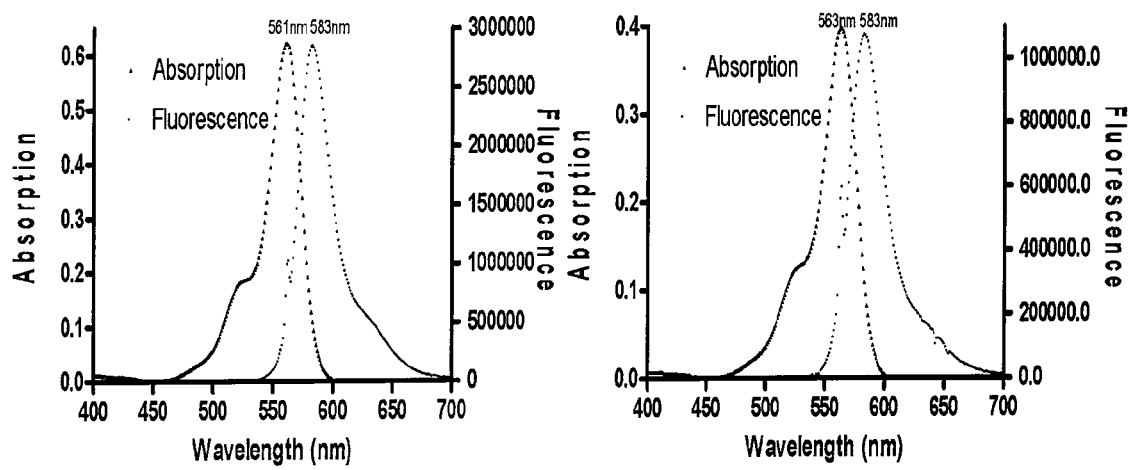
Figure 6 Lissamine-$C_6$DAA1106 isomer I (left) and isomer II (right) absorption and fluorescence curves.

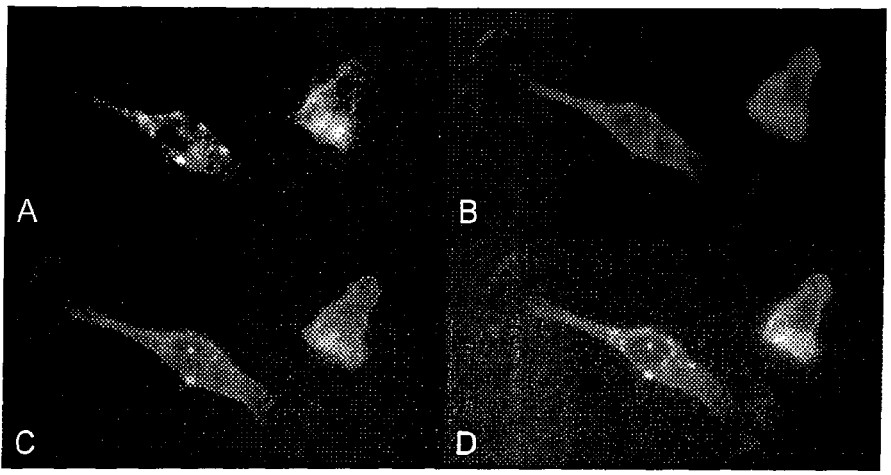
Figure 7 MDA-MB-231 cells fluorescence images. White (blue in overlaid picture) (A): 1 µM NIRDAA; Red (B): 1 µM LissDAA; Green (C): 1 nM Mitotracker; Mixed colors (D): overlaid picture of A, B and C.
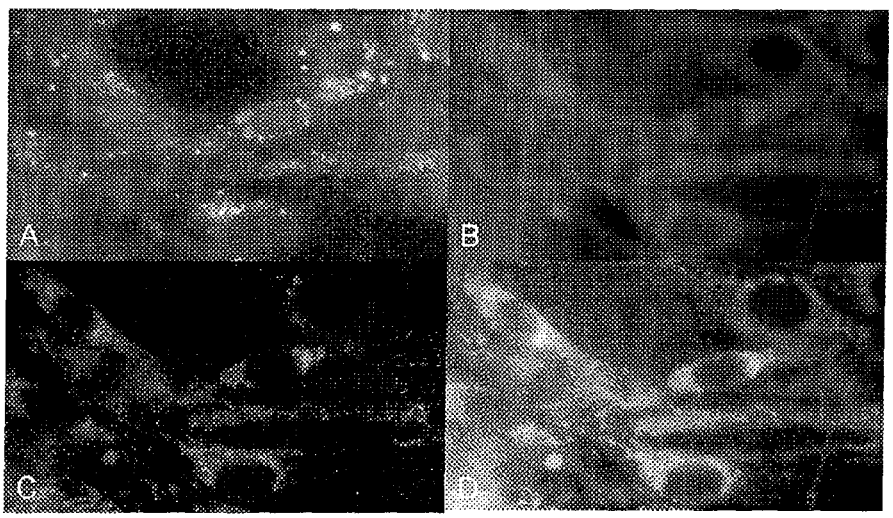
Figure 8 C6 cells fluorescence images. White (blue in overlaid picture) (A): 1 µM NIRDAA; Red (B): 1 µM LissDAA; Green (C): 1 nM Mitotracker; Mixed colors (D): overlaid picture of A, B and C.

Table 2. Lissamine-DAA1106 absorption and fluorescenceAbsorption $\lambda_{max}$=561 nm and fluorescence $\lambda_{max}$=579 nm

AGENTS FOR THERAPY EFFICACY MONITORING AND DEEP TISSUE IMAGING

PRIORITY INFORMATION

This application is a continuation-in-part of application Ser. No. 11/149,602 filed Jun. 10, 2005, U.S. Pat. No. 7,754,884, issued Jul. 13, 2010, which is a continuation-in-part of application Ser. No. 10/233,672 filed Sep. 4, 2002, U.S. Pat. No. 7,338,651, issued Mar. 4, 2008. This application also claims benefit of U.S. Patent Application No. 60/868,697, filed Dec. 5, 2006.

The contents of these applications are incorporated herein by reference.

GOVERNMENT SUPPORT

This invention was made with Government support under Department of Defense Grant number W81XWH-04-1-0432. The Government has certain rights in this invention.

FIELD OF THE INVENTION

This invention relates generally to the field of molecular imaging, and more specifically to the field of functional imaging, including glucose transporters, thymidine kinase activity, and peripheral benzodiazepine receptors as targeted agents that incorporate near-infrared fluorophores as signaling agents.

Additionally, this invention relates generally to the field of targeted drug delivery, including in the areas of cancer treatment.

BACKGROUND OF THE INVENTION

Current state-of-the-art detection and surgical resection tools used in cancer treatment are insufficient. Early stage disease can be missed, resection can be incomplete and these two factors alone are major contributors to morbidity and mortality. Outcomes are intrinsically linked to disease detection and treatment efficacy. Therefore, improvement in the detection of early cellular changes, as well as enhanced visualization of diseased tissue, is of paramount importance.

Optical methods continue to provide a powerful means for studying cell and tissue function. Recent discoveries in Molecular Imaging (MI) are certain to play a vital role in the early detection, diagnosis, and treatment of disease. MI will also aid in the study of biological and biochemical mechanisms, immunology, and neuroscience. MI agents commonly consist of a signaling moiety (fluorophore, radioisotope or $Gd^{3+}$ ion) and a targeting functionality such as an antibody or peptide, sugar or a peripheral benzodiazepine receptor (PBR) ligand. NIR molecular imaging agents are particularly attractive due to the inherently low water and tissue absorption in the NIR spectral region. Additionally, the low scattering cross-section and lack of autofluorescence background in the near infrared (NIR) region facilitate deep penetration and high-resolution images from small interrogated volumes.

While glandular and secretory tissues are normally rich in PBR, other quiescent tissue ordinarily express PBR at relatively low levels. Primarily spanning the bi-layered mitochondrial membrane, the PBR is expressed almost ubiquitously and thought to be associated with many biological functions including the regulation of cellular proliferation, immunomodulation, porphyrin transport, heme biosynthesis, anion transport, regulation of steroidogenesis and apoptosis. Given the importance of PBR toward regulating mitochondrial function, it is not surprising that PBR density changes have been observed in acute and chronic neurodegenerative states in humans, as well as numerous forms of cancer. For example, temporal cortex obtained from Alzheimer's patients showed an increase in PBR, and correlations with Huntington's disease, multiple sclerosis and gliosis have been demonstrated. Breast cancer generally demonstrates increased PBR expression and represents another potentially attractive target, especially in the NIR. The development of high affinity ligands for PBR (such as, for example, PK-11195, Ro5-4864, DAA1106, and DAA1107) has made non-invasive imaging modalities more suitable.

Other functional imaging targets include the glucose transporter and thymidine kinase 1. By targeting the glucose transporter, $[^{18}F]$-fluoro-deoxyglucose (FDG) has been successfully employed as a positron emission tomography (PET) agent to determine the metabolic statues (cellular respiration) of suspect tissues. Modest functionalization of glucose at the C-2 position does not hinder sugar uptake but does prevent cellular metabolism, therefore glucose agents can accumulate intracellularly. Since tumor cells metabolize glucose a higher rate than normal cells, the accumulation of glucose mimics (i.e. FDG and similar agents) can facilitate discrimination of tissues based on their metabolic status. While FDG imaging certainly has demonstrated utility to the clinical oncologist, the requirement of a cyclotron and a PET scanner somewhat limit its use.

Recently, in effort to improve the specificity of functional imaging agents like FDG, new probes for cellular proliferation imaging have been developed. Targeting the enzyme thymidine kinase 1 (TK1), an enzyme responsible for DNA replication, $[^{18}F]3'$-deoxy-3'fluorothymidine (FLT) has been shown to be an attractive complement to FDG imaging. Similar to FDG, FLT is not fully metabolized by cells and accumulates in target tissues, making it a promising imaging agent for rapidly proliferating tissues. When used in combination with FDG, clinical imaging of diseased tissue has the ability to be highly sensitive and specific.

It has been shown that NIR emitting Ln-Chelates can be prepared opening the avenue to complexes with spectral properties more compatible with biological imaging such as visible absorption, NIR emission and microsecond-long emission lifetimes. These complexes have high molar absorptivity and have luminescent lifetimes in the microsecond regime allowing temporal rejection of noise.

The present inventors have demonstrated the synthesis and utility of Eu-PK11195 and Gd-PK11195. Others have prepared PK11195 as a PET agent for use in humans. A NIR Pyropheophorbide agent has been reported for imaging glucose transporters, however this agent was not spectroscopically optimized for deep tissue in-vivo imaging (ex. 679 nm, em. 720 nm). At present, the authors are unaware of any NIR imaging agents based on thymidine imaging.

Additionally, the Peripheral Benzodiazepine Receptor (PBR), an 18 kDa mitochondrial protein, has become an attractive target for cancer imaging and treatment.

Over-expression of PBR has been observed in a variety of cancers, including brain, breast, colorectal, prostate and ovary cancers, Hepatocellular carcinoma, astrocytomas and endometrial carcinoma. PBR is associated with a number of biological processes, such as cell proliferation, apoptosis, steroidogenesis, and immunomodulation, however, its exact physiological role is still not clear.

SUMMARY OF THE INVENTION

The peripheral benzodiazepine receptor (PBR) has been shown an attractive target for contrast-enhanced imaging of disease. See Publication No. 2003/0129579, incorporated herein by reference. Embodiments of the present invention include PBR targeted agents which incorporate near-infrared (NIR) fluorophores as signaling agents. Aspects of the present invention include a previously unknown class of NIR absorbing/emitting PBR targeted contrast agents which utilize a conjugable form of PK11195 as a targeting moiety.

Additionally, aspects of the present invention include the synthesis of NIR—metabolic and proliferation probes. The authors report a saccharide agent suitable for metabolic imaging in similar fashion to $^{18}$FDG and a NIR-thymidine probe suitable for imaging cellular proliferation (DNA synthesis). The NIR contrast agents disclosed herein are suitable for optical imaging using spectral and time-gated detection approaches to maximize the signal-to-background ratio. High molar extinction dyes that absorb and emit in the NIR, such as IRdye800CW™ (available from LiCOR) and CY7 (Amersham), as well as NIR Lanthanide chelates are demonstrated. Since thymidine, PK11195 and other PBR ligands have been suggested as therapeutic agents, the molecules demonstrated here could also be useful therapeutics which also offers direct monitoring of dose delivery and therapeutic efficacy.

With absorption and emission closer to the tissue transparency window (780 nm, 830 nm respectively), the dyes reported here are much more suited for in-vivo imaging. Additionally, no one has demonstrated NIR PBR ligands for imaging PBR expression and/or therapy.

Thus, one aspect of the present invention is a method of imaging a molecular event in a sample, the method steps comprising administering to the sample a probe having an affinity for a target. The probe has at least one of a ligand/signaling agent combination, or conjugable form of a ligand/signaling agent combination. After the probe is administered, a signal from the probe may be detected. In embodiments of the present invention, the sample can be at least one of cells, tissue, cellular tissue, serum, cell extract, bodily fluids. The bodily fluids may be, for example, breast milk, sputum, vaginal fluids, urine.

Another aspect of the present invention is a method of measuring glucose uptake. This embodiment comprises the steps of administering to a sample a conjugate, the conjugate comprising a conjugable glucosamine compound and a signaling agent; and then detecting a signal from said conjugate. In embodiments of the present invention, the sample is at least one of cells, tissue, cellular tissue, serum, cell extract, bodily fluids.

Another aspect of the present invention is a method of quantifying the progression of a disease state progression that includes the steps of (a) administering to a first sample a conjugate that comprises a conjugable deoxythymidine compound and a signaling agent; (b) detecting a signal from the conjugate; (c) after a period of time from step (b), administering to a second sample a conjugate, (d) detecting a second signal; and (e) comparing the first signal with the second signal to determine the progress of a disease state. Again examples of the sample are at least one of cells, tissue, cellular tissue, serum, cell extract, bodily fluids.

Another aspect of the present invention is the above method, where the conjugate includes a peripheral benzodiazepine affinity ligand or conjugable form thereof and a signaling agent.

Another aspect of the present invention is the above method, where the conjugate includes a glucosamine compound and a signaling agent.

In the above embodiments and other embodiments of the present invention, the administration step is in vivo or in vitro.

A further aspect of the present invention is conjugable DAA1106 compounds.

Another aspect of the present invention is a novel conjugate comprising a conjugable DAA1106 compound.

Another aspect of the present invention is imaging a molecular event comprising administering a conjugate of the present invention.

Another aspect of the present invention is a method of treating cancer comprising administering a conjugate of the present invention.

Another aspect of the present invention is a method of synthesizing receptor or protein targeted agents for selective cancer therapy. The methods of the present invention are designed to be applicable to the application of targeted delivery of any conjugable moiety (therapeutic, imaging or combination). Preparation of small molecule ligand that can be coupled to a drug, would allow the drug be selectively delivered and internalized into cells substantially improving cell killing and clinical efficacy.

In embodiments of the present invention, conjugable DAA1106 is the Peripheral Benzodiazepine Receptor (PBR) ligand Etoposide is one of the most widely used anticancer drugs and is active against small-cell lung cancers, leukemias, and lymphomas.

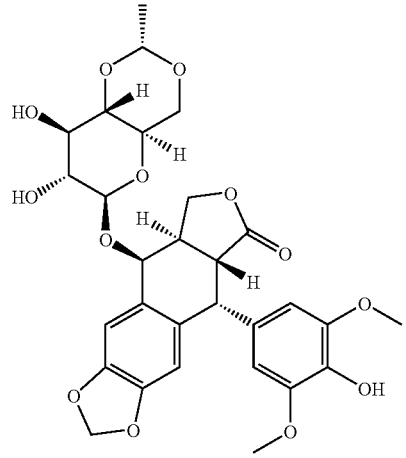

Etoposide compound

However, the application of etoposide in cancer therapy is limited by the lack of selectivity. PBR is a mitochondrial protein and highly expressed in leukemia and lymphoma cells. DAA1106 is a relatively new PBR ligand with fentomolar ($10^{-15}$M) binding affinity for PBR. An embodiment of the present invention is coupling etoposide and other cancer therapeutics to DAA1106, and the resulting molecules can provide selective cancer therapy.

A conjugable form of DAA1106 with a carbon spacer (CnDAA1106, n=3-9) was therefore synthesized and used to conjugate etoposide. The compound $C_n$DAA1106 is another embodiment of the present invention.

The present inventors have synthesized a functionalized PBR ligand, $C_n$DAA1106, which can be conjugated to a variety of signaling moieties and widely applied in PBR targeted cancer imaging and targeted drug delivery. In addition, these DAA1106 analogs of the present invention have been labeled with two fluorescent dyes and the resulting imaging probes, NIRDAA and LissDAA display nanomolar binding affinities to PBR and have been successfully imaged in vitro.

BRIEF DESCRIPTION OF THE DRAWINGS

FIG. 4 is a photograph that shows in vivo neurodegenerative imaging of a small laboratory animal.

FIG. 5 is a chromatograph for NIR dye and NIRDAA at 780 nm.

FIG. 6 shows spectroscopy curves for LissDAA of the present invention.

FIGS. 7 and 8 are fluorescence microscopy images showing cell uptake of NIRDAA and LissDAA.

DESCRIPTION OF THE INVENTION

Figure 1:
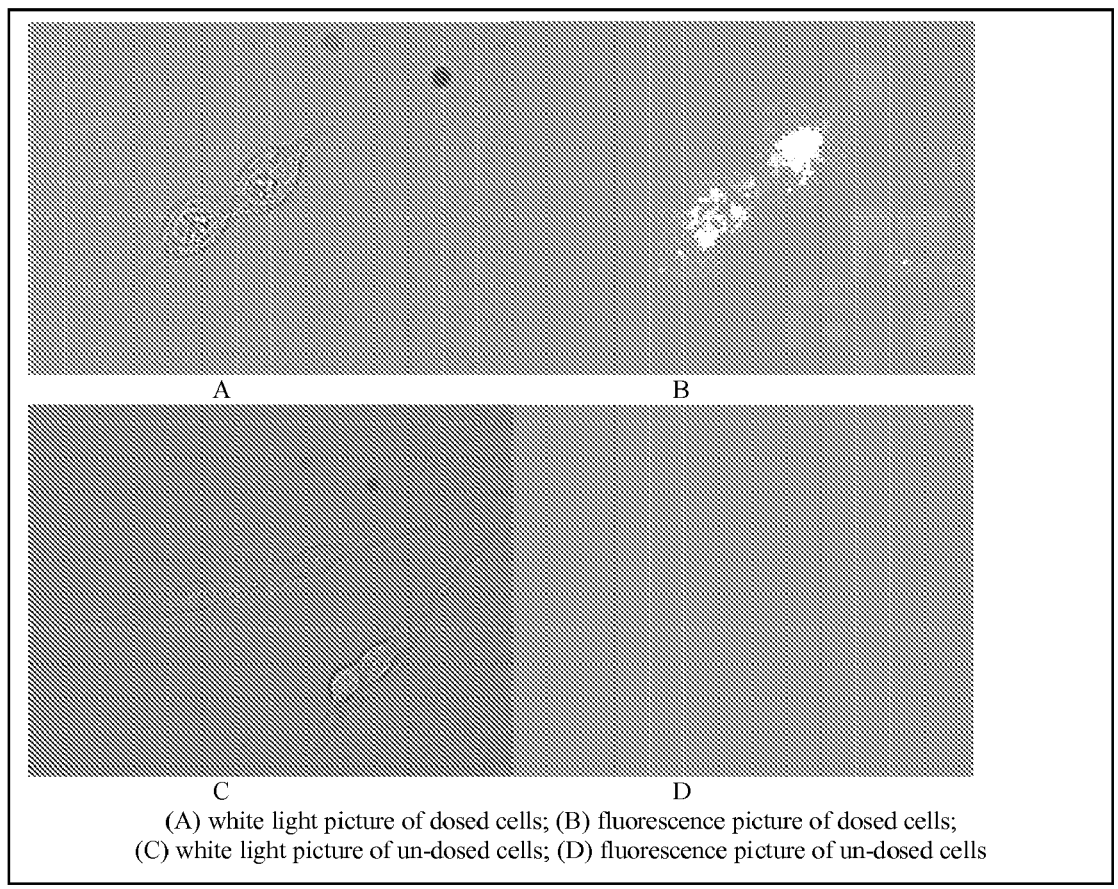
FIG. 1 is a photograph that shows white light and fluorescence pictures of dosed cells and un-dosed cells in accordance with the present invention, and is further discussed in Example 6, below. Picture A is a white light picture of dosed cells, Picture B is a fluorescence picture of dosed cells, Picture C is a white light picture of un-dosed cells, and Picture D is a fluorescence picture of un-dosed cells.

Embodiments of the present invention include NIR agents for the PBR based on NIR dyes, including Lanthanide chelates. Additionally, complimentary imaging agents are disclosed using a novel NIR saccharide and NIR thymidine agent. Aspects of the present invention include both being used separately, as well as where the agents are used together as a cocktail whereby both PBR expression and metabolic and or cellular proliferation status could be simultaneously monitored in-vivo.

PBR ligands such as PK11195 have been suggested as therapeutic agents. Mitochondria localized anti-death proteins of the Bcl-2 family play a central role in inhibiting apoptosis and therefore present therapeutic targets. PBR shares a close physical association with the permeability transition pore complex (PTPC) and binding of PK11195 has been shown to cause Bcl-2 resistant generation of oxidative stress. The agents reported here are unique in that they facilitate in-vivo monitoring of therapeutic delivery and efficacy.

As stated above, aspects of the present invention include methods of imaging a molecular event. in a sample, the method steps comprising administering to the sample a probe having an affinity for a target. The probe has at least one of a ligand/signaling agent combination, or conjugable form of a ligand/signaling agent combination. One such ligand/signaling agent combination comprises PBR ligands, or conjugable forms thereof.

Examples of the PBR ligands of the present invention include conjugable forms, or conjugable analogs of the following compounds:

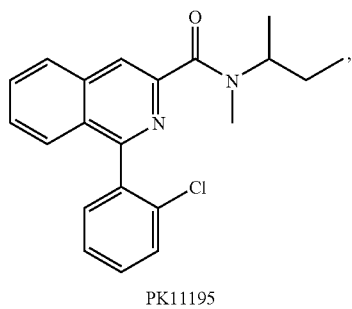

PK11195

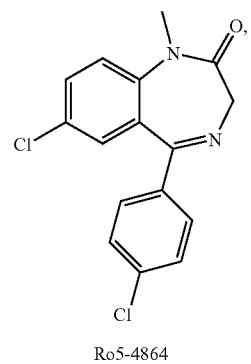

Ro5-4864

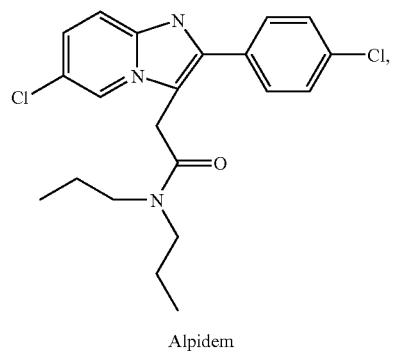

Alpidem

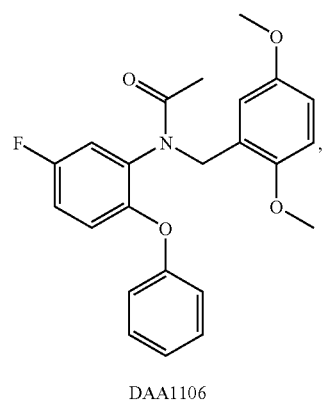

DAA1106

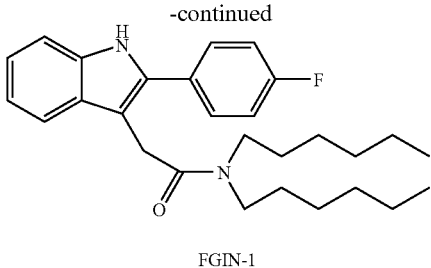

FGIN-1

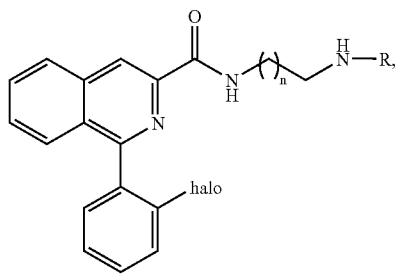

wherein R is H or alkyl, n is 0-10, and "halo" is fluorine, chlorine, bromine, iodine. In other embodiments of the present invention, halo is chlorine.

The term "halo" or "halogen," as used herein, includes radio isotopes of halogen compounds, such as $I^{121}$ and $F^{19}$.

Additionally, for exemplary purposes, conjugable forms of Ro5-4864 include the following and/or analogs or derivatives thereof:

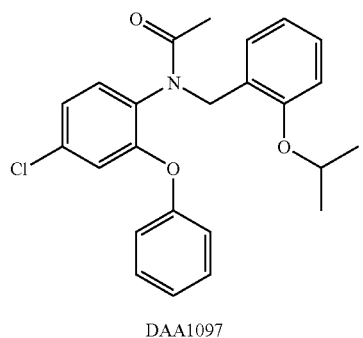

DAA1097

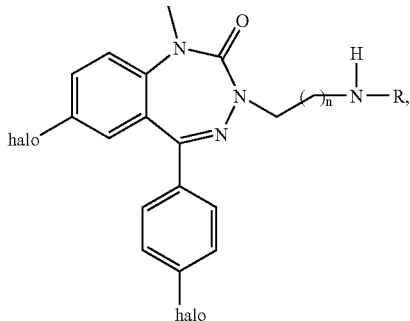

wherein the variables are defined above. In other embodiments of the present invention, halo is chlorine.

Additionally, for exemplary purposes, conjugable forms of DAA1106 include the following and/or analogs or derivatives thereof:

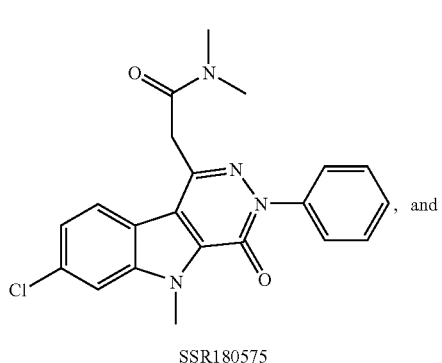

SSR180575, and

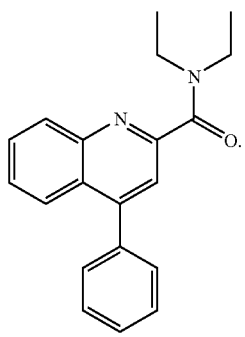

For the purposes of the present invention, the term analog encompases isomers, homologs, or other compounds sufficiently resembling the base compound in terms of structure and do not destroy activity. "Conjugable forms," "conjugable compounds," and similar terms describe a form of the compound that can readily form a covalent form a covalent bond with a signaling agent such as an IR dye.

For exemplary purposes, conjugable forms of PK11195, above, include at least the following compounds, and/or analogs or derivatives thereof:

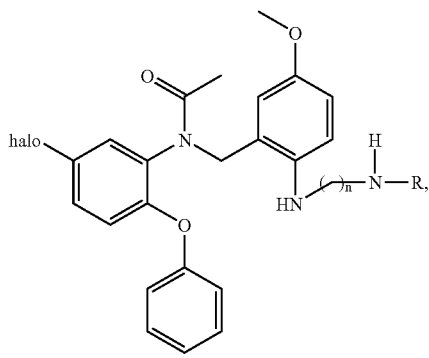

wherein the variables are defined above, and:

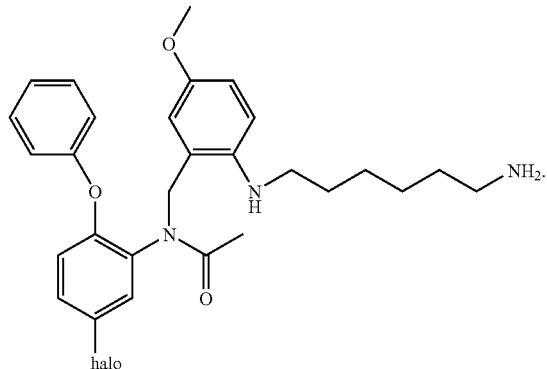

In other embodiments of the present invention, halo is chlorine or fluorine.

Additionally, for exemplary purposes, conjugable forms of SSR180575 include the following and/or analogs or derivatives thereof:

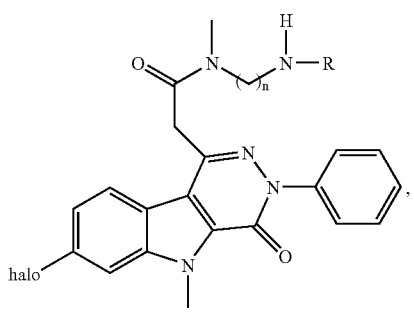

wherein the variables are defined above. In other embodiments of the present invention, halo is chlorine.

Non-limited examples of PBR ligands and signaling moieties include the following compounds:

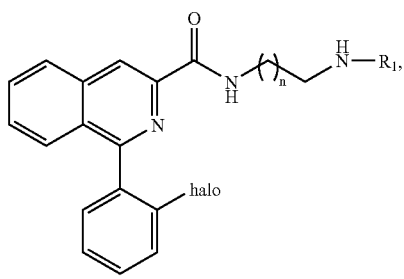

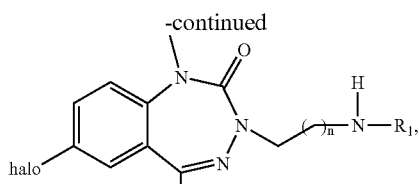

-continued

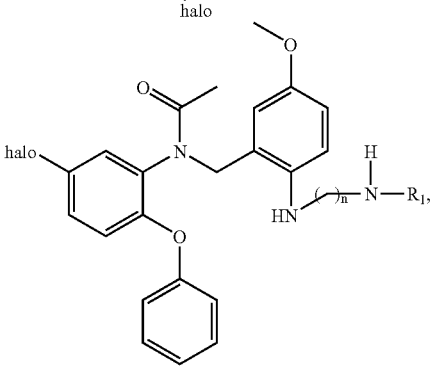

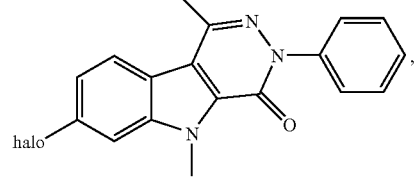

or an analog thereof, wherein $R_1$ is a signaling moiety or a therapeutic drug; "halo" is fluorine, chlorine, bromine, iodine; and n is 0-10.

In embodiments of the present invention, the signaling moiety is a dye, such as a cyanine dye. Additionally, in embodiment, the drug is Etoposide.

Additionally, other aspects of the present invention include NIR-saccharide agents suitable for metabolic imaging in similar fashion to $^{18}$FDG. Given the ubiquitous clinical use of $^{18}$FDG, 2-deoxyglucose derivatives have been extensively biologically characterized. See Czernin, J.; Phelps, M. E. *Annu Rev Med* 2002, 53, 89-112. These derivatives are useful metabolic imaging agents given the overexpression of glucose transporters and increased hexokinase activity in tumors. See Medina, R. A.; Owen, G. I. *Biol Res* 2002, 35, 9-26. 2-deoxyglucose imaging agents are incorporated into cells via the glucose transporter and are subsequently phosphorylated by hexokinase. In phosphorylating the probe, the neutral molecule becomes anionic and membrane impermeable. Functionalization at the 2-position prevents further metabolism, and thus the probe is trapped in the cells, with further uptake leading to significant accumulation. See Zhang, M.; Zhang, Z. H.; Blessington, D.; Li, H.; Busch, T. M.; Madrak, V.; Miles, J.; Chance, B.; Glickson, J. D.; Zheng, G. *Bioconjugate Chem* 2003, 14, 709-714.

Additionally, other aspects of the present invention include a NIR-thymidine probe for monitoring cellular proliferation, similar in fashion to [$^{18}$F]3'-deoxy-3'fluorothymidine (FLT). FLT has been used clinically and extensively compared to FDG. See Halter et al. *General Thoracic Surgery* 2004, 127, 1093-1099 and Francis et al. *Eur J Nucl Med Mol Imaging* 2003, 30, 988-994. In proliferating cells, FLT metabolism takes place within the anabolic arm of the DNA salvage pathway. TK1 controls entry into the salvage pathway and converts FLT to the mono-phosphate species. The agent is further phosphorylated, but can not be incorporated into DNA due to its lack of a hydroxyl group at 3'.

With respect to the signaling agents used in connection with the present invention, embodiments include near infrared signaling agents. Also includes are dyes, such as, for example, near-infrared fluorophores/fluorescent dyes. Examples include cyanine dyes which have been used to label various biomolecules. See U.S. Pat. No. 5,268,486, which discloses fluorescent arylsulfonated cyanine dyes having large extinction coefficients and quantum yields for the purpose of detection and quantification of labeled components.

Additional examples include compounds of the following formulas:

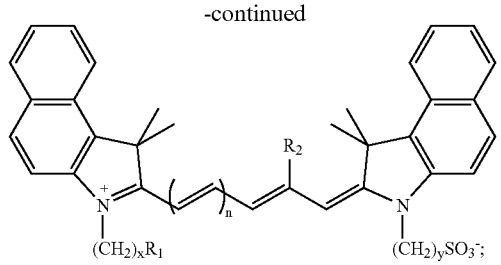

General Cyanine dye

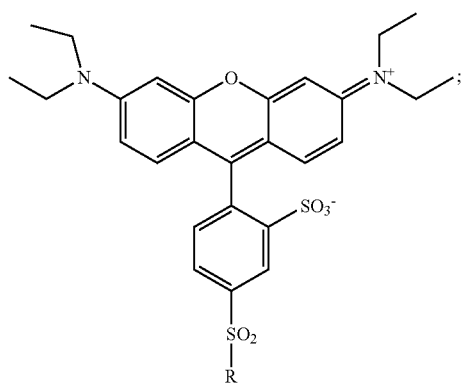

Lissamine-Rhodamine abs/em = 560 nm, 590 nm

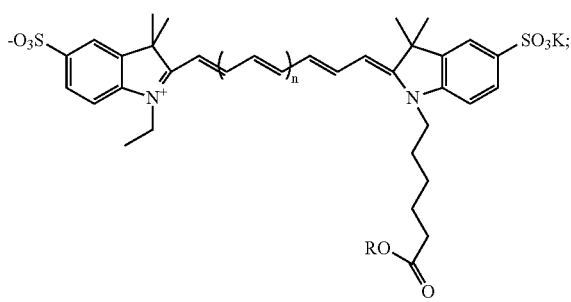

CY-Family of dyes and analogs thereof.

Additional examples include dyes available from Li-Cor, such as IR Dye 800CW™, available from Li-Cor.

Thus, examples of dyes for use in connection with the present invention include those disclosed in U.S. Pat. No. 6,995,274, the contents of which are incorporated herein by reference.

The following dye is a specific example:

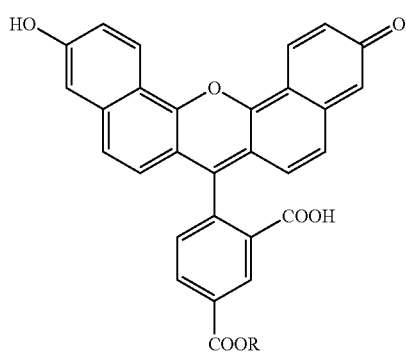

Carboxynaphthofluorescein abs/em = 580 nm, 690 nm

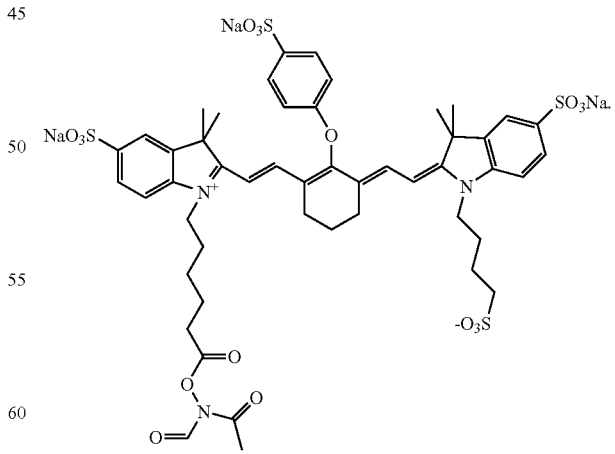

U.S. Pat. No. 6,995,274 additionally discloses the following dyes, all of which, when joined with a probe, are embodiments of the present invention:

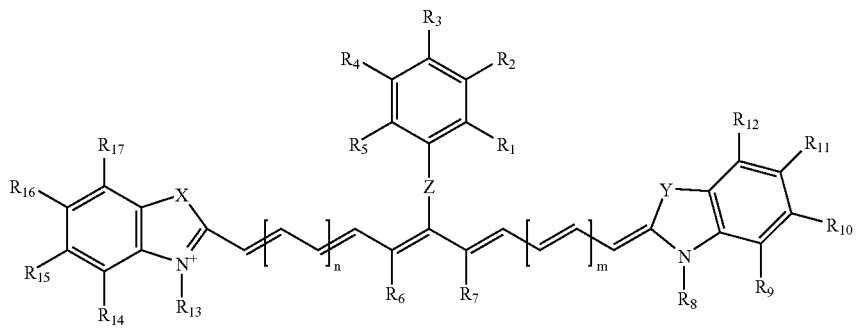

wherein, Z is a heteroatom having at least one lone pair of electrons. In one embodiment, Z is O, S, or $N_{35}$, wherein $R_{35}$ is H or alkyl. In embodiments, Z is of such a structure that only one atom is in the direct linkage between the benzene ring bonded to Z and to the polyene chain of: ⌒, bonded to Z. Side chains on the linkage between the benzene ring and the polyene chain are acceptable. In those embodiments having side chains, lower alkyl side chains may be used.

$R_1$-$R_5$ are each independently H, alkyl, halo, carboxyl, amino, or $SO_3$-$Cat^+$, wherein $Cat^+$ is a cation and at least one of $R_1$-$R_5$ is $SO_3$-$Cat^+$. In embodiments, $R_3$ is $SO_3$-$Cat^+$. In other embodiments, $Cat^+$ is $H^+$ or an alkali metal ion such as $Na^+$.

$R_6$ and $R_7$ are each H, alkyl, or optionally, together with the ⌒ group to which they are bonded, form a ring. In embodiments, $R_6$ and $R_7$ together with the atoms to which they are bonded form a ring. These rings may have 4 to 10 member atoms, more preferably 5 or 6 member atoms. In one embodiment, the ring including $R_6$ and $R_7$ is substituted, with, for example, a sulfonato radical.

The integers m and n are each independently integers from 0 to 5. In embodiments, both the sum of m and n is two. Additionally, the sum of m and n may be one. In other embodiments, both m and n are zero. As the sum of m and n rises, so too does the wavelength of the dye. Generally, the addition of each double bond in the polyene chain can increase the wavelength by about 40 to 120 nm. For the absorption changes accompanied with trimethine to pentamethine or pentamethine to heptamethine, there is a typically a bathochromic shift (red shift) of about 100 nm. For example, when m and n are both 0, the wavelength of the preferred dye is about 770 nm. When m and n are both 1, the wavelength of the preferred dye is about 950 nm. The most preferred dyes operate in the NIR spectrum (600-1000 nm).

X and Y are each independently O, S, Se, or $CR_{19}R_{20}$, wherein $R_{19}$ and $R_{20}$ are each independently alkyl, or optionally form a ring together with the carbon atom to which they are bonded. In embodiments, X and Y are a heteroatom such as O, S, and Se. When X or Y is $CR_{19}R_{20}$, both $R_{19}$ and $R_{20}$ may be both lower alkyl, including methyl.

$R_8$ and $R_{13}$ are each independently alkyl, $(CH_2)_rR_{25}$ or $(CH_2)_rR_{19}$; wherein at least one of $R_8$ and $R_{13}$ is $(CH_2)_rR_{18}$ and wherein r is an integer from 1 to 50, and $R_{25}$ is a functional group that does not directly react with a carboxyl, hydroxyl, amino, or a thiol group, and $R_{18}$ is a functional group that can react with a carboxyl, hydroxyl, amino, or thiol group. In one embodiment, one of $R_8$ and $R_{13}$ is $(CH_2)_rR_{18}$ and the other is $(CH_2)_rR_{25}$. In other words, one of $R_8$ and $R_{13}$ reacts with a biomolecule to form a bond to that biomolecule, and that the other does not react. The $R_{18}$ group must be able to covalently bond with the biomolecule being labeled. $R_{18}$ groups include mercapto, carboxyl, amino, haloalkyl, phosphoramidityl, N-hydroxy succinimidyl ester, sulfo N-hydroxy succinimidyl ester, isothiocyanato, iodoacetamidyl, and maleimidyl. $R_{25}$ groups include hydroxyl, thioacetyl, and sulfonato.

$R_9$-$R_{12}$ and $R_{14}$-$R_{17}$ are each independently H, alkyl, halo, amino, sulfonato, $R_{21}COOH$, $R_{21}OR_{22}$, $R_{21}SR_{22}$, or $R_{21}COOR_{22}$ wherein $R_{21}$ is a bond or alkylene and $R_{22}$ is alkyl, or optionally $R_{11}$ and $R_{12}$ together with the atoms to which they are bonded form an aromatic ring, or optionally $R_{16}$ and $R_{17}$ together with the atoms to which they are bonded form an aromatic ring. In one embodiment, one or both of $R_{11}$ and $R_{16}$ is sulfonato. In another embodiment, when $R_{11}$ and $R_{12}$ together with the atoms to which they are bonded form an aromatic ring, the ring is substituted in at least one position with a sulfonato group. In another embodiment, when $R_{16}$ and $R_{17}$ together with the atoms to which they are bonded form an aromatic ring, the ring is substituted in at least one position with a sulfonato group, a halo group, an alkyl substituent, or an amino substituent.

Another cyanine dye that can be used with the present invention is of the following formula:

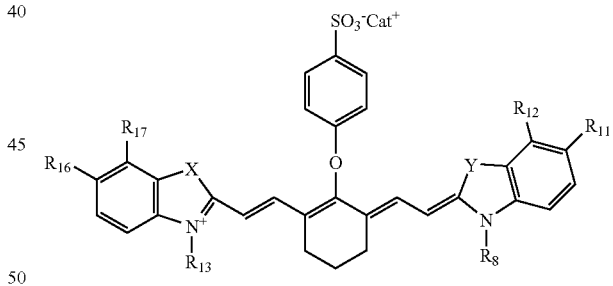

$Cat^+$ is a cation. In embodiments, $Cat^+$ is $H^+$ or a metal ion. More preferably, $Cat^+$ is an alkali metal ion, most preferably $Na^+$. X and Y are each independently O, S, Se, or $(CH_3)_2C$.

$R_8$ and $R_{13}$ are each independently alkyl, $(CH_2)_rR_{25}$ or $(CH_2)_rR_{19}$; wherein at least one of $R_8$ and $R_{13}$ is $(CH_2)_rR_{18}$ and wherein r is an integer from 1 to 50, and $R_{25}$ is a functional group that does not directly react with a carboxyl, hydroxyl, amino, or a thiol group, and $R_{18}$ is a functional group that can react with a carboxyl, hydroxyl, amino, or thiol group. In one embodiment, one of $R_8$ and $R_{13}$ is $(CH_2)_rR_{18}$ and the other is $(CH_2)_rR_{25}$. In other words, one of $R_8$ and $R_{13}$ reacts with a biomolecule to form a bond to that biomolecule, and that the other does not react. The $R_{18}$ group must be able to covalently bond with the biomolecule being labeled. $R_{18}$ groups include mercapto, carboxyl, amino, haloalkyl, phosphoramidityl, N-hydroxy succinimidyl ester, sulfo N-hydroxy succinimidyl ester, isothiocyanato, iodoacetamidyl, and maleimidyl. $R_{25}$ groups include hydroxyl, thioacetyl, and sulfonato.

$R_{11}$ and $R_{12}$ are either H, sulfonato, or together with the atoms to which they are bonded form an aromatic ring. In a preferred embodiment, $R_{11}$ is sulfonato. In another preferred embodiment, when $R_{11}$ and $R_{12}$ together with the atoms to which they are bonded form an aromatic ring, the ring is substituted in at least one position with a sulfonato group.

$R_{16}$ and $R_{17}$ are either H, sulfonato, or together with the atoms to which they are bonded form an aromatic ring. In a preferred embodiment, $R_{16}$ is sulfonato. In another preferred embodiment, when $R_{16}$ and $R_{17}$ together with the atoms to which they are bonded form an aromatic ring, the ring is substituted in at least one position with a sulfonato group.

Further examples of cyanine dyes that can be used in connection with the present invention are those cyanine dyes that can be excited efficiently by commercially available equipment purchasable through companies such as Toshiba, Phillips, Blue Sky Research, and NEC.

Examples of how the above cyanine dyes may be prepared are shown in US 2004/0014981. That is, the cyanine dyes disclosed herein are prepared using methods that are well known in the art. Generally, cyanine dyes are prepared according to the procedures taught in Hamer, F. M., Cyanine Dyes and Related Compounds, Weissberger, M. A., ed. Wiley Interscience, N.Y. 1964. Further, U.S. Pat. Nos. 4,337,063; 4,404,289 and 4,405,711, incorporated herein by reference, describe a synthesis for a variety of cyanine dyes having N-hydroxysuccinimide active ester groups. U.S. Pat. No. 4,981,977, incorporated herein by reference, describes a synthesis for cyanine dyes having carboxylic acid groups. U.S. Pat. No. 5,268,486, incorporated herein by reference, discloses a method for making arylsulfonate cyanine dyes. U.S. Pat. No. 6,027,709, discussed below, and incorporated herein by reference, discloses methods for making cyanine dyes having phosphoramidite groups. U.S. Pat. No. 6,048,982, incorporated herein by reference, discloses methods for making cyanine dyes having a reactive group selected from the group consisting of isothiocyanate, isocyanate, phosphoramidite, monochlorotriazine, dichlorotriazine, mono- or di-halogen substituted pyridine, mono- or di-halogen substituted diazine, aziridine, sulfonyl halide, acid halide, hydroxysuccinimide ester, hydroxy sulfosuccinimide ester, imido ester, glyoxal and aldehyde.

Additional dyes that can be used with the present invention are the following:

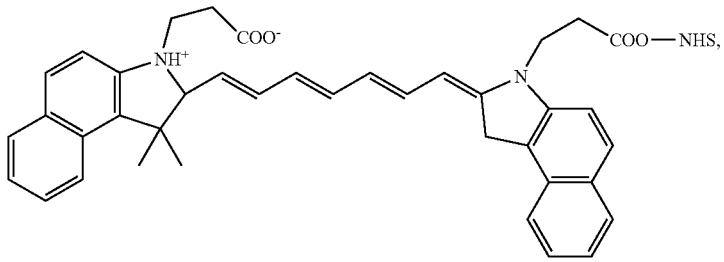

Cypate NHS-Achillifu

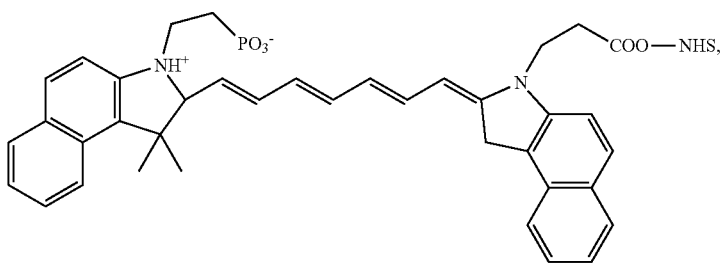

CY5.5- Amersham, Invitrogen

-continued

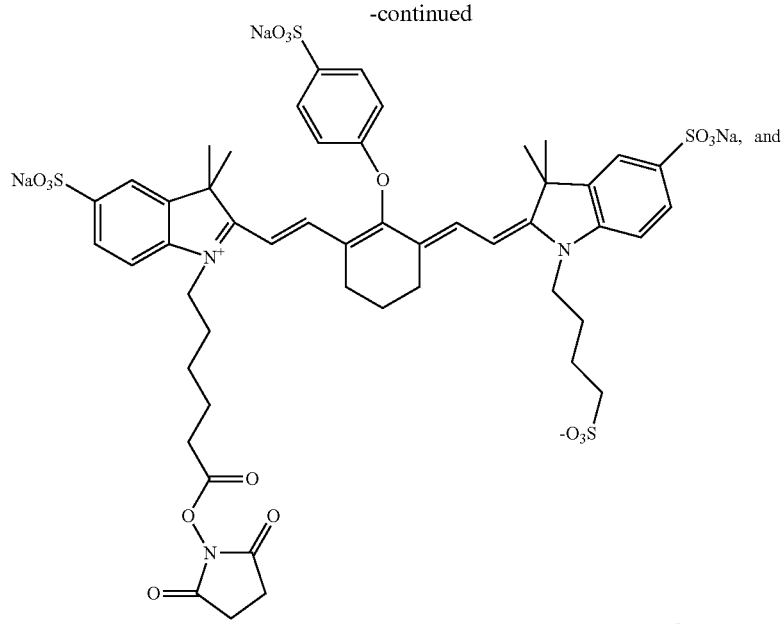

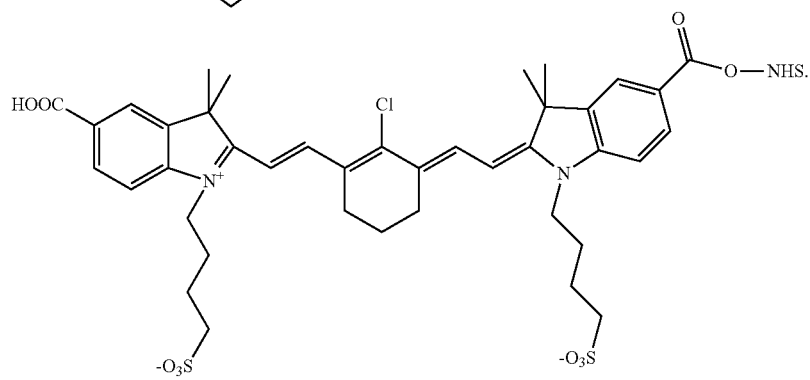

NIR-820 Pham, Tung et al

Even further examples include the dyes disclosed in U.S. Pat. No. 6,027,709.

US '709 discloses dyes which have the following general formula:

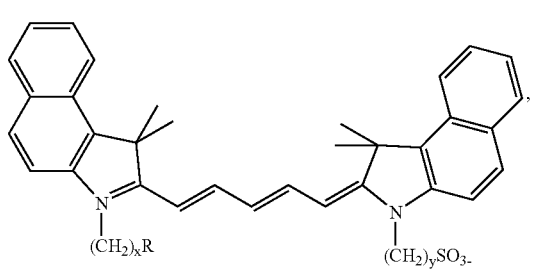

wherein R is —OH, —CO$_2$H, —NH$_2$, or —NCS and each of x and y, independently, is an integer selected from 1 to about 10. In preferred embodiments, each of x and y, independently, is an integer between about 2 and 6.

In one embodiment, the dye is N-(6-hydroxyhexyl)N'—(4-sulfonatobutyl)-3,3,3',3'-tetramethylbenz(e)indod icarbocyanine, which has the formula:

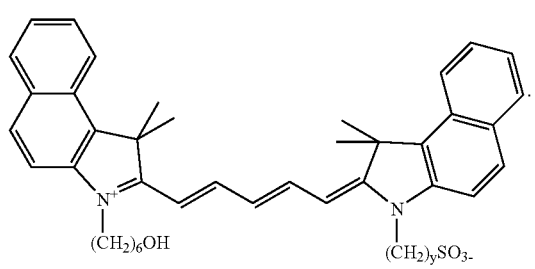

In a second embodiment, the dye is N-(5-carboxypentyl) N'—(4-sulfonatobutyl)3,3,3',3'-tetramethylbenz(e)indodi-carbocyanine, which has the formula:

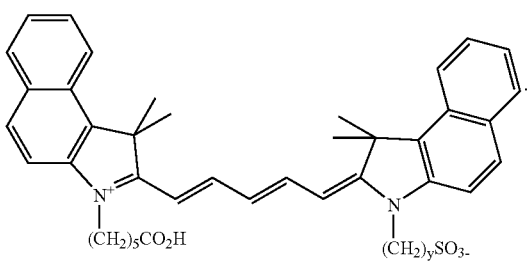

These two dyes are embodiments because they have commercially available precursors for the linking groups: 6-bromohexanol, 6-bromohexanoic acid and 1,4-butane sultone (all available from Aldrich Chemical Co., Milwaukee, Wis.). The linking groups provide adequate distance between the dye and the biomolecule for efficient attachment without imparting excessive hydrophobicity. The resulting labeled biomolecules retain their solubility in water and are well-accepted by enzymes.

These dyes, wherein R is —CO₂H or —OH can be synthesized, as set forth in detail in the US '709 patent, by reacting the appropriate N-(carboxyalkyl)- or N-(hydroxyalkyl)-1,1,2-trimethyl-1H-benz(e)indolinium halide, preferably bromide, with sulfonatobutyl-1,1,2-trimethyl-1H-benz(e)indole at a relative molar ratio of about 0.9:1 to about 1:0.9, preferably 1:1 in an organic solvent, such as pyridine, and heated to reflux, followed by the addition of 1,3,3-trimethoxypropene in a relative molar ratio of about 1:1 to about 3:1 to the reaction product and continued reflux. The mixture subsequently is cooled and poured into an organic solvent such as ether. The resulting solid or semi-solid can be purified by chromatography on a silica gel column using a series of methanol/chloroform solvents.

As an alternative, two-step, synthesis procedure, also detailed in U.S. '709, N-4-sulfonatobutyl-1,1,2-trimethyl-1H-benz(e)indole and malonaldehyde bis(phenyl)mine)-monohydrochloride in a 1:1 molar ratio can be dissolved in acetic anhydride and the mixture heated. The acetic anhydride is removed under high vacuum and the residue washed with an organic solvent such as ether. The residual solid obtained is dried and subsequently mixed with the appropriate N-(carboxyalkyl)- or N-(hydroxyalkyl)-1,1,2-trimethyl-1H-benz(e)indolinium halide in the presence of an organic solvent, such as pyridine. The reaction mixture is heated, then the solvent is removed under vacuum, leaving the crude desired dye compound. The procedure was adapted from the two step procedure set forth in Ernst, L. A., et al., Cytometry 10:3-10 (1989).

The dyes also can be prepared with an amine or isothiocyanate terminating group. For example, N-(omega.-aminoalkyl)-1,1,2-trimethyl-1H-benz(e)indolenium bromide hydrobromide (synthesized as in N. Narayanan and G. Patonay, J. Org. Chem. 60:2391-5 (1995)) can be reacted to form dyes of formula 1 wherein R is —NH₂. Salts of these amino dyes can be converted to the corresponding isothiocyanates by treatment at room temperature with thiophosgene in an organic solvent such as chloroform and aqueous sodium carbonate.

These dyes have a maximum light absorption which occurs near 680 nm. They thus can be excited efficiently by commercially available laser diodes that are compact, reliable and inexpensive and emit light at this wavelength. Suitable commercially available lasers include, for example, Toshiba TOLD9225, TOLD9140 and TOLD9150, Phillips CQL806D, Blue Sky Research PS 015-00 and NEC NDL 3230SU. This near infrared/far red wavelength also is advantageous in that the background fluorescence in this region normally is low in biological systems and high sensitivity can be achieved.

The hydroxyl, carboxyl and isothiocyanate groups of the dyes provide linking groups for attachment to a wide variety of biologically important molecules, including proteins, peptides, enzyme substrates, hormones, antibodies, antigens, haptens, avidin, streptavidin, carbohydrates, oligosaccharides, polysaccharides, nucleic acids, deoxy nucleic acids, fragments of DNA or RNA, cells and synthetic combinations of biological fragments such as peptide nucleic acids (PNAs).

In another embodiment of the present invention, the ligands of the present invention may be conjugated to a lissamine dye, such as lissamine rhodamine B sulfonyl chloride. For example, a conjugable form of DAA1106 may be conjugated with lissamine rhodamine B sulfonyl chloride to form a compound of the present invention.

Lissamine dyes are typically inexpensive dyes with attractive spectral properties. For example, examples have a molar extinction coefficient of 88,000 cm⁻¹ M⁻¹ and good quantum efficient of about 95%. It absorbs at about 568 nm and emits at about 583 nm (in methanol) with a decent stokes shift and thus bright fluorescence.

Coupling procedures for the PBR ligands and Glucosamine proceed via standard methods and will be recognized by those skilled in the art. In general, the nucleophilic N terminus of the targeting moieties are reactive towards activated carbonyls, for example an NHS (N-hydroxysuccinimide ester), sulfonyl chlorides, or other electrophile bearing species. Solvent of choice for coupling reactions can be dye specific, but include dimethyl sulfoxide (DMSO), chloroform, and/or phosphate buffered saline (PBS buffer). The resulting conjugates, amides, sulfonamides, etc. resist hydrolysis under physiological conditions, and are thus useful for in-vivo and in-vitro application.

The following are examples of compounds of the present invention:

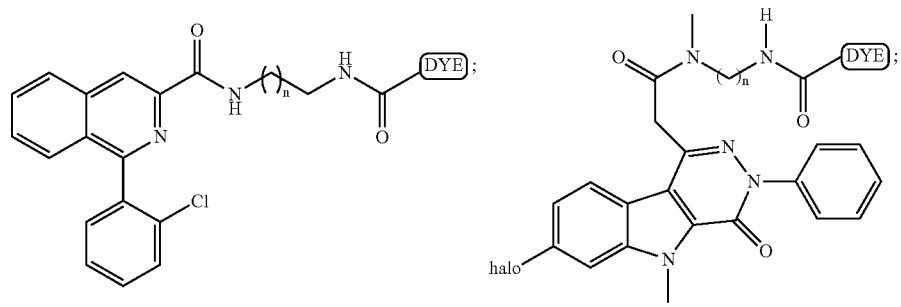

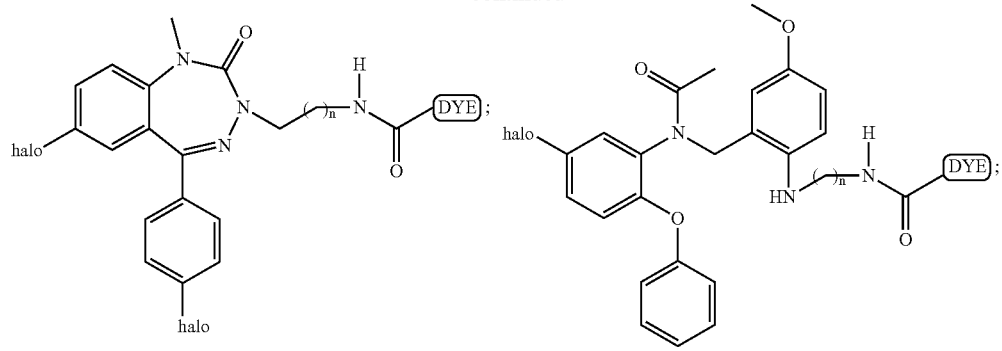
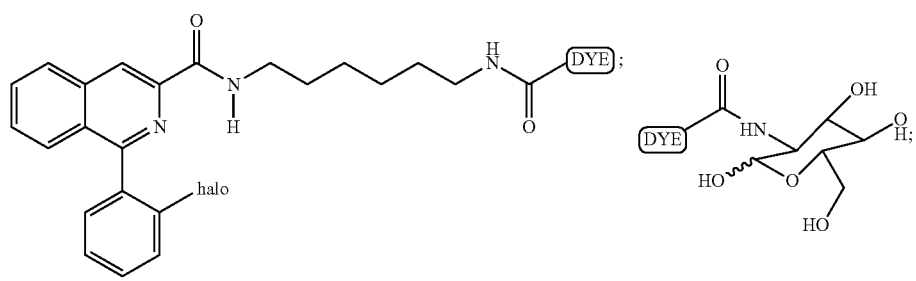
The following are examples of dyes in conjugable form
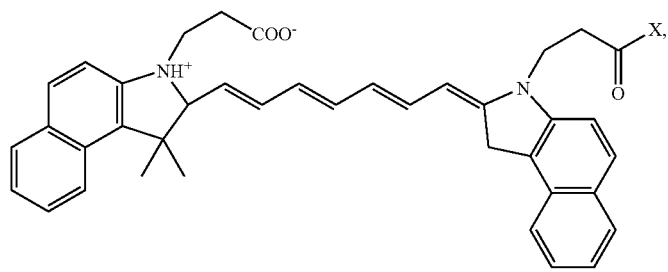
Cypate: X = Conjugation Site
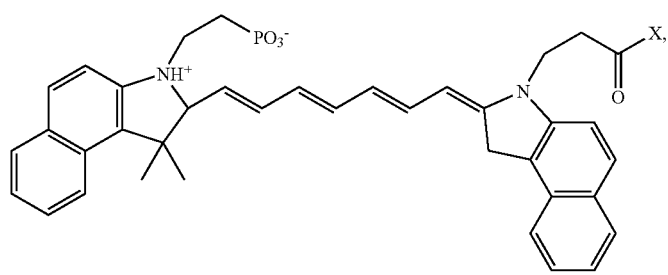
CY5.5: X = Conjugation Site

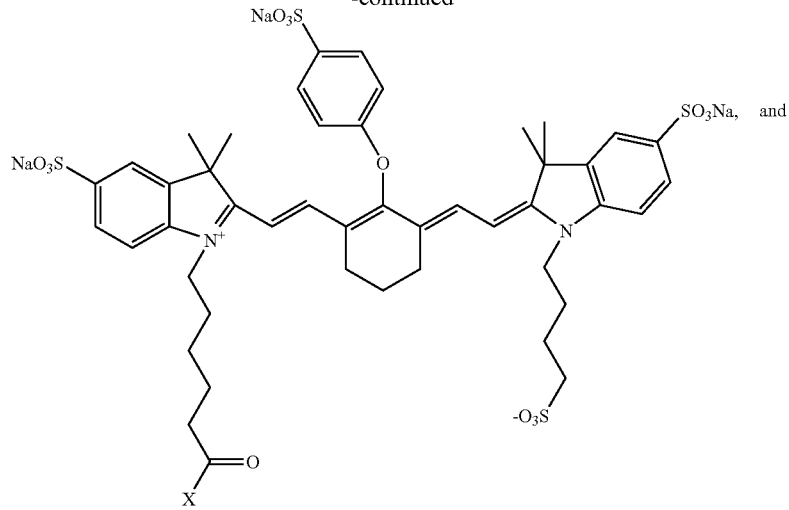
LI-COR 800CW: X = Conjugation Site
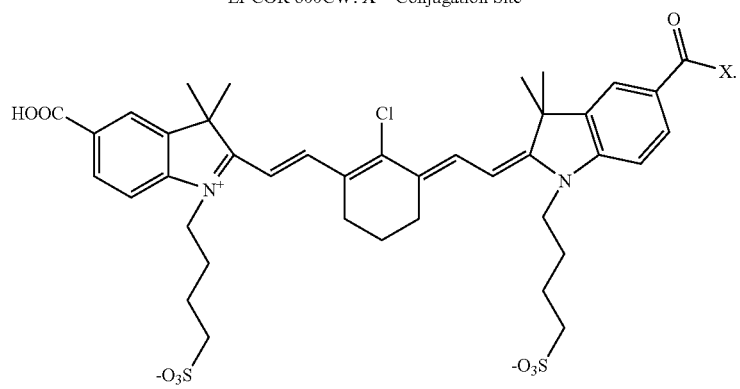
NIR-820: X = Conjugation Site
The following compound is an example of one of the coupled compounds described above:
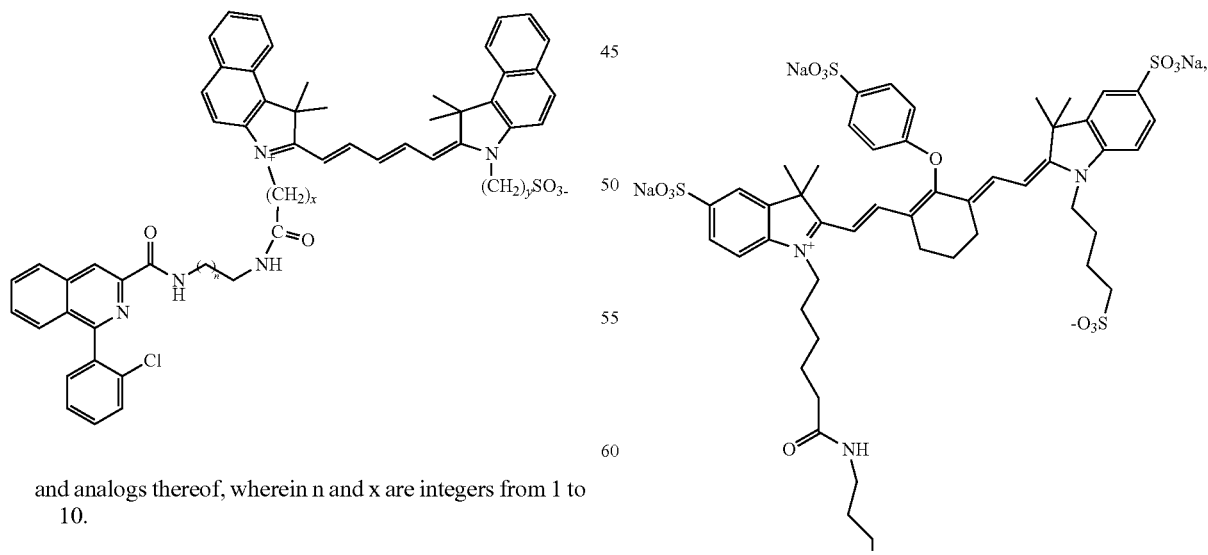
and analogs thereof, wherein n and x are integers from 1 to 10.
The following is an additional example of a compound of the present invention, comprising a probe and a signaling moiety conjugated thereto:

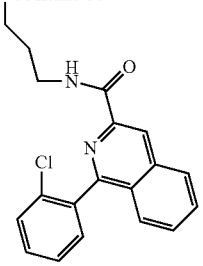

and analogs thereof.

As stated above, the compounds of the present invention can be employed as signaling agents in NIR imaging. The resulting signal may be used to image a molecular event. Non-limiting examples of specific molecular events associated with the present invention include at least one of peripheral benzodiazepine expression, cell proliferation, glucose uptake, epidermal growth factor receptor expression, coronary disease.

Thus, the resulting signal may be used to diagnose a disease state such as, for example, cancer, neurodegenerative disease, multiple sclerosis, epilepsy, coronary disease, etc. Specifically, brain cancer and breast cancer are two cancers that may be diagnosed with the compounds and methods of the present invention. Two additional examples are non-Hodgkin's lymphoma and colon cancer.

Another embodiment of the present invention is a method of measuring glucose uptake. This method comprises, comprises administering to a sample a conjugate, the conjugate comprising a conjugable glucosamine compound and a signaling agent; and detecting a signal from said conjugate. As in the other methods, the sample is at least one of cells, tissue, cellular tissue, serum or cell extract. An example of a conjugable glucosamine includes the following compound and conjugable analog thereof:

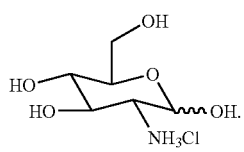

The administration step may be in vivo administration or in vitro administration. The in vivo administration step further comprises at least one time course imaging determination, and in other embodiments, the in vivo administration step further comprises at least one bio distribution determination.

Other embodiments of the present invention include conjugable compounds associated with this glucosamine method, specifically including the following:

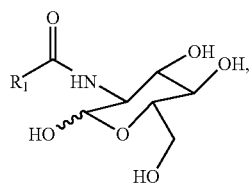

where $R_1$ is a signaling moiety, and

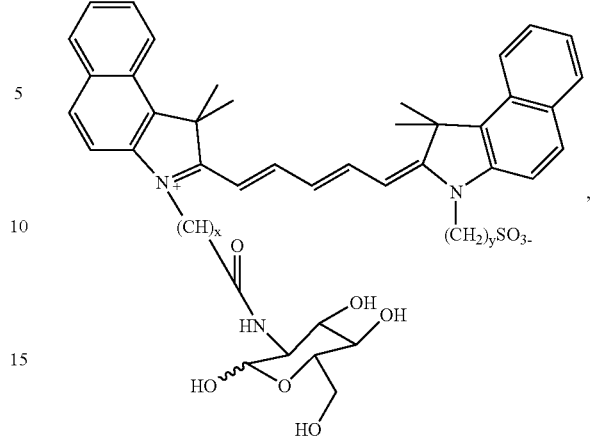

and analogs thereof.

As indicated above, a conjugable analog of DAA1106 has been synthesized and characterized. The analog has a terminal amino group, facilitating coupling reactions.

The following is an example of a compound of the present invention:

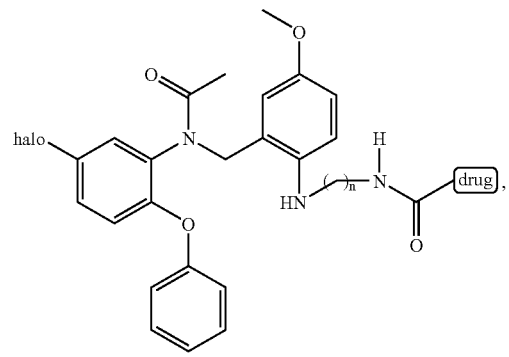

and stereoisomers and conjugable analogs thereof.

Additionally, the following is an example of a compound of the present invention:

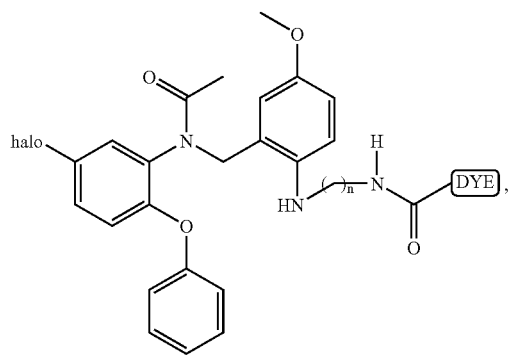

and stereoisomers and conjugable analogs thereof.

Unless disclosed otherwise, in the above examples and the compounds disclosed herein, N is an integer from 1 to 10.

Aspects of the invention related to imaging are carried out as described in Bornhop et al., US Application Publication Number 20060147379, incorporated herein by reference.

Two fluorescent dyes, IRDye™ 800CW NHS ester (LI-COR Biosciences, ε=300,000 L/mol cm in methanol) and lissamine™ rhodamine B sulphonyl chloride (Invitrogen, ε=300,000 L/mol cm in methanol) are examples of signaling parts to conjugate to the DAA1106 analog. The resulting compounds of the present invention have nanomolar binding affinities to PBR and appear to target PBR in vitro.

Also includes are dyes, such as, for example, near-infrared fluorophores/fluorescent dyes. Examples include cyanine dyes which have been used to label various biomolecules. See U.S. Pat. No. 5,268,486, which discloses fluorescent arylsulfonated cyanine dyes having large extinction coefficients and quantum yields for the purpose of detection and quantification of labeled components.

Additional examples include compounds of the following formulas:

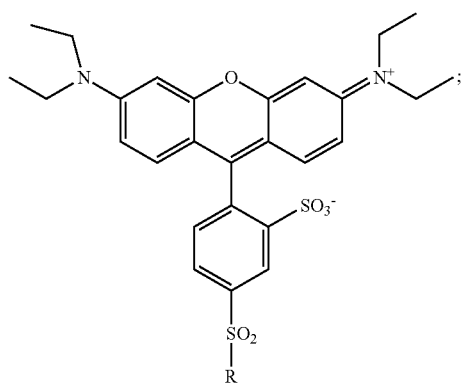

Lissamine-Rhodamine abs/em = 560 nm, 590 nm

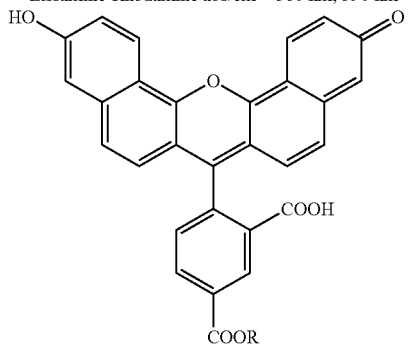

Carboxynaphthofluorescein abs/em = 580 nm, 690 nm

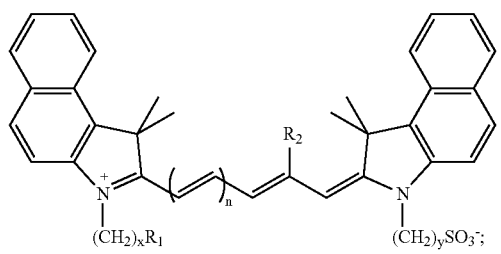

General Cyanine dye

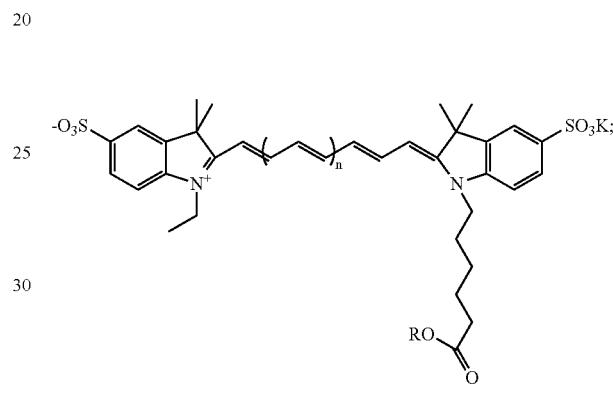

CY-Family of dyes and analogs thereof.

Additional examples include dyes available from Li-Cor, such as IRDye™ 800CW. For example, dyes disclosed in WO 02/24815, incorporated herein by reference, are dyes of the present invention. Furthermore, dyes disclosed in U.S. patent application Ser. No. 11/267,643, incorporated herein by reference, are dyes of the present invention. Additionally, dyes of U.S. Pat. No. 6,995,274, incorporated herein by reference, are dyes of the present invention.

Thus, a compound of the present invention is the following:

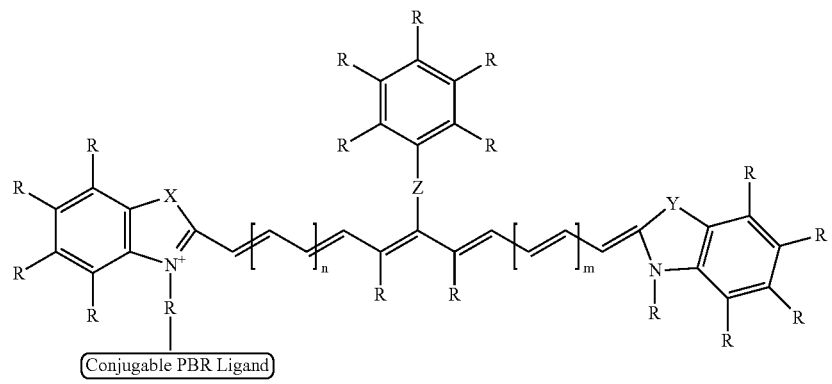

wherein the variables are defined in US patent application publication number 20060063247, incorporated herein by reference.

Additional examples of dyes usable with the present invention include dyes disclosed in U.S. Pat. No. 6,027,709. US '709 discloses dyes which have the following general formula:

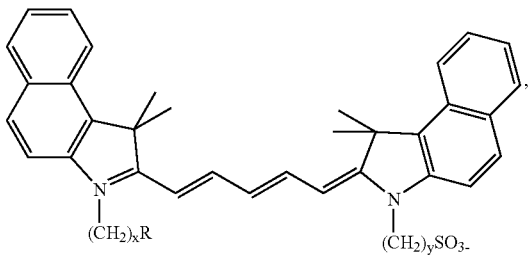

wherein R is —OH, —CO$_2$H, —NH$_2$, or —NCS and each of x and y, independently, is an integer selected from 1 to about 10. In preferred embodiments, each of x and y, independently, is an integer between about 2 and 6.

In one embodiment, the dye is N-(6-hydroxyhexyl)N'—(4-sulfonatobutyl)-3,3,3',3'-tetramethylbenz(e)indod icarbocyanine, which has the formula:

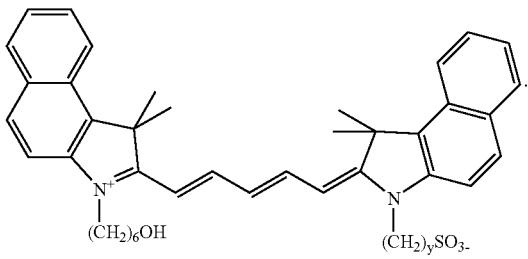

In a second embodiment, the dye is N-(5-carboxypentyl) N'—(4-sulfonatobutyl)3,3,3',3'-tetramethylbenz(e)indodicarbocyanine, which has the formula:

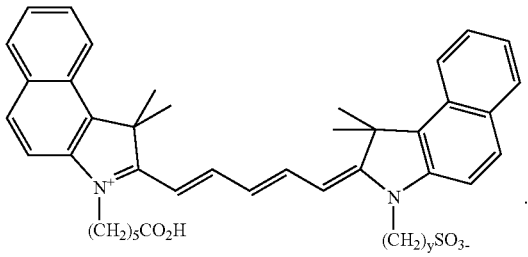

These two dyes are embodiments because they have commercially available precursors for the linking groups: 6-bromohexanol, 6-bromohexanoic acid and 1,4-butane sultone (all available from Aldrich Chemical Co., Milwaukee, Wis.). The linking groups provide adequate distance between the dye and the biomolecule for efficient attachment without imparting excessive hydrophobicity. The resulting labeled biomolecules retain their solubility in water and are well-accepted by enzymes.

These dyes, wherein R is —CO$_2$H or —OH can be synthesized, as set forth in detail in the US '709 patent, by reacting the appropriate N-(carboxyalkyl)- or N-(hydroxyalkyl)-1,1,2-trimethyl-1H-benz(e)indolinium halide, preferably bromide, with sulfonatobutyl-1,1,2-trimethyl-1H-benz(e)indole at a relative molar ratio of about 0.9:1 to about 1:0.9, preferably 1:1 in an organic solvent, such as pyridine, and heated to reflux, followed by the addition of 1,3,3-trimethoxypropene in a relative molar ratio of about 1:1 to about 3:1 to the reaction product and continued reflux. The mixture subsequently is cooled and poured into an organic solvent such as ether. The resulting solid or semi-solid can be purified by chromatography on a silica gel column using a series of methanol/chloroform solvents.

As an alternative, two-step, synthesis procedure, also detailed in U.S. '709, N-4-sulfonatobutyl-1,1,2-trimethyl-1H-benz(e)indole and malonaldehyde bis(phenyl)mine)-monohydrochloride in a 1:1 molar ratio can be dissolved in acetic anhydride and the mixture is heated. The acetic anhydride is removed under high vacuum and the residue is washed with an organic solvent such as ether. The residual solid obtained is dried and subsequently mixed with the appropriate N-(carboxyalkyl)- or N-(hydroxyalkyl)-1,1,2-trimethyl-1H-benz(e)indolinium halide in the presence of an organic solvent, such as pyridine. The reaction mixture is heated, then the solvent is removed under vacuum, leaving the crude desired dye compound. The procedure was adapted from the two step procedure set forth in Ernst, L. A., et al., Cytometry 10:3-10 (1989).

The dyes also can be prepared with an amine or isothiocyanate terminating group. For example, N-(omega.-aminoalkyl)-1,1,2-trimethyl-1H-benz(e)indolenium bromide hydrobromide (synthesized as in N. Narayanan and G. Patonay, J. Org. Chem. 60:2391-5 (1995)) can be reacted to form dyes of formula 1 wherein R is —NH$_2$. Salts of these amino dyes can be converted to the corresponding isothiocyanates by treatment at room temperature with thiophosgene in an organic solvent such as chloroform and aqueous sodium carbonate.

These dyes have a maximum light absorption which occurs near 680 nm. They thus can be excited efficiently by commercially available laser diodes that are compact, reliable and inexpensive and emit light at this wavelength. Suitable commercially available lasers include, for example, Toshiba TOLD9225, TOLD9140 and TOLD9150, Phillips CQL806D, Blue Sky Research PS 015-00 and NEC NDL 3230SU. This near infrared/far red wavelength also is advantageous in that the background fluorescence in this region normally is low in biological systems and high sensitivity can be achieved.

The hydroxyl, carboxyl and isothiocyanate groups of the dyes provide linking groups for attachment to a wide variety of biologically important molecules, including proteins, peptides, enzyme substrates, hormones, antibodies, antigens, haptens, avidin, streptavidin, carbohydrates, oligosaccharides, polysaccharides, nucleic acids, deoxy nucleic acids, fragments of DNA or RNA, cells and synthetic combinations of biological fragments such as peptide nucleic acids (PNAs).

In another embodiment of the present invention, the ligands of the present invention may be conjugated to a lissamine dye, such as lissamine rhodamine B sulfonyl chloride. For example, a conjugable form of DAA1106 may be conjugated with lissamine rhodamine B sulfonyl chloride to form a compound of the present invention.

Lissamine dyes are typically inexpensive dyes with attractive spectral properties. For example, lissamine rhodamine B sulfonyl chloride has a molar extinction coefficient of 88,000 cm$^{-1}$ M$^{-1}$ and good quantum efficient of about 95%. It absorbs at about 568 nm and emits at about 583 nm (in methanol) with a decent stokes shift and thus bright fluorescence.

Coupling procedures for the PBR ligands proceed via standard methods and will be recognized by those skilled in the art. In general, the nucleophilic N terminuses of the targeting moieties are reactive towards activated carbonyls, for example an NHS (N-hydroxysuccinimide ester), sulfonyl chlorides, or other electrophile bearing species. Solvent of choice for coupling reactions can be dye specific, but include dimethyl sulfoxide (DMSO), chloroform, and/or phosphate buffered saline (PBS buffer). The resulting conjugates, amides, sulfonamides, etc. resist hydrolysis under physiological conditions, and are thus useful for in-vivo and in-vitro application.

The administration step may be in vivo administration or in vitro administration. The in vivo administration step further comprises at least one time course imaging determination, and in other embodiments, the in vivo administration step further comprises at least one bio distribution determination.

As an example of a conjugable DAA1106 synthetic pathway is shown in Scheme 1. Compound 1 was synthesized as previously reported. The alkylation reaction of 1 with 2-bromo-5-methoxybenzyl bromide was straightforward and produced 2 in 99% yield. Aromatic substitution of a diamine (with 3-9 carbon linker) resulted in relatively low yield (6%-33%). This is due to several byproducts and decomposition of desired product prior to reaction completion. The optimal reaction time for the conjugable DAA1106 reaction is listed in Table 1.

Scheme 1: Conjugable DAA1106 Synthesis

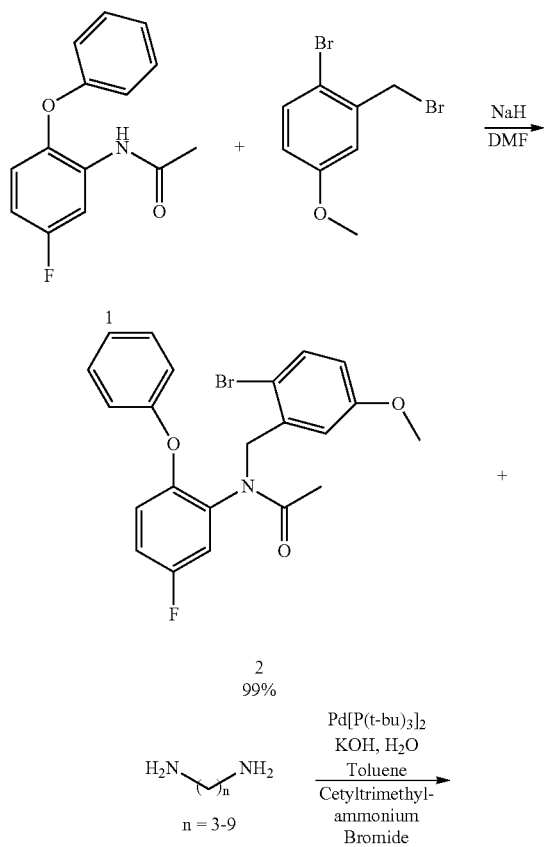

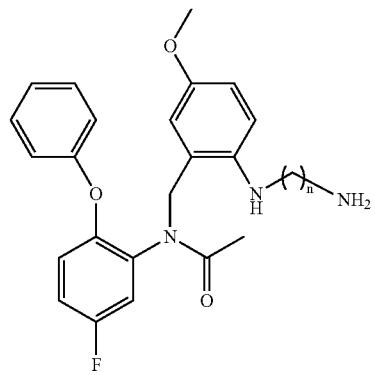

3

TABLE 1

C$_n$DAA1106 reactions summary

| C$_n$DAA1106 | Reaction time (hr) | Yield (%) |
|---|---|---|
| C$_3$DAA1106 | 3 | 8.7 |
| C$_4$DAA1106 | 2 | 7.9 |
| C$_5$DAA1106 | 2 | 10 |
| C$_6$DAA1106 | 6 | 33 |
| C$_7$DAA1106 | 2.5 | 12 |
| C$_8$DAA1106 | 2.5 | 5.8 |
| C$_9$DAA1106 | 2.5 | 11 |

The effect of spacer length on the binding affinity of the conjugable DAA1106 analog has also been investigated. More specifically, conjugable form of DAA1106, with 3-9 carbon spacers, has been synthesized, characterized, and used in a competitive binding assay. The amino group was capped by acetyl group to reduce non-specific binding (Scheme 2). The binding affinity data is shown in Table 2. Conjugable DAA1106 with a 3 carbon linker (C$_3$DAA1106) (IC50=0.39 µM) and C$_7$DAA1106 (IC50=0.40 µM) have higher binding affinities than C$_4$DAA1106 (IC50=0.80 µM) and C$_5$DAA1106 (IC50=0.84 µM), but relatively low binding affinities compared to C$_6$DAA1106 (IC50=0.29 µM), C$_8$DAA1106 (IC50=0.24 µM) and C$_9$DAA1106 (IC50=0.29 µM). Even though these binding affinities are much lower than DAA1106 (IC50=0.28 nM) and [$^{11}$C]DAA1106 (IC50=0.91 nM), the nanomolar binding affities (K$_i$=43-149 nM) appear rather promising. A six carbon linker seems to be the most optimal due to relatively high binding affinity and yield (33%) of C$_6$DAA1106.

TABLE 2

Capped C$_n$DAA1106 binding studies

| C$_n$DAA1106 | IC50 (µM) | Ki (nM) |
|---|---|---|
| C$_3$DAA1106 | 0.39 ± 0.13 | 68 ± 23 |
| C$_4$DAA1106 | 0.80 ± 0.21 | 141 ± 36 |
| C$_5$DAA1106 | 0.84 ± 0.28 | 149 ± 49 |
| C$_6$DAA1106 | 0.35 ± 0.22 | 52 ± 30 |
| C$_7$DAA1106 | 0.40 ± 0.19 | 71 ± 33 |
| C$_8$DAA1106 | 0.24 ± 0.11 | 43 ± 19 |
| C$_9$DAA1106 | 0.29 ± 0.09 | 51 ± 17 |

Scheme 2 Capped DAA1106 analog synthesis
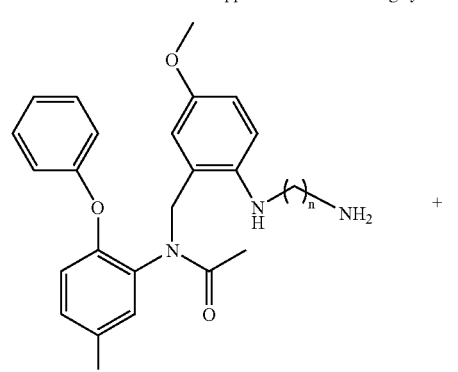
3
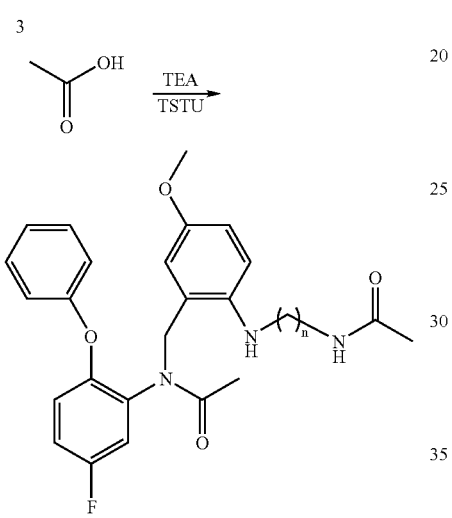
4
Scheme 3 IRDye™ 800CW-C$_6$DAA1106 reaction scheme
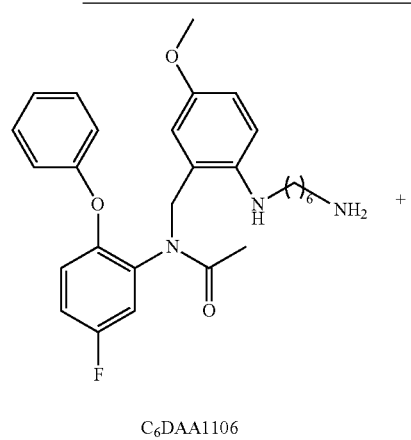
C$_6$DAA1106
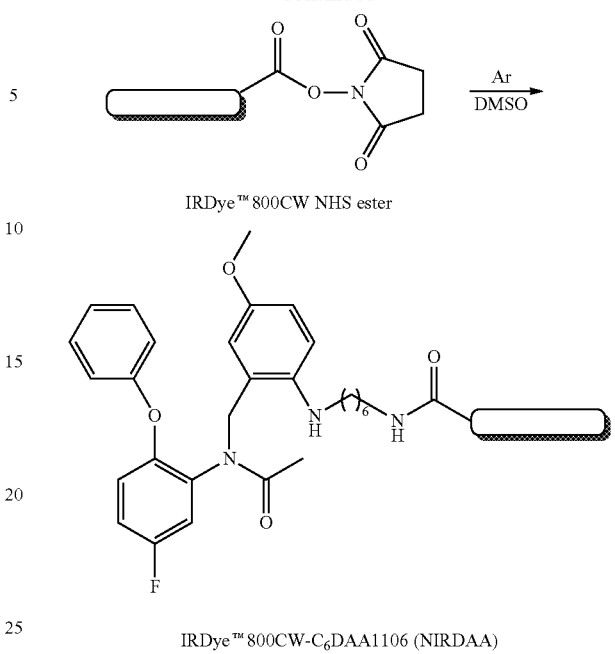
IRDye™ 800CW NHS ester
IRDye™ 800CW-C$_6$DAA1106 (NIRDAA)
Scheme 4 Lissamine-C$_6$DAA1106 reaction scheme
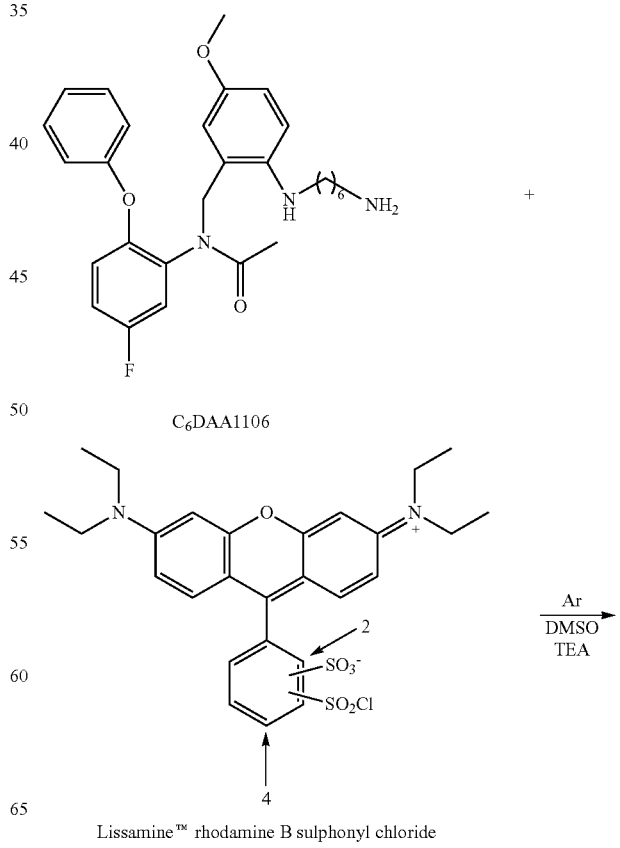
C$_6$DAA1106
Lissamine™ rhodamine B sulphonyl chloride

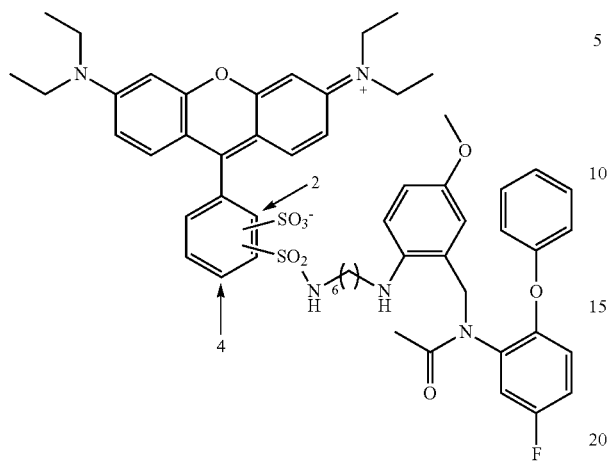

Lissamine-C₆DAA1106 (LissDAA)

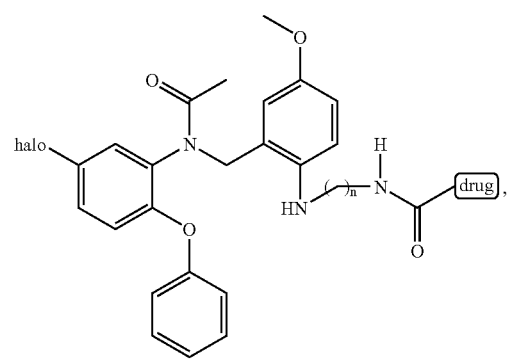

and stereoisomers and conjugable analogs thereof.

The following are further examples of compounds of the present invention:

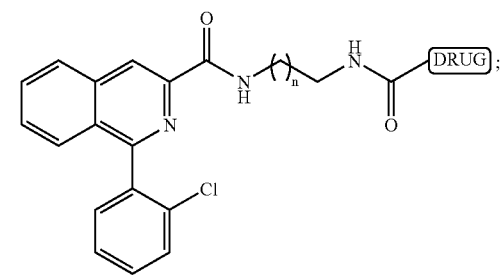

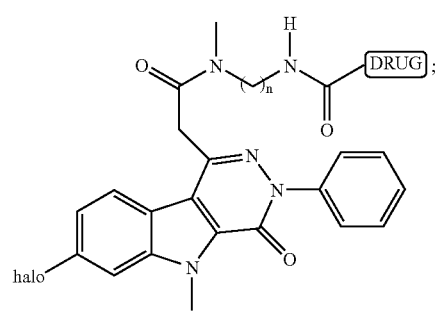

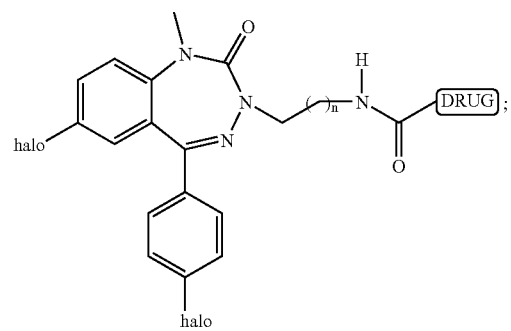

Since NIR probes capable of targeting specific receptors appear to be powerful noninvasive imaging tools for preclinical diagnosis, we conjugated our relative high binding affinity PBR targeted ligand, C₆DAA1106, to IRDye™ 800CW NHS ester. The reaction was straightforward, but the overall yield was relatively low (31%), mainly due the impurities in the dye sample and side reactions.

HPLC was used to monitor the production of IRDye™ 800CW-C₆DAA1106 (NIRDAA). The chromatographs for both the NIR dye and NIRDAA at 780 nm are shown in FIG. 1. FIG. 1 shows the excitation and emission spectra. The excitation of NIRDAA at 778 nm and its subsequent NIR emission at 800 nm allows deep tissue penetration with reduced absorption and scattering for in vivo imaging.

Figure 2:
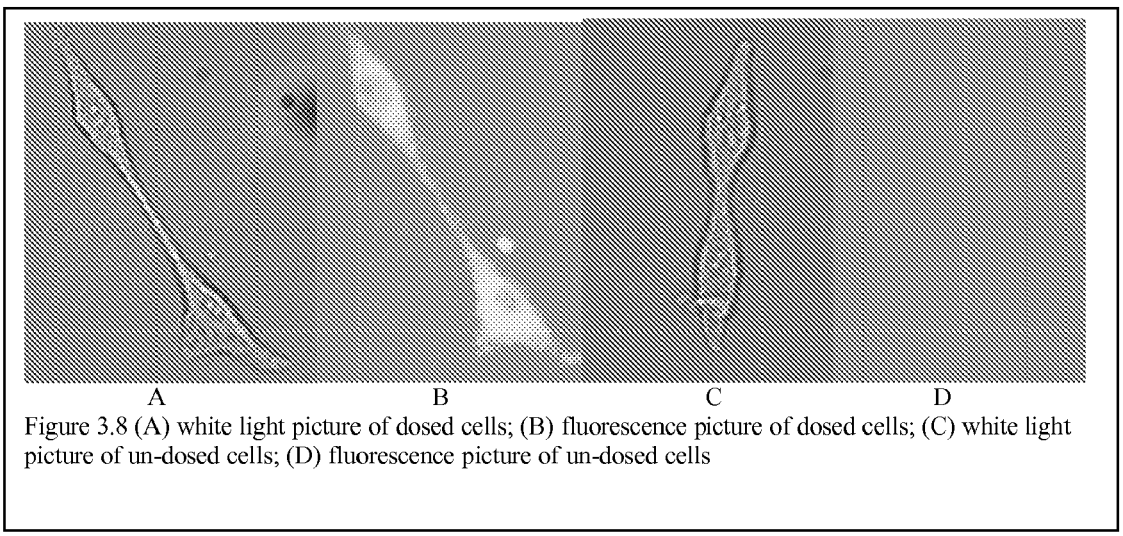
FIG. 2 is a photograph that shows white light and fluorescence pictures of dosed cells and un-dosed cells in accordance with the present invention, and is further discussed in Example 7, below. Picture A is a white light picture of dosed cells, Picture B is a fluorescence picture of dosed cells, Picture C is a white light picture of un-dosed cells, and Picture D is a fluorescence picture of un-dosed cells.

Lissamine™ rhodamine B sulphonyl chloride was also used to conjugate C₆DAA1106. Even though not a NIR dye, the lissamine dye is optimized for commonly used texas red filter set and well known for providing high quality images. Since the commercially available lissamine dye has two isomers, the conjugation reaction yielded two isomers as well. The spectroscopy curves are shown in FIG. 2. Isomer I, which has higher molar extinction coefficient ($\epsilon$=124,000 L/mol cm in methanol) than isomer II ($\epsilon$=80,000 L/mol cm in methanol), was selected for imaging.

Figure 3:
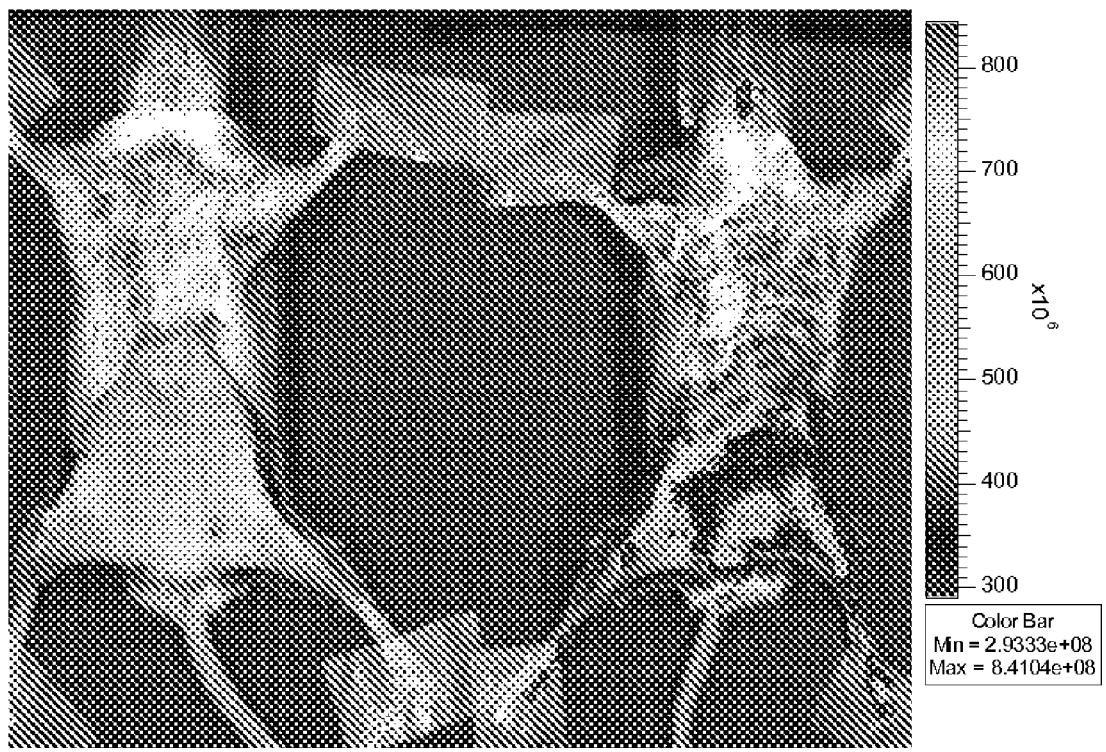
FIG. 3 is a photograph that shows in vivo cancer imaging of a small laboratory animal.
Figure 9:
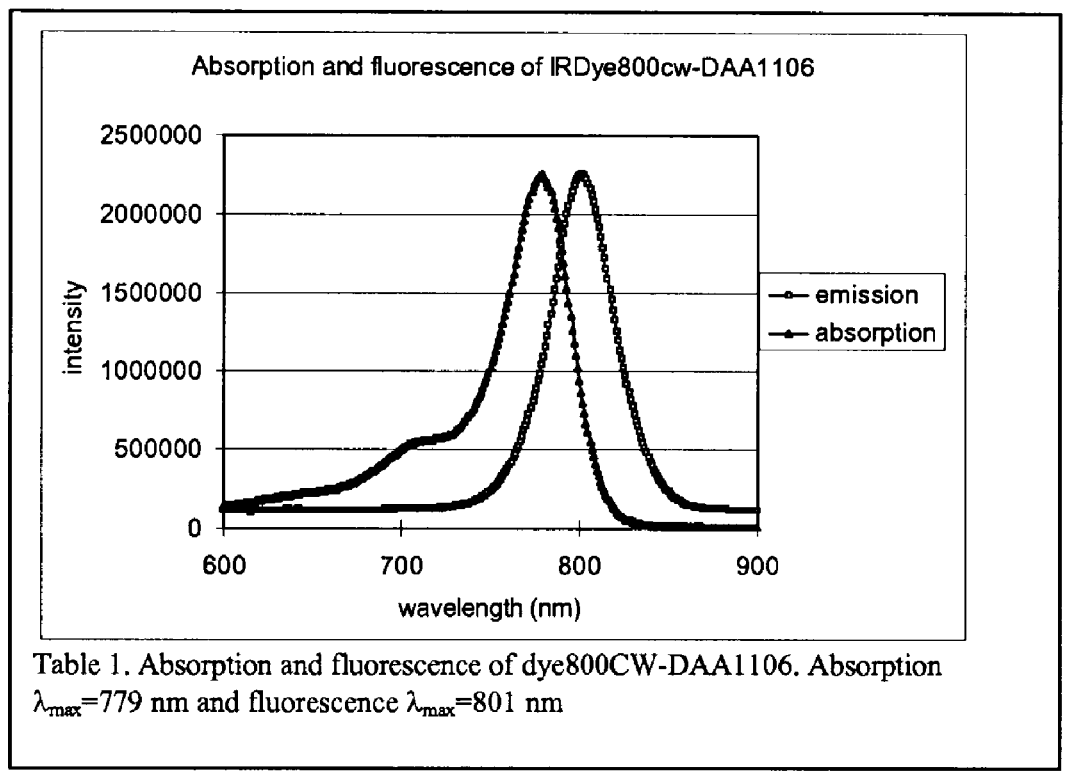
FIG. 9 is a table that shows absorption and fluorescence of dye800CW-DAA1106.
Figure 10:
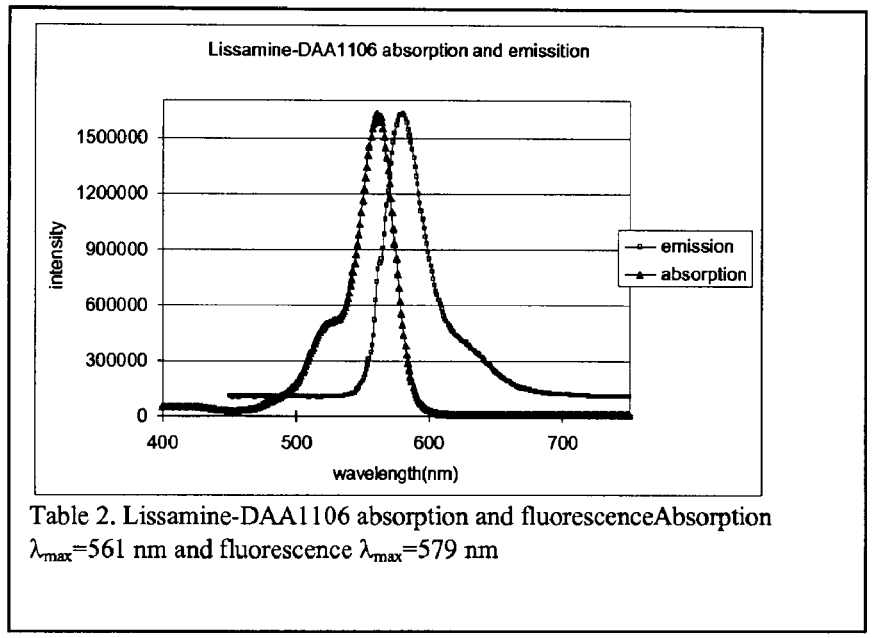
FIG. 10 is a table that shows lissamine-DAA 1106 absorption and fluorescence
Figure 11:
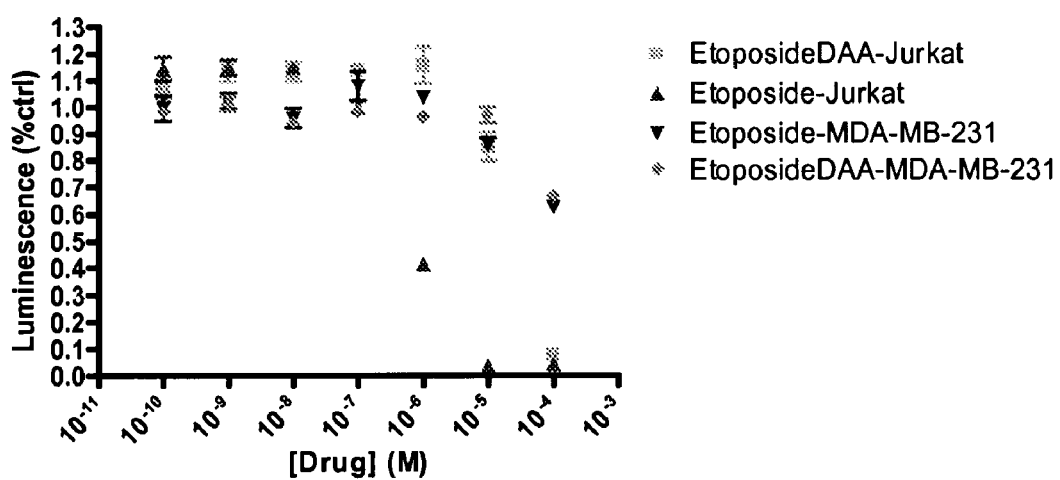
FIG. 11 is a table that fluorescence of various embodiments of the present invention.

Fluorescence microscopy imaging studies were performed to investigate the cell uptake of NIRDAA and LissDAA in MDA-MB-231 (human metastic mammary adenocarcinoma) and C6 (rat glioma) cells. Accumulation of both agents in these cells was found (FIGS. 3 & 4). In addition, MitoTracker Green, which labels mitochondria proteins, was co-incubated with these two molecules in cells. Overlaid pictures demonstrate co-localization of all three molecules, which suggests that the optical probes selectively bind PBR. The nanomolar binding affinities ($K_i$=42 nM for NIRDAA and 0.91 nM for LissDAA) provided further evidence on the selective binding.

As stated above, embodiments of the present invention is a compound of the present invention:

-continued

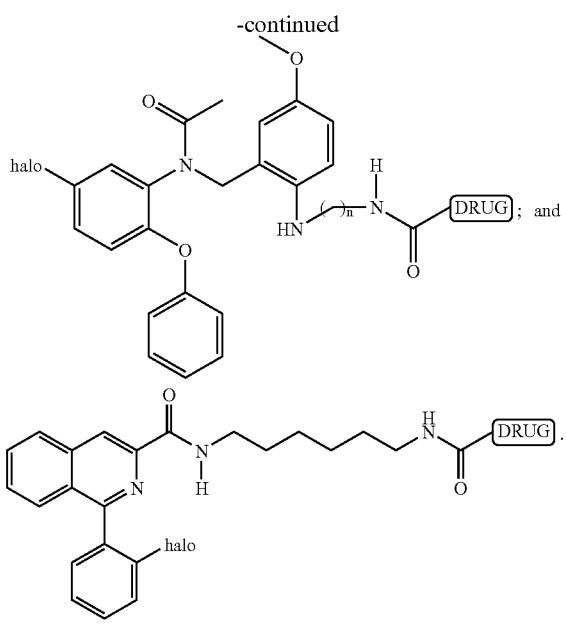

An embodiment of the present invention is a compound of the following formula:

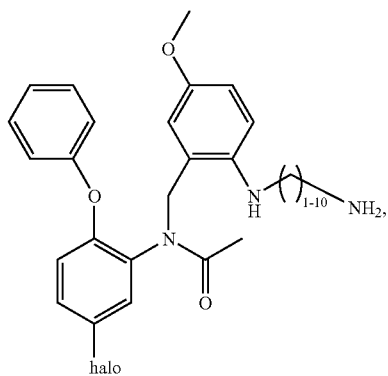

and stereoisomers and conjugable analogs thereof.

In embodiments of the present invention, a chemotherapeutic agent is the "drug." An embodiment of the chemotherapeutic agent is a topoisomerase inhibitor. A topoisomerase inhibitor may be adriamycin, amsacrine, camptothecin, daunorubicin, dactinomycin, doxorubicin, eniposide, epirubicin, etoposide, idarubicin, mitoxantrone, teniposide, or topotecan. Preferably, the topoisomerase inhibitor is etoposide.

The imaging and/or therapeutic agents of the present invention may be administered as determined by one of ordinary skill in the art. In embodiments the agents may be administered as shown in U.S. application Ser. No. 11/181,201, incorporated herein by reference.

That is, compounds of the present invention can be administered orally, parenterally by intravenous injection, transdermally, by pulmonary inhalation, by intravaginal or intrarectal insertion, by subcutaneous implantation, intramuscular injection or by injection directly into an affected tissue, as for example by injection into a tumor site. In some instances the materials may be applied topically at the time surgery is carried out. In another instance the topical administration may be ophthalmic, with direct application of the therapeutic composition to the eye.

The materials are formulated to suit the desired route of administration. The formulation may comprise suitable excipients include pharmaceutically acceptable buffers, stabilizers, local anesthetics, and the like that are well known in the art. For parenteral administration, an exemplary formulation may be a sterile solution or suspension; For oral dosage, a syrup, tablet or palatable solution; for topical application, a lotion, cream, spray or ointment; for administration by inhalation, a microcrystalline powder or a solution suitable for nebulization; for intravaginal or intrarectal administration, pessaries, suppositories, creams or foams. Preferably, the route of administration is parenteral, more preferably intravenous.

In general, an embodiment of the invention is to administer a suitable daily dose of a therapeutic composition that will be the lowest effective dose to produce a therapeutic effect. However, it is understood by one skilled in the art that the dose of the composition to practice the invention will vary depending on the subject and upon the particular route of administration used. It is routine in the art to adjust the dosage to suit the individual subjects. Additionally, the effective amount may be based upon, among other things, the size of the compound, the biodegradability of the compound, the bioactivity of the compound and the bioavailability of the compound. If the compound does not degrade quickly, is bioavailable and highly active, a smaller amount will be required to be effective. The actual dosage suitable for a subject can easily be determined as a routine practice by one skilled in the art, for example a physician or a veterinarian given a general starting point.

The therapeutic treatment may be administered hourly, daily, weekly, monthly, yearly (e.g., in a time release form) or as a one-time delivery. The delivery may be continuous delivery for a period of time, e.g., intravenous delivery. In one embodiment of the methods described herein, the therapeutic composition is administered at least once per day. In one embodiment, the therapeutic composition is administered daily. In one embodiment, the therapeutic composition is administered every other day. In one embodiment, the therapeutic composition is administered every 6 to 8 days. In one embodiment, the therapeutic composition is administered weekly.

In embodiments of the methods described herein, the route of administration can be oral, intraperitoneal, transdermal, subcutaneous, by vascular injection into the tumor, by intravenous or intramuscular injection, by inhalation, topical, intralesional, infusion; liposome-mediated delivery; intrathecal, gingival pocket, rectal, intrabronchial, nasal, transmucosal, intestinal, ocular or otic delivery, or any other methods known in the art as one skilled in the art may easily perceive. In other embodiments of the invention, the compositions incorporate particulate forms protective coatings, hydrolase inhibitors or permeation enhancers for various routes of administration, including parenteral, pulmonary, nasal and oral.

An embodiment of the method of present invention is to administer the compositions described herein in a sustained release form. Such method comprises implanting a sustained-release capsule or a coated implantable medical device so that a therapeutically effective dose is continuously delivered to a subject of such a method. The compositions may be delivered via a capsule which allows sustained-release of the agent or the peptide over a period of time. Controlled or sustained-release compositions include formulation in lipophilic depots (e.g., fatty acids, waxes, oils). Also comprehended by the invention are particulate compositions coated with polymers (e.g., poloxamers or poloxamines).

The method of present invention is effective in treatment of various types of cancers, including but not limited to: pancreatic cancer, renal cell cancer, Kaposi's sarcoma, chronic leukemia (preferably chronic myelogenous leukemia), chronic lymphocytic leukemia, breast cancer, sarcoma, ovarian carcinoma, rectal cancer, throat cancer, melanoma, colon cancer, bladder cancer, lymphoma, mesothelioma, mastocytoma, lung cancer, liver cancer, mammary adenocarcinoma, pharyngeal squamous cell carcinoma, gastrointestinal cancer, stomach cancer, myeloma, prostate cancer, B-cell malignancies or metastatic cancers.

The present invention is also effective against other diseases related to unwanted cell proliferation. Such hyperproliferative diseases include but are not limited to: psoriasis, rheumatoid arthritis, lamellar ichthyosis, epidermolytic hyperkeratosis, restenosis, endometriosis, proliferative retinopathy, lung fibrosis, desmoids or abnormal wound healing.

EXAMPLES

The following examples are presented purely for exemplary purposes, and as such the material in this section should be considered as embodiments of the present invention and not to be limiting thereof.

Example 1

This example demonstrates the conjugation of a NIR dye of the present invention and a conjugable analog or conjugable form of PK11195 for deep tissue imaging. In this example, IRDye800CW (LiCOR) is coupled to conjugable PK11195.

Dye800CW-PK11195 (Scheme 1)—To a 10 mL round bottom flask, about 196.5 μL of a 1 mg/ml conjugable PK11195 solution (DMSO) is mixed with about 300 μL of an about 1 mg/mL Dye800CW (DMSO). The reaction proceeds under nitrogen flow for about 1 hour at RT. Reaction progress is monitored via HPLC and ESI MS.

Scheme 1 - Conjugation of Succinimidyl Dye to conjugable PK11195

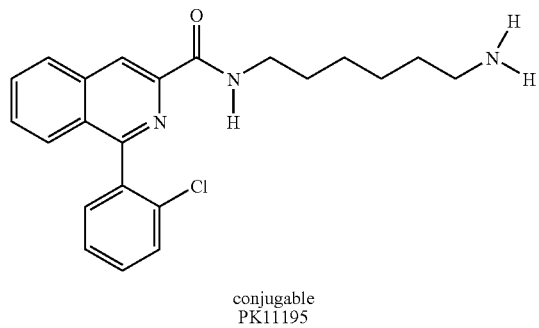

conjugable PK11195

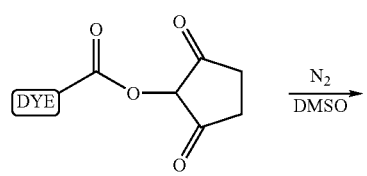

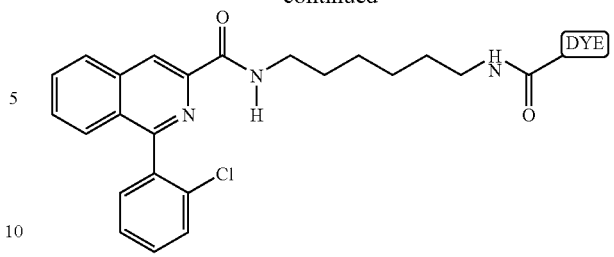

Yield is about 99% and requires no further purification.

Example 2

This example demonstrates an example of the formulation of a NIR-glucosamine conjugate of the present invention.

Dye800CW-glucosamine (Scheme 2)—To a 10 mL round bottom flask, about 9.3 mg sodium methoxide and about 37 mg D-glucosamine hydrochloride are reacted in about 2 mL DMSO. The solution is stirred under nitrogen for about 3 hours at RT. Next, about 3 μL of the resulting solution are mixed with about 150 μL of an about 1 mg/mL Dye800CW/DMSO solution in a separate 10 mL flask. The mixture is stirred under nitrogen for another 1.5 hours at RT.

Scheme 2 - Conjugation of Succinimidyl Dye to glucosamine

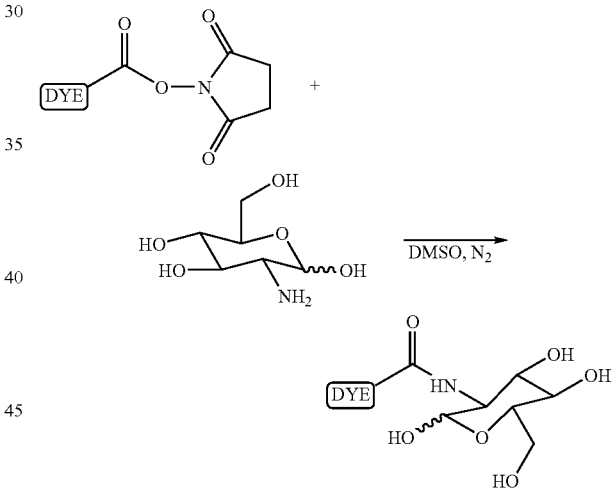

Reaction progress was monitored via HPLC and ESI MS and the reaction yielded 98% pure conjugate.

Example 3

This example demonstrates the use of compounds of the present invention in ESI (Electrospray Ionization) mass spectra.

Initially, about 20 μL of the reaction solution of Example 1 is diluted to about 180 μL using 5 mM ammonium acetate aqueous solution containing about 0.05% acetic acid. The sample is injected the sample immediately into a Mariner ESI mass spectrometer. Some major instrument settings are: spray tip at about 3.4 kv, nozzle potential at about 200 v, quadrupole temperature at about 150° C. and nozzle temperature at about 150° C. Spectra is collected every 100 seconds. In spectrum for Dye800 W-glucosamine complex, the expected molecular peak is observed at 1164Da. In the spectrum for Dye800CW-PK11195 complex, the expected molecular peak is observed at 1365.9Da.

Example 4

This example shows a synthetic pathway yielding a conjugable Ro5-4864 of the present invention, and conjugation to an imaging agent, such as Lanthanide chelate or NIR-dye.

compound in the form of compound 8. The chlorine on the signaling part will react with N—H group in compound 5 to produce the final imaging agent (compound 9). The product can be further chelated by adding lanthanide chloride solution (LnCl$_3$, EuCl$_3$ etc) into product solution with pH 6.5. The synthetic pathway for lanthanide chelate has been reported. See Griffin J M M, Skwierawska A M, Manning H C, Marx J

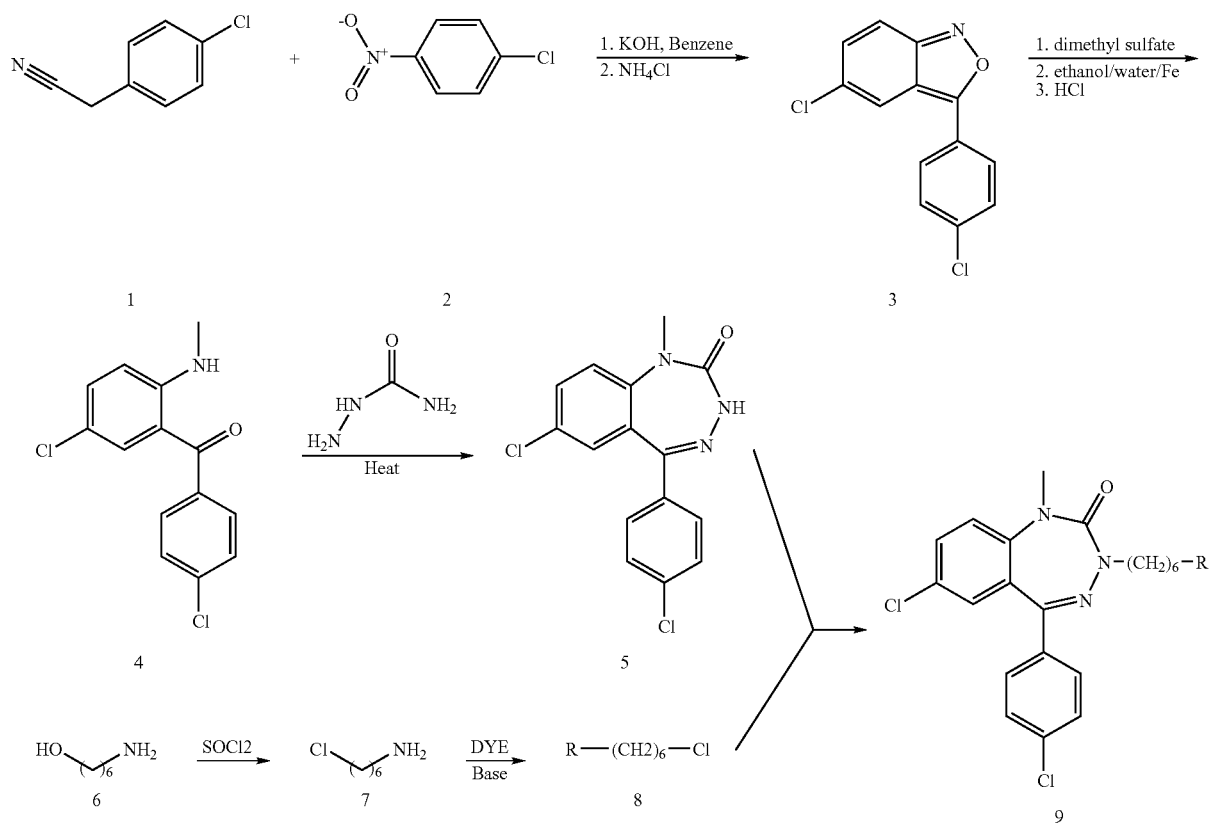

A conjugable form of compounds similar to Ro5-4864 has been previously reported (see U.S. Pat. No. 5,901,381) and a synthetic procedure in Scheme 3 will be used to synthesize a conjugable form of Ro5-4864. A solution of KOH in methanol will be treated with a solution of 4-chlorophenyl-acetonitrile 1 and 4-chloronitro-benzene 2 in benzene. The mixture will be stirred for 3 hours and then poured to ammonium chloride solution. Compound 3 will then precipitate out. Compound 4 will be produced by stirring compound 3 and dimethyl sulfate for 5 hours, followed by being treated with ethanol, water, iron fillings and hydrochloric acid. See Vejdelek Z, Polivka Z, Protiva M. Synthesis of 7-Chloro-5-(4-Chlorophenyl)-1-Methyl-1,3-Dihydro-1,4-Benzodiazepin-2-One. Collection of Czechoslovak Chemical Communications 1985; 50:1064-1069. Compound 4 and semicarbazide, after heated to 210° C., will produce compound 5. Compound 7 will be used as a linker to combine compound 5 and lanthanide chelate/dye800 cw. Compound 7 can be synthesized by the reaction between compound 6 and thionyl chloride. Lanthanide chelate (with carboxylic acid group) or dye800 cw (a N-hydroxysuccinimide ester) can then react with compound 7 in basic solution to produce a N, Bornhop D J. Simple, high yielding synthesis of trifunctional fluorescent lanthanide chelates. Tetrahedron Letters 2001; 42:3823-3825.

Example 5

This Example shows a scheme for the synthesis of a conjugable form of DAA1106 of the present invention, which can then be conjugated to an imaging agent.

Scheme 4 - Synthesis of conjugatable DAA1106

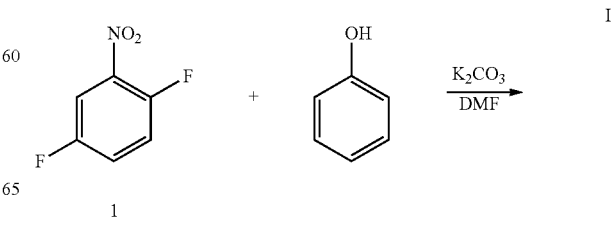

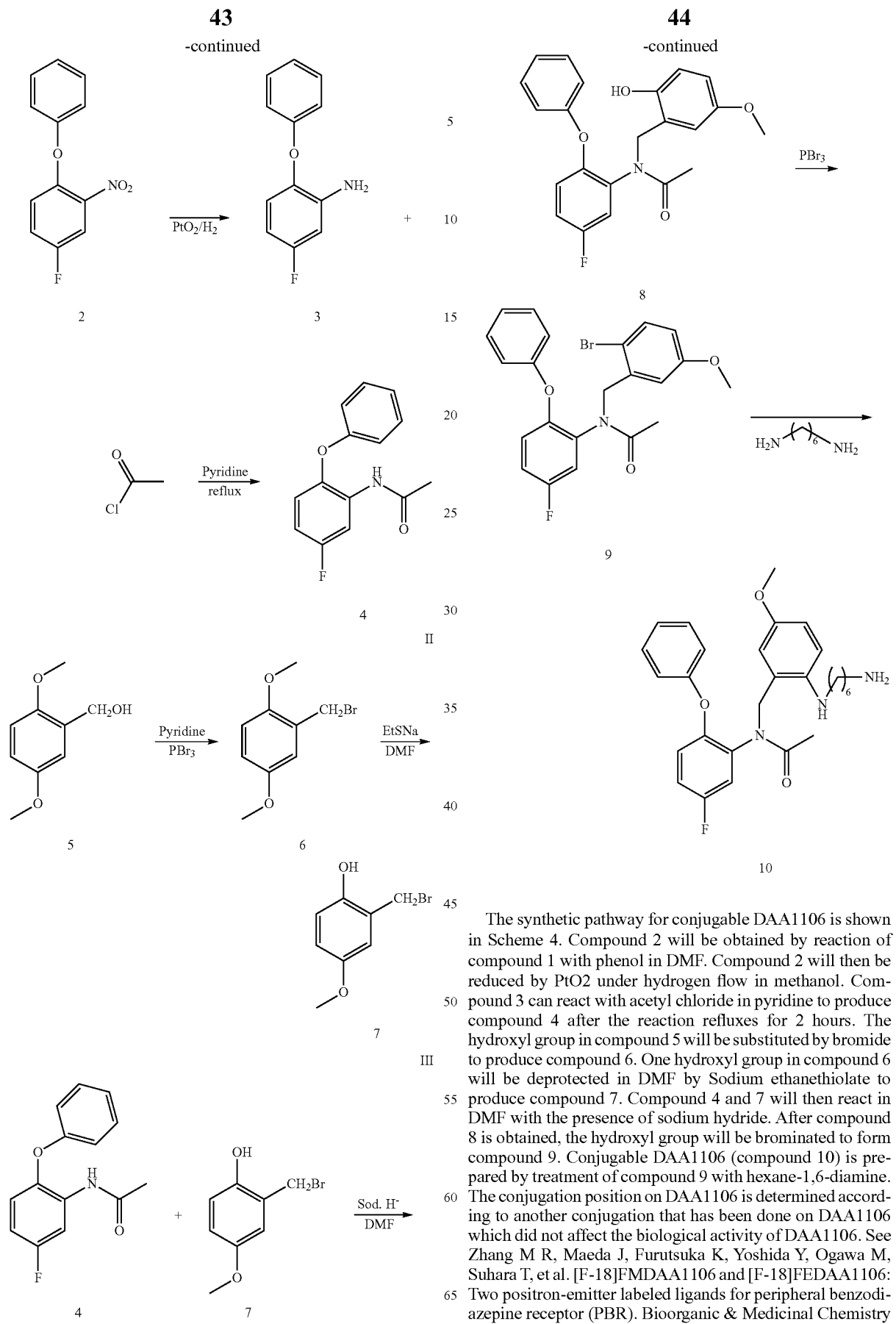

The synthetic pathway for conjugable DAA1106 is shown in Scheme 4. Compound 2 will be obtained by reaction of compound 1 with phenol in DMF. Compound 2 will then be reduced by PtO2 under hydrogen flow in methanol. Compound 3 can react with acetyl chloride in pyridine to produce compound 4 after the reaction refluxes for 2 hours. The hydroxyl group in compound 5 will be substituted by bromide to produce compound 6. One hydroxyl group in compound 6 will be deprotected in DMF by Sodium ethanethiolate to produce compound 7. Compound 4 and 7 will then react in DMF with the presence of sodium hydride. After compound 8 is obtained, the hydroxyl group will be brominated to form compound 9. Conjugable DAA1106 (compound 10) is prepared by treatment of compound 9 with hexane-1,6-diamine. The conjugation position on DAA1106 is determined according to another conjugation that has been done on DAA1106 which did not affect the biological activity of DAA1106. See Zhang M R, Maeda J, Furutsuka K, Yoshida Y, Ogawa M, Suhara T, et al. [F-18]FMDAA1106 and [F-18]FEDAA1106: Two positron-emitter labeled ligands for peripheral benzodiazepine receptor (PBR). Bioorganic & Medicinal Chemistry Letters 2003; 13:201-204. The product should be conjugable to lanthanide chelator in water/DMF/dioxane/TEA mixture. The conjugate will be further chelated by adding Lanthanide chloride solution (LnCl₃, EuCl₃ etc) into pH 6.5 product solution.

Example 6

This example shows an example of the synthesis, characterization, and preliminary cell study for an embodiment of the present invention, a dye800 cw-DAA1106 conjugation, as well as the conjugation of the PBR ligand DAA1106 to a NIR dye, followed by cell uptake.

In this example, dye800CW (5 mg, 4.3 µmol) and conjugable DAA1106 (5 mg, 10 µmol) is mixed in DMSO (1 mL) in a 10 mL round bottom flask. The solution is stirred under argon flow for 10 hours. The reaction scheme is shown in Scheme 5, below. Product is purified through neutral alumina column using 0.1 M triethyl ammonium acetate in 80/20 acetonitrile/water solution.

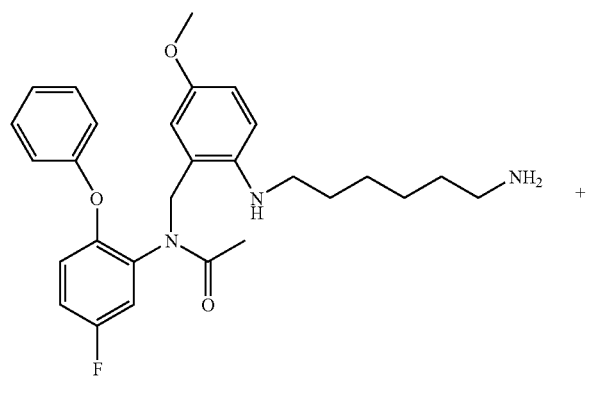

Scheme 5. Reaction scheme for dye800CW-DAA1106

Upon preparing dye800CW-DAA1106, absorption and emission spectra (Table 1) are obtained at room temperature with a Shimadzu 1700 UV-vis spectrophotometer and ISS PCI spectrofluorometer respectively. The same sample (2 µM) is used for taking both UV and fluorescence spectrum. UV spectrum was scanned from 190 nm to 900 nm with sampling rate of 1 nm. Cuvette path length was 1 cm. Fluorescence sample was excited at 797 nm. Spectrum was collected from 700 nm to 900 nm with scan rate 1 nm/second. Slit width was set to 1.5. Photo multiplier tube (PMT) voltage was at 75 watts. Dye800CW-DAA1106 has maximum absorption at 779 nm and fluorescence at 801 nm in methanol.

Regarding cell uptake, C6 glioma cell lines are a widely used cell line in neurobiological research that has high PBR expression. C6 cells were incubated with 10 µM dye800CW-DAA1106 in culture media for half hour and then rinsed and re-incubated with saline before imaging. FIG. 1 shows white light and fluorescence pictures of dosed and un-dosed cells. Instrument used is Nikon epifluorescence microscope equipped with Ludl Qimaging camera, Nikon S fluor 20x/0.75 objective, mercury lamp and ICG filter set. Picture B shows cell take-up of dye800CW-DAA1106, while un-dosed cell (picture D) does not show any significant fluorescence.

Example 7

This example shows the synthesis, characterization and preliminary cell study of a lissamine-DAA1106 conjugation. An example of a lissamine dye has a molar extinction coefficient of 88,000 cm$^{-1}$M$^{-1}$ and good quantum efficient of about 95%. It absorbs at 568 nm and emits at 583 nm (in methanol) with a decent stokes shift and thus bright fluorescence.

Lissamine rhodamine B sulfonyl chloride (4 mg, 6.9 µmol), conjugable DAA1106 (5 mg, 10 µmol) and tri-ethylamine (10 µL) was mixed in dichloromethane (0.8 mL) in a 10 mL round bottom flask. The solution was stirred under argon flow for 3 hours. The reaction scheme is shown in Scheme 6. Product was purified through column chromatography (silica gel) using 19/1 dichloromethane/methanol solution.

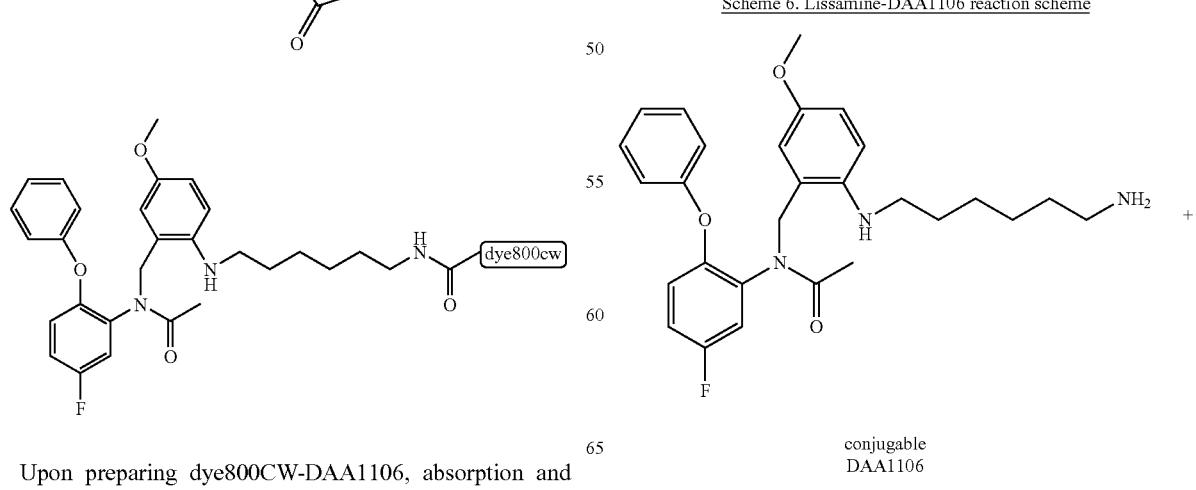

Scheme 6. Lissamine-DAA1106 reaction scheme

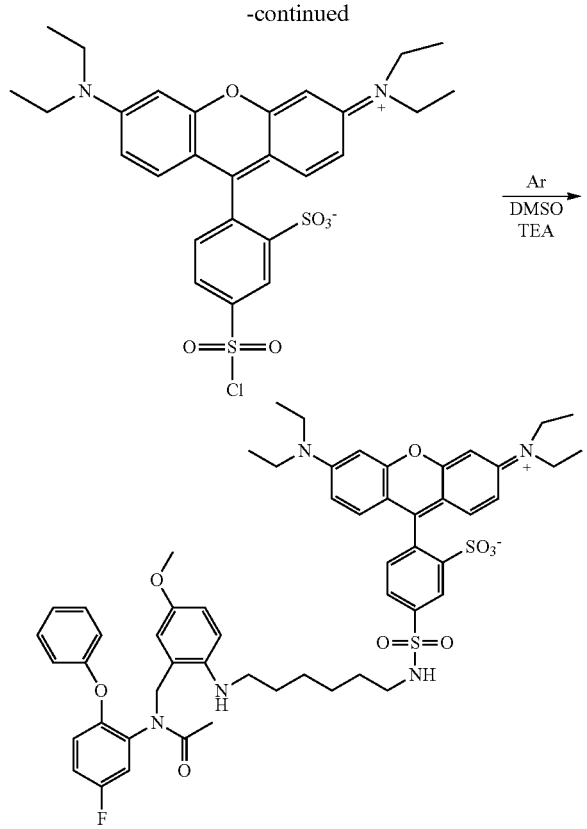

Upon preparing dye800CW-DAA1106, absorption and emission spectra (Table 1) are obtained at room temperature with a Shimadzu 1700 UV-vis spectrophotometer and ISS PCI spectrofluorometer respectively. The same sample (2 μM) is used for taking both UV and fluorescence spectrum. UV spectrum was scanned from 190 nm to 900 nm with sampling rate of 1 nm. Cuvette path length was 1 cm. Fluorescence sample was excited at 797 nm. Spectrum was collected from 700 nm to 900 nm with scan rate 1 nm/second. Slit width was set to 1.5. Photo multiplier tube (PMT) voltage was at 75 watts. Dye800CW-DAA1106has maximum absorption at 779 nm and fluorescence at 801 nm in methanol.

C6 cells were incubated with 10 μM lissamine-DAA1106 in culture media for half hour and then rinsed and re-incubated with saline before imaging. FIG. 2 shows white light and fluorescence pictures of dosed and un-dosed cells. Instrument used was Nikon epifluorescence microscope equipped with Ludl Qimaging camera, Nikon S fluor 20x/0.75 objective, mercury lamp and Texas red filter set. Picture B shows cell take-up of lissamine-DAA1106 at perinuclear location. This observation was expected since PBR is a mitochondrial protein. Un-dosed cells (picture D) exhibited no fluorescence.

Example 8

This example shows an example of a synthetic pathway yielding a conjugable form of a SSR180575 compound of the present invention.

Starting from m-chloroaniline, which was diazotised and coupled with ethyl α-methylacetoacetate, the azo-ester was converted into ethyl pyruvate m-chlorophenylhydrazone 1 (the Japp-Klingeman reaction). Polyphosphoric acid facilitated the conversion to molecule 2. Next, N-methylation with dimethylcarbonate in presence $K_2CO_3$ yielded the ester 3 and was treated with hydrazine and converted into hydrazide 4. The ring was closed in the presence of $POCl_3$ and compound 5 was obtained. N-phenylation with using PhI and CuI (as catalyst) provide compound 6. Mild hydrolysis with dilute KOH in EtOH yield acid 7. To conjugated mono-N—BOC protected N-methyl-1,6-hexanediamine to 7 used BOP. Removal of protecting group with TFA in $CH_2Cl_2$ is yields 8.

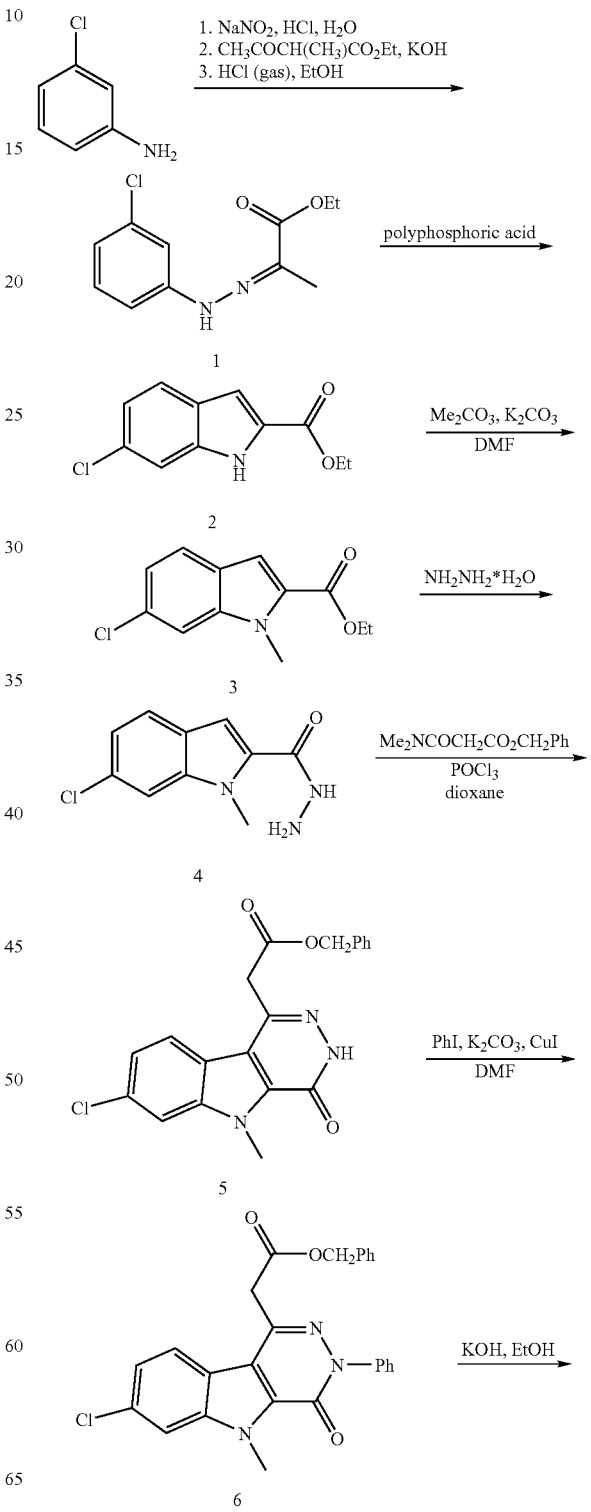

-continued

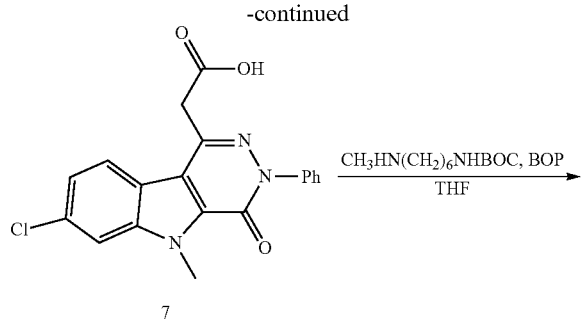

Example 9

Example 9 demonstrates specific, in vivo tumor labeling using a method of the present invention. A NIR-PK 11195 deep tissue imaging agent was made as shown in Example 1. Tumor bearing Smad3 gene knockout mice and control animals were injected with 10 nmoles of the imaging agent and imaged about 14 hours following injection. Specific labeling was observed in the abdominal region of tumor animals and clearance in the control animals. This selective uptake is shown in FIG. 3. A post-imaging autopsy confirmed localization of the imaging agent in the SMAD3 animal.

Example 10

This Example shows NIR-PK 11195 imaging in connection with neurodegenerative processes in experimental autoimmune encephalomyelitis (EAE), the animal model of multiple sclerosis. Additionally, this Example shows the use of the present invention to monitor the progression of a disease state. A conjugated imaging agent NIR-PK 11195 was made in accordance with Example 1. An EAE induced and control animals were injected with NIR-PK 11195 and imaged. EAE animals demonstrate strong fluorescence along the spinal column indicating activated T cell and macrophage response which signal the onset of the demylenation processes characteristic to EAE. The EAE/treated mouse was treated with a curcumin composition.

FIG. 3 shows images associated with this example that confirm insignificant uptake of the imaging agent in the control, but indicate full onset of a disease state in the EAE mice. Subsequent imaging shows the progression of the disease after a disease state treatment is administered.

Example 11

Example 11 shows a synthetic synthetic pathway of etoposide-C6DAA1106 is shown below:

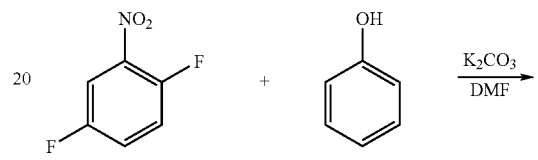

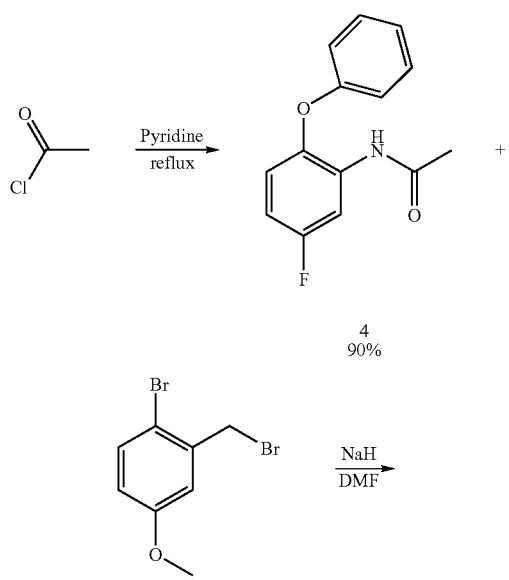

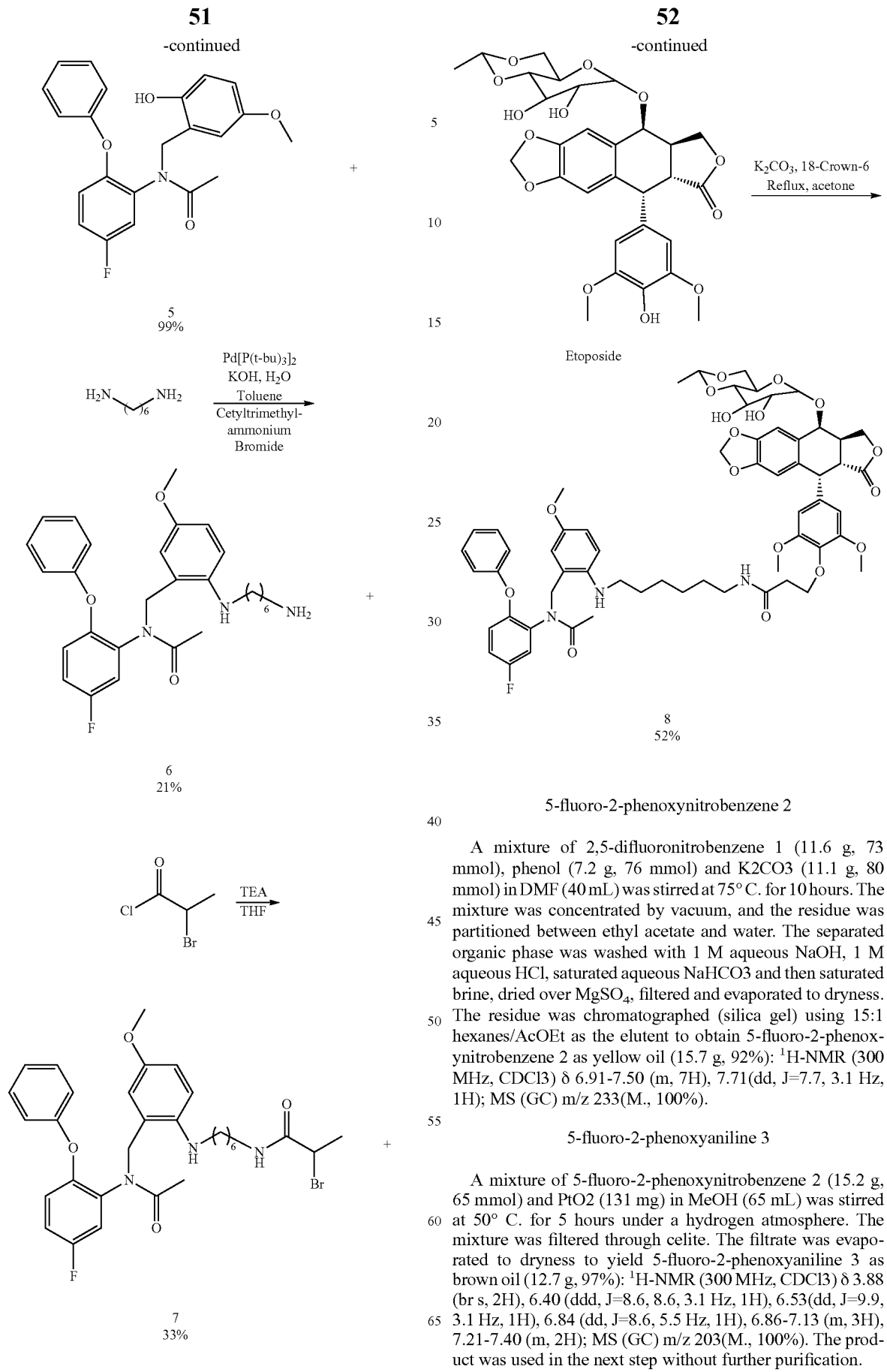

5-fluoro-2-phenoxynitrobenzene 2

A mixture of 2,5-difluoronitrobenzene 1 (11.6 g, 73 mmol), phenol (7.2 g, 76 mmol) and K2CO3 (11.1 g, 80 mmol) in DMF (40 mL) was stirred at 75° C. for 10 hours. The mixture was concentrated by vacuum, and the residue was partitioned between ethyl acetate and water. The separated organic phase was washed with 1 M aqueous NaOH, 1 M aqueous HCl, saturated aqueous NaHCO3 and then saturated brine, dried over $MgSO_4$, filtered and evaporated to dryness. The residue was chromatographed (silica gel) using 15:1 hexanes/AcOEt as the elutent to obtain 5-fluoro-2-phenoxynitrobenzene 2 as yellow oil (15.7 g, 92%): $^1$H-NMR (300 MHz, CDCl3) δ 6.91-7.50 (m, 7H), 7.71(dd, J=7.7, 3.1 Hz, 1H); MS (GC) m/z 233(M., 100%).

5-fluoro-2-phenoxyaniline 3

A mixture of 5-fluoro-2-phenoxynitrobenzene 2 (15.2 g, 65 mmol) and PtO2 (131 mg) in MeOH (65 mL) was stirred at 50° C. for 5 hours under a hydrogen atmosphere. The mixture was filtered through celite. The filtrate was evaporated to dryness to yield 5-fluoro-2-phenoxyaniline 3 as brown oil (12.7 g, 97%): $^1$H-NMR (300 MHz, CDCl3) δ 3.88 (br s, 2H), 6.40 (ddd, J=8.6, 8.6, 3.1 Hz, 1H), 6.53(dd, J=9.9, 3.1 Hz, 1H), 6.84 (dd, J=8.6, 5.5 Hz, 1H), 6.86-7.13 (m, 3H), 7.21-7.40 (m, 2H); MS (GC) m/z 203(M., 100%). The product was used in the next step without further purification.

N-(5-fluoro-2-phenoxyphenyl)acetamide 4

5-fluoro-2-phenoxyaniline 3 (5.14 g, 25 mmol) was dissolved in pyridine (15 mL) in a dry flask. At 0° C., acetyl chloride (2.3 mL, 33 mmol) was slowly added to the reaction, which was then refluxed for one hour, and subsequently, concentrated by vacuum. The residue was purified via column chromatography (silica gel) using CHCl3 as the eluent to give N-(5-fluoro-2-phenoxyphenyl)acetamide 4 as white solid (5.6 g, 90%): $^1$H-NMR (300 MHz, CDCl3) δ 8.29 (dd, J=10.5, 3.0 Hz, 1H), 7.74 (br s, 1H), 7.36 (t, J=7.5 Hz, 2H), 7.15 (t, J=7.5 Hz, 1H), 6.98 (d, J=7.5 Hz, 2H), 6.81 (2d, J=5.4, 5.1 Hz, 1H), 6.70 (2 dd, J1=J2=J3=J4=3 Hz, 1H), 2.17 (s, 3H). MS (GC) m/z 245(M., 100%)

N-(2-bromo-5-methoxybenzyl)-N-(5-fluoro-2-phenoxphenyl)acetamide 5

To a dry round bottom flask, was added dry DMF (10 mL) and sodium hydride (100 mg), followed by N-(5-fluoro-2-phenoxyphenyl)acetamide 4 (1.08 g, 4.4 mmol). After the solution was stirred for 15 minutes, 2-bromo-5-methoxybenzyl bromide (1.4 g, 5.0 mmol) was added. After 30 minutes, the reaction was added to stirring water chilled to 0° C. (60 mL). The mixture was extracted by dichloromethane three times. The organic solutions were combined, dried over $Mg_2SO_4$ and then evaporated to dryness. The residue was chromatographed (silica gel) using 1:3 Ethyl acetate/hexanes as the eluent to yield N-(2-bromo-5-methoxybenzyl)-N-(5-fluoro-2-phenoxphenyl)acetamide 5 as yellow oil (1.94 g, 99%). $^1$H-NMR (300 MHz, CDCl3) δ 7.29-7.33 (m, 3H), 7.12 (t, J=7.6 Hz, 1H), 7.02 (d, J=3.2 Hz, 1H), 6.80-6.96 (m, 5H), 6.62 (dd, J=8.4, 2.8 Hz, 1H), 4.96 (dd, J=178, 15.2 Hz, 2H), 3.66 (s, 3H), 2.00 (s, 3H). MS (ESI)+ m/z 442.8([MH]+, 100%), 444.8 ([MH]+, 100%).

C6DAA1106 6

N-(2-bromo-5-methoxybenzyl)-N-(5-fluoro-2-phenoxphenyl)acetamide 5 (202 mg, 0.45 mmol), Pd[P(t-Bu)3]2 (4.6 mg, 9 μmol), hexamethylenediamine (158.4 mg. 1.36 mmol), potassium hydroxide (38.2 mg, 0.68 mmol), cetyltrimethylammonium bromide (1.6 mg, 4.4 μmol), water (12.2 μL, 0.68 mmol) and 800 μL dry toluene were placed in a round bottom flask flushed with argon. The flask was sealed with a septum and the reaction mixture was stirred vigorously at 90° C. for three hours. The reaction was then concentrated by vacuum and purified by column chromatography using 9:1:0.1 $CH_2Cl_2/CH_3OH/NH_3.H_2O$ to yield C6DAA1106 as colorless oil (45.4 mg, 21%). $^1$H-NMR (300 MHz, CDCl3) δ 7.28 (t, J=8.1 Hz, 2H), 7.10 (t, J=7.5 Hz, 1H), 6.91-6.95 (m, 1H), 6.79-6.84 (m, 1H), 6.70-6.75 (4H, m), 6.40 (d, J=8.7 Hz), 6.20 (1H, d, J=3 Hz, 1H), 4.76 (AX, J=14.7 Hz, ??=95.1 Hz, 2H), 3.61 (3H, s), 2.87-3.03 (2H, m, 2H), 2.69 (2H, J=6.9 Hz, 2H), 1.94 (3H), 1.54-1.61 (m, 2H), 1.28-0.48 (m, 8H). MS (ESI)+ m/z 480.2 ([MH]+, 100%).

2-bromo-N-(6-(2-((N-(5-fluoro-2-phenoxyphenyl)acetamido)methyl)-4-methoxyphenylamino)hexyl)propanamide 7

A solution of C6DAA1106 6 (48 mg, 0.1 mmol) and TEA (14.5 μL, 0.1 mmol) in dry THF (4 mL) was cooled by dry ice/acetone. 2-bromo-propionyl chloride (10.1 μL, 0.1 mmol) was then added and the resultant mixture was allowed to stir for 10 minutes. Triethyl ammonium chloride salt was filtered through filter paper. Solvent was removed by vacuum and the product was purified by silica gel column chromatography using methylene chloride/methanol 32/1 as eluent to give 2-bromo-N-(6-(2-((N-(5-fluoro-2-phenoxyphenyl)acetamido)methyl)-4-methoxyphenylamino)hexyl)propanamide 2 as colorless oil (20 mg, 33%). 1H NMR 300 MHz (CDCl3) δ 7.30-7.26 (m, 2H), 7.10 (t, J=7.5 Hz, 1H), 6.97-6.91 (m, 1H), 6.84-6.79 (m, 1H), 6.77-6.68 (m, 4H), 6.40 (d, J=8.7 Hz, 1H), 6.19 (d, J=2.7 Hz, 1H), 4.93-4.86 (m, 1H), 4.66-4.59 (m, 1H), 4.41 (q, J=10.5, 3.6 Hz, 1H), 3.60 (s, 3H), 3.27 (q, J=9.8, 3.2 Hz, 2H), 3.02-2.88 (m, 2H), 1.95 (s, 3H), 1.86 (d, J=6.9 Hz, 3H), 1.64-1.50 (m, 4H), 1.47-1.31 (m, 4H). MS (ESI) m/z 614.6 Da [M+H] (100%) 616.7 Da [M+H] (100%)

Etoposide-C6DAA1106 8

A mixture of etoposide (12 mg, 20 μmol), K2CO3 (4 mg, 30 μmol) and 18-crown-6 (1 mg, 4 μmol) in dry acetone (1 mL) was stirred for 5 minutes under room temperature. A solution of 7 (6 mg, 10 μmol) in dry acetone (300 μL) was added to the mixture and the reaction was heated to reflux with vigorous stirring. After 6 hours, the reaction was allowed to cool down to room temperature and the solvent was removed by vacuum. The residue was partitioned between water and dichloromethane. Extracted with dichloromethane three times. The organic layers were combined, dried over sodium sulfate and concentrated by vacuum. The residue was purified by silica gel column chromatography using 3% methanol in dichloromethane as eluent to give etoposide-C6DAA1106 8 as colorless oil (5.7 mg, 52%). 1H NMR 300 MHz (CDCl3) δ 7.81 (m, 1H), 7.28 (t, J=7.2 Hz, 1H), 7.10 (t, J=7.2 Hz, 1H), 6.95-6.92 (m, 1H), 6.83-6.69 (m, 6H), 6.45 (d, J=3.2 Hz, 2H), 6.41-6.38 (m, 2H), 6.19 (t, J=2.4 Hz, 1H), 5.96-5.94 (m, 2H), 4.94-4.85 (m, 3H), 4.73-4.47 (m, 5H), 4.25-4.23 (m, 1H), 4.18-4.14 (m, 1H), 3.93 (t, J=6.8 Hz, 1H), 3.81 (s, 6H), 3.60 (s, 3H), 3.58-3.56 (m, 2H), 3.44 (t, J=9.2 Hz, 1H), 3.35-3.26 (m, 3H), 3.18-3.13 (m, 2H), 3.00-2.89 (m, 4H), 1.94-1.92 (m, 3H), 1.62-1.52 (m, 11H), 1.42-1.35 (m, 8H). MS (ESI) m/z 1122.7 Da [M+H] (100%).

In other examples of the present invention, the following conjugable DAA 1106 compounds were made:

$C_3$DAA1106 (conjugable DAA1106 with three carbon linker)(Y=8.7%)

$C_4$DAA1106 (Y=7.9%)

$C_5$DAA1106 (Y=10%)

$^1$H-NMR (400 MHz, CDCl$_3$) δ 7.27 (t, J=8.4 Hz, 2H), 7.09 (t, J=7.6 Hz, 1H), 6.91-6.96 (m, 1H), 6.79-6.83 (m, 1H), 6.69-6.75 (m, 4H), 6.39 (d, J=8.8 Hz, 1H), 6.19 (d, J=2.8 Hz, 1H), 4.75 (AX, J=9.6 Hz, Δv=79.2 Hz, 2H), 3.60 (s, 3H), 2.86-3.03 (m, 2H), 2.77 (t, J=5.1 Hz, 2H), 1.94 (s, 3H), 1.50-1.62 (m, 4H), 1.40-1.45 (m, 2H). MS (ESI)$^+$ m/z 466.3 ([MH]$^+$, 100%)

$C_6$DAA1106 (Y=33%)

$^1$H-NMR (300 MHz, CDCl$_3$) δ 7.28 (t, J=8.1 Hz, 2H), 7.10 (t, J=7.5 Hz, 1H), 6.91-6.95 (m, 1H), 6.79-6.84 (m, 1H), 6.70-6.75 (m, 4H), 6.40 (d, J=8.7 Hz, 1H), 6.20 (d, J=3 Hz, 1H), 4.76 (AX, J=14.7 Hz, Δv=95.1 Hz, 2H), 3.61 (s, 3H), 2.87-3.03 (m, 2H), 2.66 (t, J=6.9 Hz, 2H), 1.94 (s, 3H), 1.54-1.61 (m, 2H), 1.28-0.48 (m, 8H). MS (ESI)$^+$ m/z 480.2 ([MH]$^+$, 100%)

$C_7$DAA1106 (Y=12%)

$^1$H-NMR (300 MHz, CDCl$_3$) δ 7.28 (t, J=7.5 Hz2H), 7.10 (t, J=7.5 Hz, 1H), 6.91-6.98 (m, 1H), 6.80-6.85 (m, 1H), 6.70-6.75 (m, 4H), 6.41 (d, J=9.0 Hz, 1H), 6.20 (d, J=3.0 Hz, 1H), 4.76 (AX, J=14.7 Hz, Δv=103.2 Hz, 2H), 3.60 (s, 3H), 2.84-3.06 (m, 2H), 2.68 (t, J=7.2 Hz, 2H), 1.94 (s, 3H), 1.53-1.60 (m, 2H), 1.31-1.46(m, 12H). (ESI)$^+$ m/z 494.3 ([MH]$^+$, 100%)

$C_8$DAA1106 (Y=5.8%)

¹H-NMR (400 MHz, CDCl₃) δ 7.28 (t, J=8.4 Hz, 2H), 7.10 (t, J=7.6 Hz, 1H), 6.92-6.97 (m, 1H), 6.81-6.84 (m, 1H), 6.71-6.74 (m, 4H), 6.41 (d, J=8.8 Hz, 1H), 6.20 (d, J=2.8 Hz, 1H), 4.76 (AX, J=14.4 Hz, Δv=140.4 Hz, 2H), 3.60 (s, 3H), 2.85-3.04 (m, 2H), 2.72 (t, J=7.2 Hz, 2H), 1.94 (s, 3H), 1.44-1.59 (m, 6H), 1.30-1.37(m, 10H). (ESI)⁺ m/z 508.3 ([MH]⁺, 100%)

$C_9$DAA1106 (Y=11%)
¹H-NMR (300 MHz, CDCl₃) δ 7.29 (t, J=7.5 Hz, 2H), 7.10 (t, J=7.5 Hz, 1H), 6.92-6.97 (m, 1H), 6.80-6.85 (m, 1H), 6.71-6.75 (m, 4H), 6.41 (d, J=9.0 Hz, 1H), 6.20 (d, J=3.0 Hz, 1H), 4.76 (AX, J=14.4 Hz, Δv=105.3 Hz, 2H), 3.61 (s, 3H), 2.84-3.06 (m, 2H), 2.72 (t, J=6.9 Hz, 2H), 2.51 (s, 2H), 1.94 (s, 3H), 1.45-1.62 (m, 5H), 1.19-1.36(m, 10H). (ESI)⁺ m/z 522.3 ([MH]⁺, 100%)

General Method for Conjugable DAA1106 Amide (4) Synthesis

A mixture of acetic acid (1.6 μL, 27.5 μmol), triethyl amine (TEA) (50 μL) and 2-Succinimido-1,1,3,3,-tetramethyluronium tetrafluoroborate (TSTU) (8.3 mg, 27.5 μmol) in dry methylene chloride (1 mL) was stirred at room temperature under argon for three hours. A solution of conjugable DAA1106 (25 μmol) in anhydrous methylene chloride (1 mL) was added to the mixture and the resulting mixture was stirred for another two and half hours. Reaction solution was then concentrated by vacuum rotary evaporation and the product was purified via silica gel column chromatography using 3% methanol in methylene chloride as eluent. Conjugable DAA1106 amide was collected as a colorless oil.

$C_3$DAA1106 Amide
¹H-NMR (300 MHz, CDCl₃) δ 7.27 (t, J=7.5 Hz, 2H), 7.10 (t, J=7.2 Hz, 1H), 6.71-6.84 (m, 3H), 6.63 (d, J=7.5 Hz, 2H), 6.40 (d, J=8.7 Hz, 1H), 6.19 (d, J=2.7 Hz, 1H), 6.04 (br s, 1H), 5.12 (br s, 1H), 4.77 (AX, J=14.4 Hz, Δv=36.9 Hz, 2H), 3.61 (s, 3H), 3.29 (q, J=6.3 Hz, 2H), 2.94-3.13 (m, 2H), 1.97 (br s, 6H), 1.75-1.79 (m, 2H), 1.67 (br s, 1H). MS (ESI)⁺ m/z 502.1 ([MNa]⁺, 100%)

$C_4$DAA1106 Amide
¹H-NMR (300 MHz, CDCl₃) δ 7.27 (t, J=7.5 Hz, 2H), 7.10 (t, J=7.2 Hz, 1H), 6.92-6.99 (m, 1H), 6.65-6.84 (m, 5H), 6.56 (br s, 1H), 6.34 (d, J=8.7H, z1H), 6.20 (d, J=3.0 Hz, 1H), 4.78 (AX, J=14.7 Hz, Δv=36.0 Hz, 2H), 3.61 (s, 3H), 3.28 (2H, m), 2.81-3.05 (m, 2H), 2.01 (s, 3H), 1.96 (s, 3H), 1.63-1.68 (m, 4H). MS (ESI)⁺ m/z 494.2 ([MH]⁺, 100%)

$C_5$DAA1106 Amide
¹H-NMR (300 MHz, CDCl₃) δ 7.28 (t, J=7.5 Hz, 2H), 7.10 (t, J=7.5 Hz, 1H), 6.92-6.99 (m, 1H), 6.80-6.85 (m, 1H), 6.68-6.76 (m, 4H), 6.47 (br s, 1H), 6.39 (d, J=8.7 Hz, 1H), 6.20 (d, J=3.0 Hz, 1H), 4.81 (br s, 1H), 4.78 (AX, J=14.4 Hz, Δv=73.5 Hz, 2H), 3.61 (s, 3H), 3.28 (q, J=6.0 Hz, 2H), 2.82-3.08 (m, 2H), 1.95 (s, 3H), 1.95 (s, 3H), 1.44-1.65 (m, 7H).MS (ESI)⁺ m/z 508.2 ([MH]⁺, 100%)

$C_6$DAA1106 Amide
¹H-NMR (400 MHz, CDCl₃) δ 7.28 (t, J=7.6 Hz, 2H), 7.10 (t, J=7.2 Hz, 1H), 6.92-6.97 (m, 1H), 6.80-6.84 (m, 1H), 6.70-6.75 (m, 4H), 6.40 (d, J=8.8 Hz, 1H), 6.19 (d, J=2.8 Hz, 1H), 5.90 (br s, 1H), 4.87 (br s, 1H), 4.76 (AX, J=14.4 Hz, Δv=114.0 Hz, 2H), 3.60 (s, 3H), 3.24 (q, J=6.0 Hz, 2H), 2.86-3.06 (m, 2H), 1.97 (s, 3H), 1.94 (s, 3H), 1.48-1.59 (m, 4H), 1.33-1.41 (m, 4H).MS (ESI)⁺ m/z 522.2 ([MH]⁺, 100%)

$C_7$DAA1106 Amide
¹H-NMR (300 MHz, CDCl₃) δ 7.28 (t, J=7.5 Hz, 2H), 7.10 (t, J=7.2 Hz, 1H), 6.92-6.98 (m, 1H), 6.80-6.85 (m, 1H), 6.70-6.75 (m, 4H), 6.40 (d, J=8.7 Hz, 1H), 6.19 (d, J=2.7 Hz, 1H), 5.64 (br s, 1H), 4.87 (br s, 1H), 4.76 (AX, J=14.4 Hz, Δv=100.2 Hz, 2H), 3.60 (s, 3H), 3.23 (q, J=6.0 Hz, 2H), 2.86-3.03 (m, 2H), 1.96 (s, 3H), 1.94 (s, 3H), 1.45-1.60 (m, 4H), 1.31-1.36 (m, 6H). MS (ESI)⁺ m/z 536.4 ([MH]⁺, 100%)

$C_8$DAA1106 Amide
¹H-NMR (300 MHz, CDCl₃) δ 7.29 (t, J=7.5 Hz, 2H), 7.10 (t, J=7.2 Hz, 1H), 6.91-6.98 (m, 1H), 6.80-6.85 (m, 1H), 6.70-6.74 (m, 4H), 6.41 (d, J=8.7 Hz, 1H), 6.20 (d, J=3.0 Hz, 1H), 5.60 (br s, 1H), 4.86 (br s, 1H), 4.76 (AX, J=14.4 Hz, Δv=113.1 Hz, 2H), 3.61 (s, 3H), 3.23 (q, J=6.0 Hz, 2H), 2.84-3.06 (m, 2H), 1.96 (s, 3H), 1.94 (s, 3H), 1.46-1.59 (m, 4H), 1.31-1.37 (m, 8H). MS (ESI)⁺ m/z 550.5 ([MH]⁺, 100%)

$C_9$DAA1106 Amide
¹H-NMR (300 MHz, CDCl₃) δ 7.29 (t, J=7.5 Hz, 2H), 7.10 (t, J=7.2 Hz, 1H), 6.91-6.98 (m, 1H), 6.80-6.85 (m, 1H), 6.70-6.74 (m, 4H), 6.41 (d, J=9.0 Hz, 1H), 6.20 (d, J=3.0 Hz, 1H), 5.31 (br s, 1H), 4.86 (br s, 1H), 4.76 (AX, J=14.4 Hz, Δv=110.1 Hz, 2H), 3.61 (s, 3H), 3.23 (q, J=6.0 Hz, 2H), 2.84-3.05 (m, 2H), 1.97 (s, 3H), 1.94 (s, 3H), 1.46-1.59 (m, 4H), 1.31-1.37 (m, 10H). MS (ESI)⁺ m/z 564.5 ([MH]⁺, 100%)

IRDye™ 800CW-$C_6$DAA1106 (NIRDAA)

IRDye™ 800CW NHS ester (3 mg, 2.6 μmol) and $C_6$DAA1106 (3 mg, 6.3 μmol) were mixed in DMSO (7 mL) in a round bottom flask and stirred under argon flow for 1 hour. HPLC analysis was performed on a Varian Polaris C-18 column (250×4.6 mm) at a flow rate of 0.8 mL/min. Flow A was 0.1% TEA in water and flow B was 0.1% TEA in acetonitrile. The elution method for analytical HPLC started with a linear gradient from 100% to 70% A over 20 minutes, continued to 50% A over 5 minutes, arrived at 20% A in another 10 minutes, held at 20% A for 3 min, and finally returned to 100% A over 1 minute. The elution profile was monitored by UV absorbance at 254 and 780 nm. Product was purified by preparative HPLC using a Varian Polaris C-18 column (250×21.2 mm) at 10 mL/min. Acetonitrile in the desired fraction was removed by vacuum and the aqueous solution was loaded on an ion exchange column loaded with Amberlite IR-120 plus ion exchange resin (Sodium form). The collected solution was concentrated by vacuum rotary evapotation, frozen to −78° C. and dried under freeze-dry system. NIRDAA was collected as a dark green solid (1.2 mg, 31%). 1H NMR 500 MHz (MeOD) 7.99-7.91 (m, 3H), 7.86-7.78 (m, 6H), 7.34 (d, J=8.0 Hz, 1H), 7.27-7.23 (m, 3H), 7.17 (d, J=8.5 Hz, 1H), 7.10-7.01 (m, 3H), 6.77-6.74 (m, 1H), 6.70 (dd, J=9.0, 3.0 Hz, 1H), 6.59 (d, J=8.5 Hz, 2H), 6.42 (d, J=9.0 Hz, 1H), 6.26 (d, J=14.0 Hz, 1H), 6.20 (d, J=3.0 Hz, 1H), 6.15 (d, J=14.0 Hz, 1H), 4.96 (d, J=14.5 Hz, 1H), 4.60 (d, J=14.5 Hz, 1H), 4.15-4.10 (m, 2H), 4.08-4.05 (m, 2H), 3.52 (s, 3H), 3.43-3.39 (m, 2H), 3.14-3.11 (m, 2H), 3.04-2.93 (m, 2H), 2.89-2.86 (m, 2H), 2.82-2.72 (m, 5H), 2.17 (t, J=7.0 Hz, 2H), 2.05-2.02 (m, 2H), 1.96-1.91 (m, 8H), 1.79-1.76 (m, 3H), 1.68-1.63 (m, 3H), 1.53-1.41 (m, 6H), 1.37 (d, J=4.0 Hz, 12H). MS (ESI)⁺ m/z 732.8 ([M2H]²⁺, 100%)

Lissamine™-$C_6$DAA1106 (LissDAA)

A mixture of lissamine™ rhodamine B sulphonyl chloride (10 mg, 17 μmol), conjugable DAA1106 (10 mg, 20 μmol) and tri-ethylamine (15 μL) in dichloromethane (1.6 mL) was stirred under argon at room temperature for 1 hour. The reaction solution was concentrated by rotary evaporation and the crude product was purified through column chromatography (silica gel) using a 19:1 dichloromethane:methanol solution to yield LissDAA as pink solid. (Isomer I, 5.7 mg, 32%; Isomer II, 4.7 mg, 27%). 1H NMR 400 MHz (CDCl3) Isomer J: δ 8.84 (s, 1H), 7.98 (d, J=7.6 Hz, 1H), 7.30-7.24 (m, 3H), 7.19 (d, J=7.6 Hz, 1H), 7.08 (t, J=7.2 Hz, 1H), 6.93-6.90 (m, 2H), 6.78 (t, J=8.8 Hz, 3H), 6.70 (dd, J=8.4, 2.0 Hz, 1H), 6.66-6.63 (m, 3H), 6.37 (d, J=8.4 Hz, 1H), 6.19 (s, 1H), 5.61 (t, J=5.2 Hz, 1H), 4.78 (d, J=6.4 Hz, 1H), 3.59 (s, 3H), 3.56-3.45 (m, 7H), 3.10 (q, J=6.4 Hz, 2H), 3.02-2.96 (m, 1H), 2.87-2.81 (m, 1H), 2.01 (s, 2H), 1.72-1.50 (m, 12H), 1.44-1.37 (m, 4H), 1.21 (t, J=6.8 Hz, 3H). Isomer II: δ 8.72 (s, 1H), 8.36 (d, J=7.2 Hz, 1H), 7.27-7.18 (m, 5H), 7.08 (t, J=7.6 Hz, 1H), 6.95-6.89 (m, 2H), 6.87-6.85 (m, 3H), 6.79-6.76 (m, 1H), 6.71 (d, J=2.4 Hz, 2H), 6.65 (d, J=8.0 Hz, 2H), 6.20 (d, J=2.8 Hz, 1H), 6.05-6.00 (m, 1H), 4.77 (s, 2H), 3.62-3.56 (m, 10H), 3.50-3.45 (m, 1H), 3.32-3.27 (m, 1H), 3.02-2.96 (m, 1H), 2.96-2.91 (m, 3H), 2.85-2.79 (m, 2H), 1.95 (s, 3H), 1.52-1.42 (m, 4H), 1.32 (t, J=7.2 Hz, 12H), 1.22-1.19 (m, 3H), 1.15-1.11 (m, 3H). MS (ESI): 1020.4 Da [M+Na]$^+$. Rf 0.39 (Isomer I), 0.32 (Isomer II) (6% methanol in dichloromethane).

Spectroscopic Characterization

Upon preparing NIRDAA and LissDAA, absorption and emission spectra were obtained at room temperature with a Shimadzu 1700 UV-vis spectrophotometer and ISS PCI spectrofluorometer respectively. NIRDAA was found to have an absorption maximum at 778 nm and fluorescence maximum at 800 nm in methanol. The two isomers of LissDAA have similar absorption maximum (isomer I at 561 nm and isomer II at 563 nm) and same fluorescence maximum at 583 nm.

Binding Studies

PBR protein was harvested from MA-10 cells and stocked in PBS at 10 mg/mL. The stock solution was diluted to 30 μg/100 L for the binding study. [$^3$H]PK11195 was used as radioligand and the specific activity of the stock solution was 73.6 Ci/mmole (~11.8 μM). A diluted solution of 15 nM in PBS was prepared before use. For each of the molecules tested (NIRDAA, LissDAA and $C_{3-9}$DAA1106 amide), eight concentrations of solutions from $3 \times 10^{-4}$ M to $3 \times 10^{-11}$ M in PBS buffer were prepared. 30 test tubes were used for the study of each molecule. 3 of them were used for total binding (100 μL 15 nM [$^3$H]PK11195+100 μL PBS buffer+100 μL 30 μg/100 μL PBR protein), 3 test tubes were for non-specific binding (100 μL 15 nM [$^3$H]PK11195+100 μL 15 μM PK11195+100 μL 30 μg/100 μL PBR protein) and the other 24 were triplicates for each doses of competitor ligand (100 μL 15 nM [$^3$H]PK11195+100 μL competitor solution+100 μL 30 μg/100 μL PBR protein). All test tubes were vortexed and then incubated at 4° C. for 90 minutes. Reactions were stopped by filtration on FG/B filters using the Brandel binding apparatus through Whatman GF/B filters (Brandel, Gaithersburg, Md.). The filters (24 positions each) were preincubated in PBS/H$_2$O containing 0.05% PEI for 20-30 minutes before filtration. The filters were then washed 5 times with PBS, put in scintillation vials, vortexed in scintillation fluid and counted. The IC50 and Ki (equilibrium dissociation constant) values were calculated using the PRISM program package Cell Imaging C6 glioma cells were cultured in Dulbecco's modified Eagle medium (DMEM)-F12 medium (Gibco/Invitrogen) supplemented with 0.1% gentamicin sulfate (Biowhittaker). MDA-MB-231 human mammary adenocarcinoma breast cancer cells cells were cultured in closed cap flasks, with 90% Leibovitz's L-15 medium, supplemented with 2 mM L-glutamine and 10% fetal bovine serum. MDA-MB-231 or C6 cells in MaTek dishes were incubated with 1 μM NIRDAA and 1 μM LissDAA in culture media for 30 minutes. 1 nM MitoTracker Green was then added to the cell plate and incubated for another 10 minutes. Cells were rinsed and re-incubated with saline before imaging on a Nikon epifluorescence microscope equipped with Hamamatsu C4742-98 camera, Nikon Plan Apo 60×/1.40 oil objective, a mercury lamp, an ICG filter set and a Fitc filter set.

Apoptosis Study Using Etoposide and EtoposideDAA 50,000 MDA-MB-231 human breast tumor (high PBR expressing) or human Jurkat T lymphocyte cells (low PBR expressing) cells /well were added to 96 well plates and incubated under standard tissue culture conditions (37° C., 5% CO$_2$) for 24 hours. Etoposide-C$_6$DAA1106 or etoposide were added at concentrations ranging from 100 μM to 100 pM. After three days, CellTiter-Glo luminescent cell viability assay (Promega) was added. The plates were incubated for an additional one hour and the fluorescence was counted under Xenogen IVIS imaging system. Three wells were used for control which had cells treated with viability assay without drug. Blank sampless did not have cells or drug, but had viability assay. Medium samples had cells only, without drug or viability assay.

Cytotoxicity comparison between etoposide-DAA and etoposide is shown in the above table. None of control, blank or medium samples gave any significant signal. Jurkat cells began to respond to etoposide at $10^{-6}$ M, and they were effectively responding at $10^{-5}$ M. However, Jurkat cells effectively respond to etoposide-C$_6$DAA1106 at $10^{-4}$ M. This indicates that etoposide-C$_6$DAA1106 has less toxicity to normal cells than etoposide. MDA-MB-231 cells were beginning to respond to etoposide and DAA-etoposide at $10^{-4}$ M. This shows that etoposideDAA and etoposide have similar efficiency in killing high PBR expressing cancer cells

REFERENCES

Throughout this application, various publications are referenced. All such publications, specifically including the publications listed below, are incorporated herein by reference in their entirety.

Manning H C, Goebel, T. S. Thompson, R. C., and Bornhop, D. J. A PBR Targeted Molecular Imaging Agent for Cellular-Scale Bi-modal Imaging. Bioconjugate Chemistry 2003; Bioconjugate Chem 2004, 15, 1488-1495.

Broaddus W C, Bennett J P, Jr., Department of Neurosurgery UoVHSCC. Peripheral-type benzodiazepine receptors in human glioblastomas: pharmacologic characterization and photoaffinity labeling of ligand recognition site. Brain research. 1990; 518 (1-2):199-208.

Zhang M R, Maeda J, Furutsuka K, Yoshida Y, Ogawa M, Suhara T, et al. [F-18]FMDAA1106 and [F-18]FEDAA1106: Two positron-emitter labeled ligands for peripheral benzodiazepine receptor (PBR). Bioorganic & Medicinal Chemistry Letters 2003; 13:201-204.

Kozikowski A P, Kotoula M, Ma D, Boujrad N, Tueckmantel W, Papadopoulos V. Synthesis and Biology of a 7-Nitro-2,1,3-benzoxadiazol-4-yl Derivative of 2-Phenylindole-3-acetamide: A Fluorescent Probe for the Peripheral-Type Benzodiazepine Receptor. Journal of Medicinal Chemistry 1997; 40:2435-2439.

Starosta-Rubinstein S, Ciliax B, Penney J, McKeever P, Young A. Imaging of a glioma using peripheral benzodiazepine receptor ligands. proceedings of the national academy of sciences of the United States of America 1987; 84:891-5.

Black K L, Ikezaki K, Toga A W. Imaging of Brain-Tumors Using Peripheral Benzodiazepine Receptor Ligands. Journal of Neurosurgery 1989; 71:113-118.

Sutter A P, Maaser K, Hèopfner M, Barthel B, Grabowski P, Faiss S, et al. Specific ligands of the peripheral benzodiazepine receptor induce apoptosis and cell cycle arrest in human esophageal cancer cells. International journal of cancer. Journal international du cancer. 2002; 102(4):318-27.

Jakubikova J, Duraj J, Hunakova L, Chorvath B, Sedlak J. PK11195, an isoquinoline carboxamide ligand of the mitochondrial benzodiazepine receptor, increased drug uptake and facilitated drug-induced apoptosis in human multidrug-resistant leukemia cells in vitro. Neoplasma 2002; 49:231-236.

Okaro A C, Fennell D A, Corbo M, Davidson B R, Cotter F E. Pk11195, a mitochondrial benzodiazepine receptor antagonist, reduces apoptosis threshold in Bcl-X-L and Mcl-1 expressing human cholangiocarcinoma cells. Gut 2002; 51:556-561.

Okaro M C, Fennel D A, Corbo M, Cotter F E, Davidson B R, Winslet M C. In vivo reversal of apoptosis resistance by the mitochondrial benzodiazepine receptor antagonist, PK11195 in cholangiocarcinoma cells. Gut 2000; 46:A47-A47.

Okaro M C, Fennell D A, Cotter F E, Davidson B R. Pk11195, a mitochondrial benzodiazepine receptor antagonist radiosensitizes bcl-x(L) and mcl-1 expressing cholangiocarcinoma to apoptosis. British Journal of Cancer 2000; 83:22-22.

Maaser K, Hèopfner M, Jansen A, Weisinger G, Gavish M, Kozikowski A P, et al. Specific ligands of the peripheral benzodiazepine receptor induce apoptosis and cell cycle arrest in human colorectal cancer cells. British journal of cancer. 2001; 85(11): 1771-80.

Fennell D A, Corbo M, Pallaska A, Cotter F E. Bcl-2 resistant mitochondrial toxicity mediated by the isoquinoline carboxamide PK11195 involves de novo generation of reactive oxygen species. British Journal of Cancer 2001; 84: 1397-1404.

Ntziachristos V, Chance B. Probing physiology and molecular function using optical imaging: applications to breast cancer. Breast Cancer Research 2001; 3:41-46.

Licha K, Riefke B, Ntziachristos V, Becker A, Chance B, Semmler W. Hydrophilic cyanine dyes as contrast agents for near-infrared tumor imaging: Synthesis, photophysical properties and spectroscopic in vivo characterization. Photochemistry and Photobiology 2000; 72:392-398.

Hawrysz D J, Sevick-Muraca E M. Developments toward diagnostic breast cancer imaging using near-infrared optical measurements and fluorescent contrast agents. Neoplasia 2000; 2:388-417.

Weissleder R, Mahmood U. Molecular imaging. Radiology 2001; 219:316-333.

Gaietta G, Deerinck T J, Adams S R, Bouwer J, Tour O, Laird D W, et al. Multicolor and electron microscopic imaging of connexin trafficking. Science 2002; 296:503-507.

Louie A Y, Huber M M, Ahrens E T, Rothbacher U, Moats R, Jacobs R E, et al. In vivo visualization of gene expression using magnetic resonance imaging. Nature Biotechnology 2000; 18:321-325.

Wolfe H R, Mendizabal M, Lleong E, Cuthbertson A, Desai V, Pullan S, et al. In vivo imaging of human colon cancer xenografts in immunodeficient mice using a guanylyl cyclase C-specific ligand. Journal of Nuclear Medicine 2002; 43:392-399.

Lemieux G A, Yarema K J, Jacobs C L, Bertozzi C R. Exploiting differences in sialoside expression for selective targeting of MRI contrast reagents. Journal of the American Chemical Society 1999; 121:4278-4279.

Casellas P, Galiegue S, Basile A S. Peripheral benzodiazepine receptors and mitochondrial function. Neurochemistry International 2002; 40:475-486.

Hardwick M, Fertikh D, Culty M, Li H, Vidic B, Papadopoulos V. Peripheral-type benzodiazepine receptor (PBR) in human breast cancer: Correlation of breast cancer cell aggressive phenotype with PBR expression, nuclear localization, and PBR-mediated cell proliferation and nuclear transport of cholesterol. Cancer Research 1999; 59:831-842.

Papadopoulos V. Peripheral-Type Benzodiazepine Diazepam Binding Inhibitor Receptor—Biological Role in Steroidogenic Cell-Function. Endocrine Reviews 1993; 14:222-240.

Alho H, Varga V, Krueger K E. Expression of Mitochondrial Benzodiazepine Receptor and Its Putative Endogenous Ligand in Cultured Primary Astrocytes and C-6 Cells—Relation to Cell-Growth. Cell Growth & Differentiation 1994; 5:1005-1014.

Diorio D, Welner S A, Butterworth R F, Meaney M J, Suranyicadotte B E. Peripheral Benzodiazepine Binding-Sites in Alzheimers-Disease Frontal and Temporal Cortex. Neurobiology of Aging 1991; 12:255-258.

Messmer K, Reynolds G P. Increased peripheral benzodiazepine binding sites in the brain of patients with Huntington's disease. Neuroscience Letters 1998; 241:53-56.

Vowinckel E, Reutens D, Becher B, Verge G, Evans A, Owens T, et al. PK11195 binding to the peripheral benzodiazepine receptor as a marker of microglia activation in multiple sclerosis and experimental autoimmune encephalomyelitis. Journal of Neuroscience Research 1997; 50:345-353.

Benavides J, Cornu P, Dennis T, Dubois A, Hauw J J, Mackenzie E T, et al. Imaging of Human-Brain Lesions with an Omega-3 Site Radioligand. Annals of Neurology 1988; 24:708-712.

Cornu P, Benavides J, Scatton B, Hauw J J, Philippon J. Increase in Omega-3 (Peripheral-Type Benzodiazepine) Binding-Site Densities in Different Types of Human Brain-Tumors—a Quantitative Autoradiography Study. Acta Neurochirurgica 1992; 119:146-152.

Shavaleev N M, Pope S J A, Bell Z R, Faulkner S, Ward M D. Visible-light sensitisation of near-infrared luminescence from Yb(III), Nd(III) and Er(III) complexes of 3,6-bis(2-pyridyl)tetrazine. Dalton Transactions 2003:808-814.

Werts M H V, Verhoeven J W, Hofstraat J W. Efficient visible light sensitisation of water-soluble near-infrared luminescent lanthanide complexes. Journal of the Chemical Society-Perkin Transactions 2 2000:433-439.

Werts M H V, Hofstraat J W, Geurts F A J, Verhoeven J W. Fluorescein and eosin as sensitizing chromophores in near-infrared luminescent ytterbium(III), neodymium(III) and erbium(III) chelates. Chemical Physics Letters 1997; 276: 196-201.

Faulkner S, Pope S J A. Lanthanide-sensitized lanthanide luminescence: Terbium-sensitized ytterbium luminescence in a trinuclear complex. Journal of the American Chemical Society 2003; 125:10526-10527.

Bromiley A, Welch A, Chilcott F, Waikar S, McCallum S, Dodd M, et al. Attenuation correction in PET using consistency conditions and a three-dimensional template. Ieee Transactions on Nuclear Science 2001; 48:1371-1377.

Couper G W, McAteer D, Wallis R, Welch A, Norton M, Park K G M. Quantification of FDG-PET scans in patients with oesophageal and gastric cancer. A study of 40 patients. British Journal of Surgery 2002; 89:64-64.

Couper G W, Wallis F, Welch A, Sharp P F, Park K G M, Cassidy J. The role of FDG-PET in the early detection of response of colorectal liver metastases to chemotherapy. Gut 2002; 50:A107-A107.

Dehdashti F, Flanagan F L, Mortimer J E, Katzenellenbogen J A, Welch M J, Siegel B A. Positron emission tomographic assessment of "metabolic flare" to predict response of metastatic breast cancer to antiestrogen therapy. European Journal of Nuclear Medicine 1999; 26:51-56.

Oyama N, Kim J, Jones L A, Mercer N M, Engelbach J A, Sharp T L, et al. MicroPET assessment of androgenic control of glucose and acetate uptake in the rat prostate and a prostate cancer tumor model. Nuclear Medicine and Biology 2002; 29:783-790.

Oyama N, Miller T R, Dehdashti F, Siegel B A, Fischer K C, Michalski J M, et al. C-11-acetate PET imaging of prostate cancer: Detection of recurrent disease at PSA relapse. Journal of Nuclear Medicine 2003; 44:549-555.

Smith I C, Welch A, Chilcott F, Soloviev D, Waikar S, Hutcheon A W, et al. F-18-FDG PET may predict the pathological response of breast cancer to primary chemotherapy. Journal of Nuclear Medicine 1999; 40:137 p-137 p.

Smith I C, Welch A E, Hutcheon A W, Miller I D, Payne S, Chilcott F, et al. Positron emission tomography using [F-18]-fluorodeoxy-D-glucose to predict the pathologic response of breast cancer to primary chemotherapy. Journal of Clinical Oncology 2000; 18:1676-1688.

Manning H C, Goebel T, Marx J N, Bornhop D J. Facile, efficient conjugation of a trifunctional lanthanide chelate to a peripheral benzodiazepine receptor ligand. Organic Letters 2002; 4:1075-1078.

Zhang M, Zhang Z H, Blessington D, Li H, Busch T M, Madrak V, et al. Pyropheophorbide 2-deoxyglucosamide: A new photosensitizer targeting glucose transporters. Bioconjugate Chemistry 2003; 14:709-714.

Decaudin, D.; Castedo, M.; Nemati, F.; Beurdeley-Thomas, A.; De Pinieux, G.; Caron, A.; Pouillart, P.; Wijdenes, J.; Rouillard, D.; Kroemer, G.; Poupon, M. F. Cancer Res 2002, 62, 1388-1393.

Romeo, E.; Auta, J.; Kozikowski, A. P.; Ma, D.; Papadopoulos, V.; Puia, G.; Costa, E.; Guidotti, A. J Pharmacol Exp Ther 1992, 262, 971-978.

Kozikowski, A. P.; Ma, D.; Brewer, J.; Sun, S.; Costa, E.; Romeo, E.; Guidotti, A. Journal of Medicinal Chemistry 1993, 36, 2908-2920.

Culty, M.; Silver, P.; Nakazato, A.; Gazouli, M.; Li, H.; Muramatsu, M.; Okuyama, S.; Papadopoulos, V. Drug Develop Res 2001, 52, 475-484.

Maeda, J.; Suhara, T.; Zhang, M. R.; Okauchi, T.; Yasuno, F.; Ikoma, Y.; Inaji, M.; Nagai, Y.; Takano, A.; Obayashi, S.; Suzuki, K. Synapse 2004, 52, 283-291.

Chaki, S.; Funakoshi, T.; Yoshikawa, R.; Okuyama, S.; Okubo, T.; Nakazato, A.; Nagamine, M.; Tomisawa, K. Eur J Pharmacol 1999, 371, 197-204.

Manning, H. C.; Goebel, T.; Marx, J. N.; Bornhop, D. J. Org Lett 2002, 4, 1075-1078.

Manning, H. C.; Smith, S. M.; Sexton, M.; Haviland, S.; Bai, M. F.; Cederquist, K.; Stella, N.; Bornhop, D. J. Bioconjugate Chem 2006, 17, 735-740.

Okubo, T.; Yoshikawa, R.; Chaki, S.; Okuyama, S.; Nakazato, A. Bioorgan Med Chem 2004, 12, 423-438.

Zhang, M. R.; Kida, T.; Noguchi, J.; Furutsuka, K.; Maeda, J.; Suhara, T.; Suzuki, K. Nucl Med Biol 2003, 30, 513-519.

Hasinoff B B, Chee G L, Day B W, Avor K S, Barnabe N, Thampatty P, et al. Synthesis and biological activity of a photoaffinity etoposide probe. Bioorganic & Medicinal Chemistry 2001; 9:1765-1771.

Ishiguro K, Taft W C, Delorenzo R J, Sartorelli A C. The Role of Benzodiazepine Receptors in the Induction of Differentiation of H1-60 Leukemia-Cells by Benzodiazepines and Purines. Journal of Cellular Physiology 1987; 131:226-234.

Alexander B E E, Roller E, Klotz U. Characterization of Peripheral-Type Benzodiazepine Binding-Sites on Human-Lymphocytes and Lymphoma Cell-Lines and Their Role in Cell-Growth. Biochemical Pharmacology 1992; 44:269-274.

Culty M, Silver P, Nakazato A, Gazouli M, Li H, Muramatsu M, et al. Peripheral benzodiazepine receptor binding properties and effects on steroid synthesis of two new phenoxyphenyl-acetamide derivatives, DAA1097 and DAA1106. Drug Development Research 2001; 52:475-484.

Okaro A C, Fennell D A, Corbo M, Davidson B R, Cotter F E. Pk11195, a mitochondrial benzodiazepine receptor antagonist, reduces apoptosis threshold in Bcl-X-L and Mcl-1 expressing human cholangiocarcinoma cells. Gut 2002; 51:556-561.

Hirsch T, Decaudin D, Susin S A, Marchetti P, Larochette N, Resche-Rigon M, et al. PK11195, a ligand of the mitochondrial benzodiazepine receptor, facilitates the induction of apoptosis and reverses Bcl-2-mediated cytoprotection. Experimental Cell Research 1998; 241:426-434.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the Specification and Example be considered as exemplary only, and not intended to limit the scope and spirit of the invention.

Unless otherwise indicated, all numbers expressing quantities of ingredients, properties such as reaction conditions, and so forth used in the Specification and Claims are to be understood as being modified in all instances by the term "about." Accordingly, unless indicated to the contrary, the numerical parameters set forth in the Specification and Claims are approximations that may vary depending upon the desired properties sought to be determined by the present invention.

Notwithstanding that the numerical ranges and parameters setting forth the broad scope of the invention are approximations, the numerical values set forth in the experimental or example sections are reported as precisely as possible. Any numerical value, however, inherently contain certain errors necessarily resulting from the standard deviation found in their respective testing measurements.

We claim:

1. A compound of the following formula:

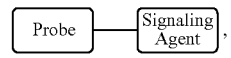

wherein the probe is selected from a compound of the following formula:

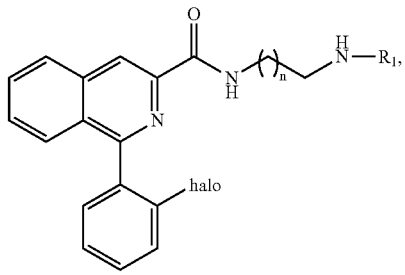

-continued
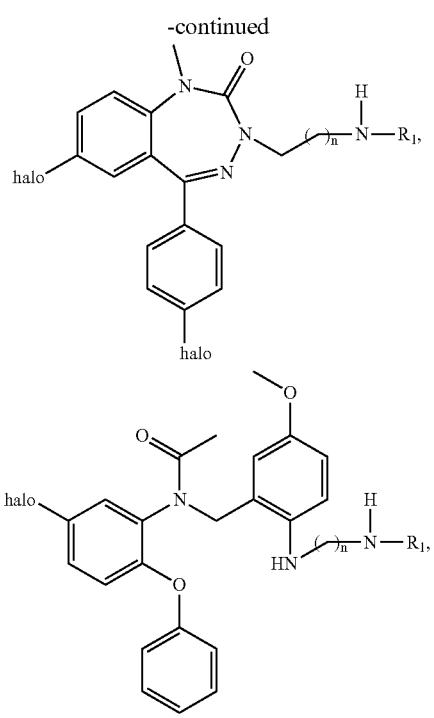
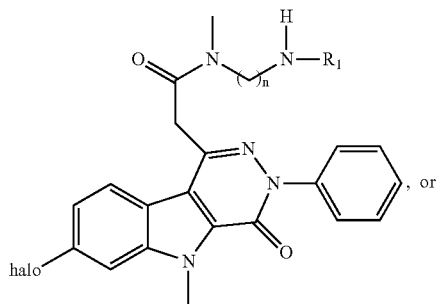
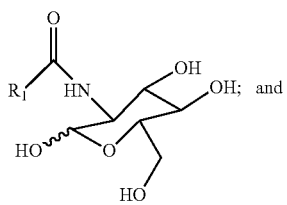
, or
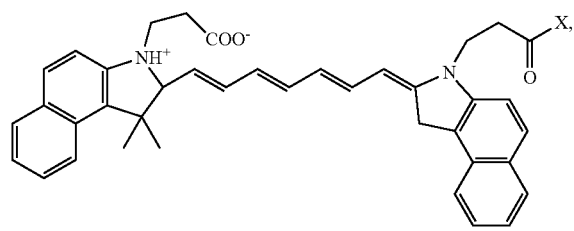
wherein the signaling moiety is selected from the following formula:
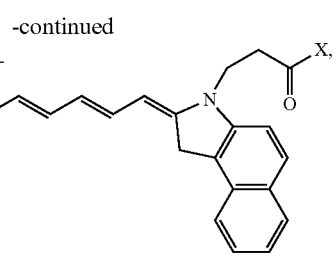
Cypate: X = Conjugation Site
-continued
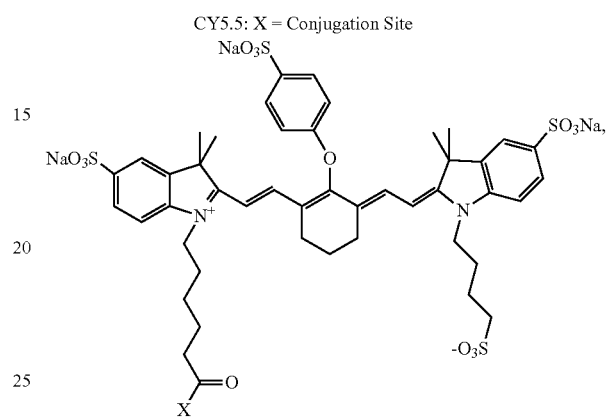
CY5.5: X = Conjugation Site
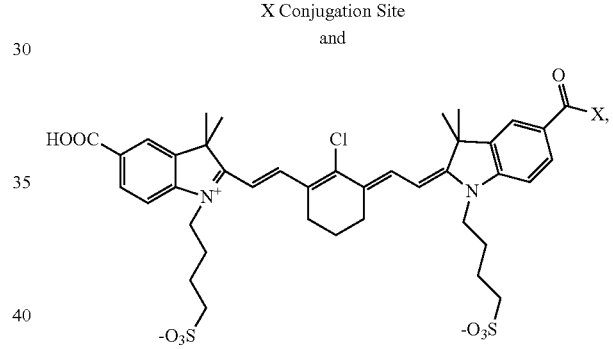
LI-COR 800CW:
X Conjugation Site
and
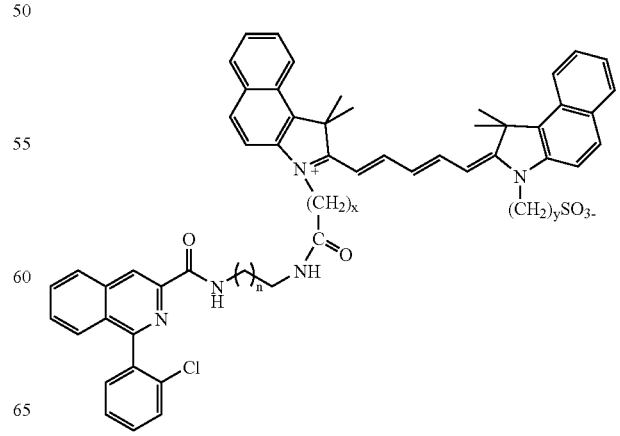
NIR-820: X Conjugation Site
wherein n is an integer from 1 to 10, halo is halogen, and $R_1$—X is the conjugation site.
2. A compound of claim 1, of the following formula:

or a stereoisomer or conjugable analog thereof, wherein n, x and y are integers from 1 to 10.

3. A compound of claim 1, of the following formula:

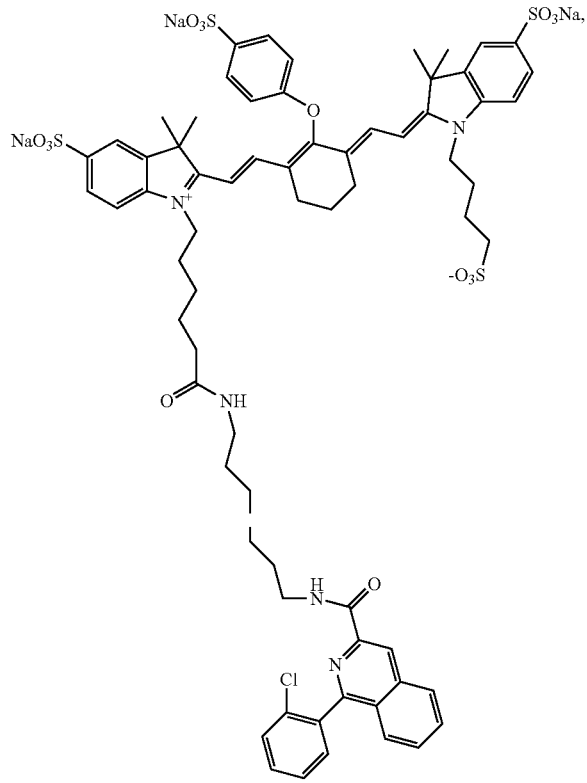

or a stereoisomer or conjugable analog thereof.

4. A compound of the following formula:

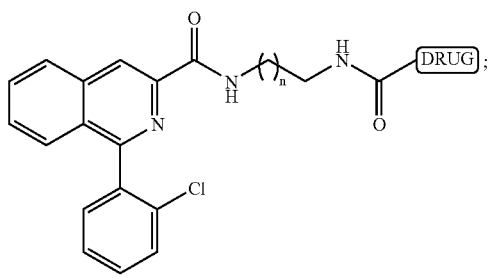

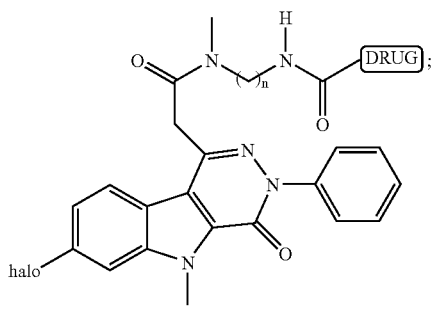

-continued

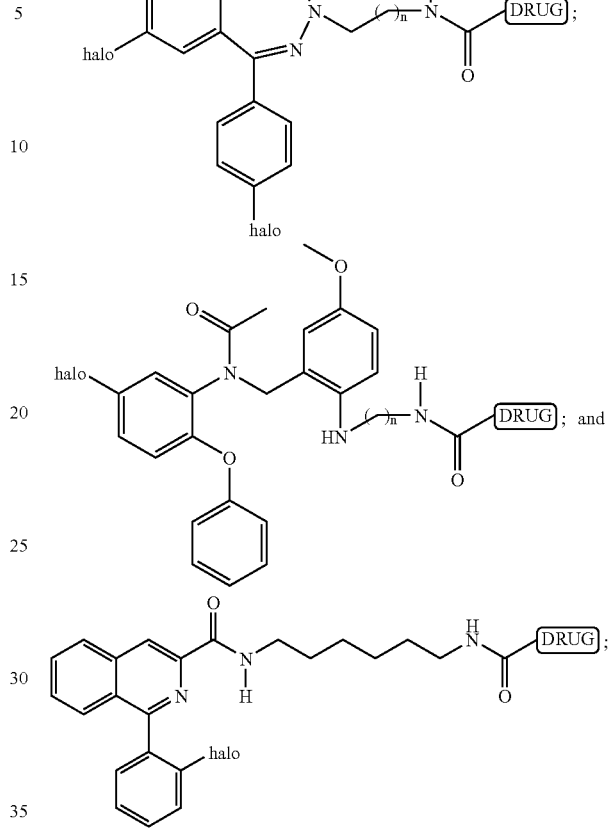

or a stereoisomer or conjugable analog thereof, wherein n is an integer from 1 to 10, "halo" is halogen and "drug" is a chemotherapeutic agent.

5. The compound of claim 4, wherein the chemotherapeutic agent is a topoisomerase inhibitor.

6. The compound of claim 5, wherein the topoisomerase inhibitor is adriamycin, amsacrine, camptothecin, daunorubicin, dactinomycin, doxorubicin, eniposide, epirubicin, etoposide, idarubicin, mitoxantrone, teniposide, or topotecan.

7. The compound of claim 5, wherein the topoisomerase inhibitor is etoposide.

8. A method of delivering a therapeutic drug to a target, comprising:

(a) administering to said sample a probe having an affinity for a target, the probe comprising at least one of a ligand/therapeutic drug combination, or conjugable form of a ligand/therapeutic drug combination;
wherein the ligand is a compound of the following formula:

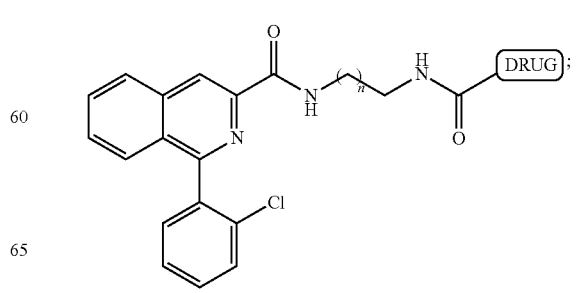

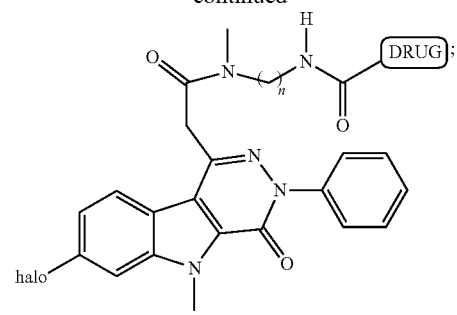
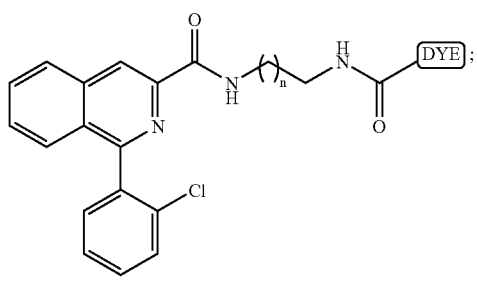
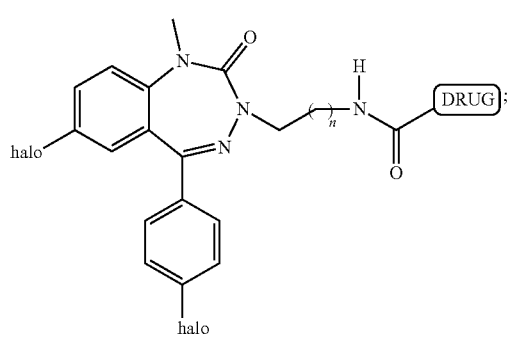
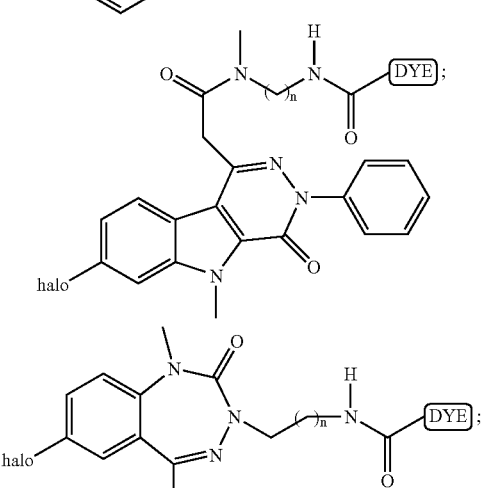
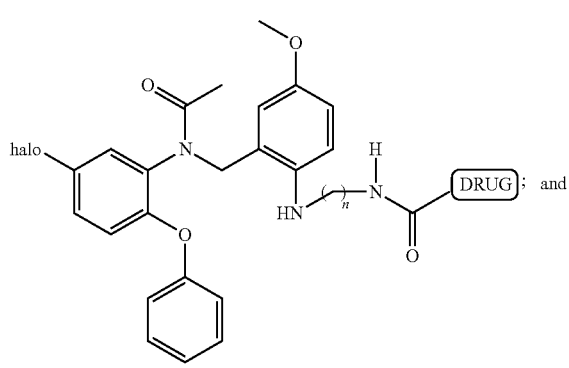
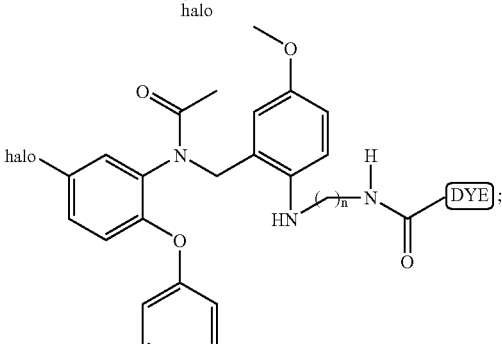
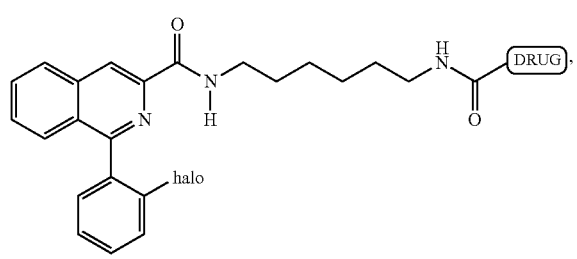
or a stereoisomer or conjugable analog thereof, wherein n is an integer from 1 to 10, "halo" is halogen and "drug" is a chemotherapeutic agent.
9. A method of imaging a molecular event, comprising:
(a) administering a probe having an affinity for a target, the probe comprising a compound of the following formulae:
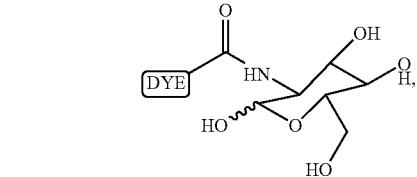
wherein n is an integer from 1 to 10, and analogs thereof; and wherein the dye is selected from the following formula:
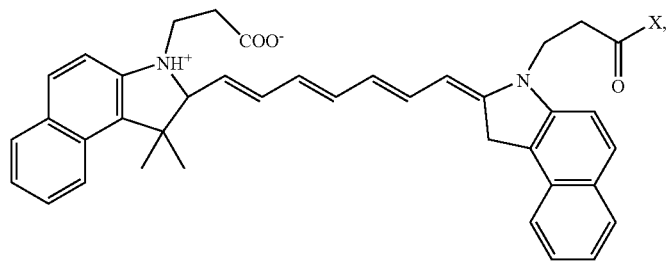
Cypate: X = Conjugation Site
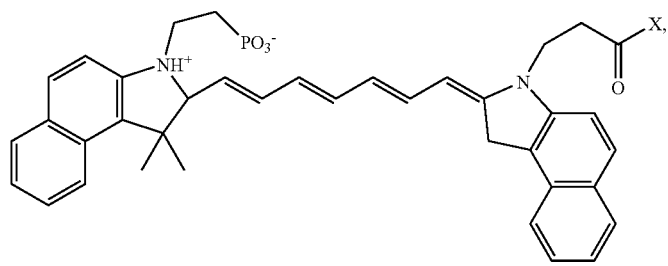
CY5.5: X = Conjugation Site
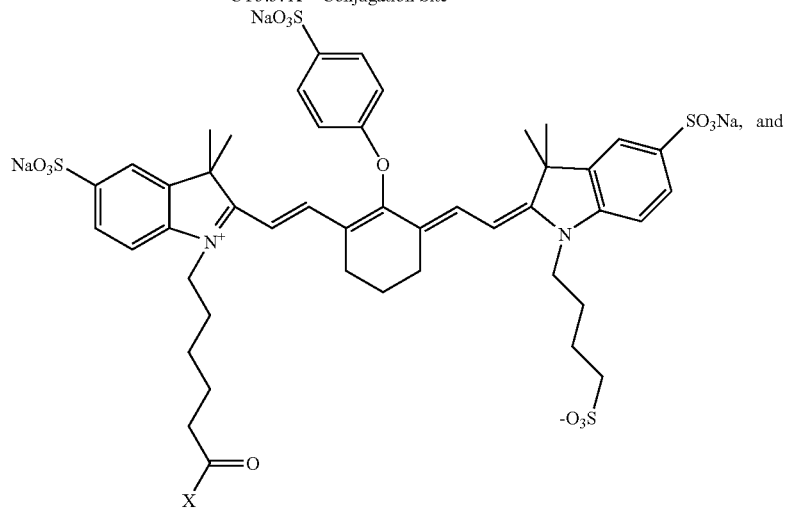
LI-COR 800CW: X Conjugation Site
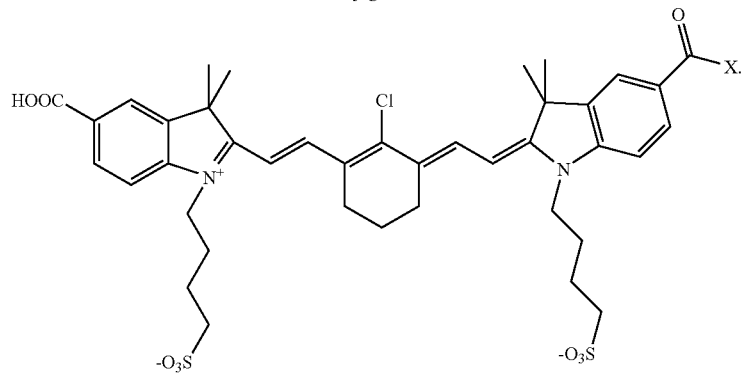
NIR-820: X Conjugation Site

10. A method of treating breast cancer and unwanted proliferation of cells associated therewith in a patient, comprising administering to said patient a compound of the following formula:

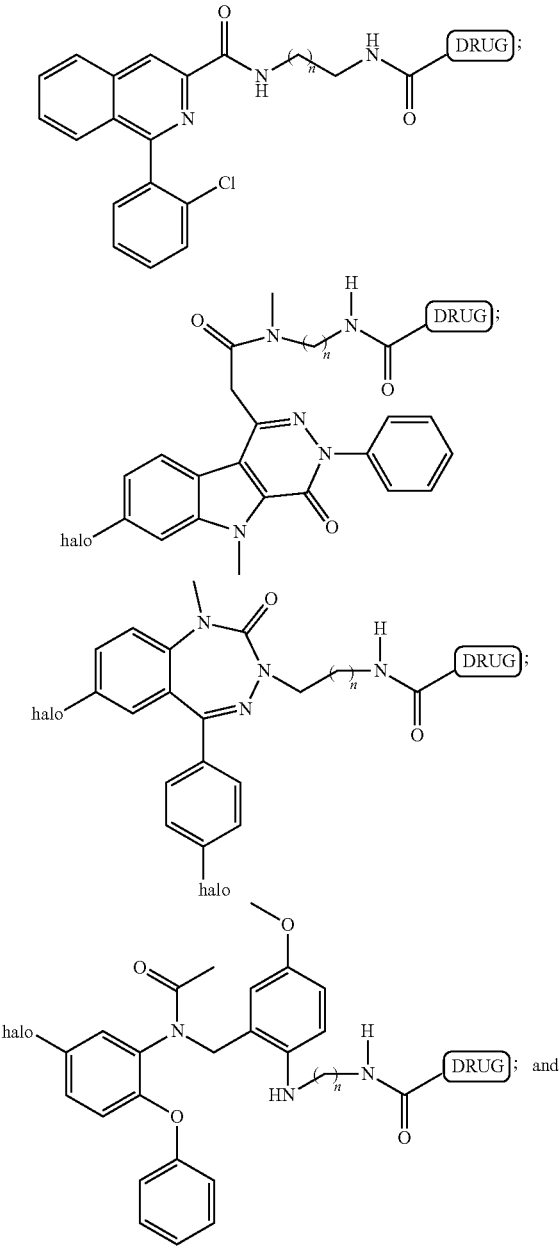

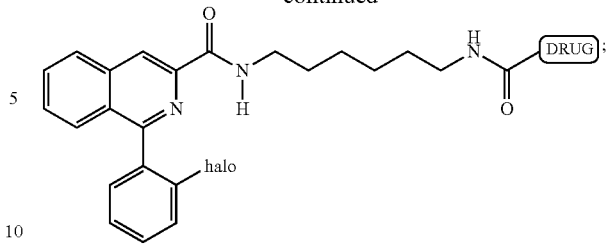

and stereoisomers and conjugable analogs thereof, wherein n is an integer from 1 to 10, "halo" is halogen and "drug" is a chemotherapeutic agent.

11. The method of claim 10, wherein the drug is a topoisomerase inhibitor.

12. The method of claim 11, wherein the topoisomerase inhibitor is selected from the group consisting of adriamycin, amsacrine, camptothecin, daunorubicin, dactinomycin, doxorubicin, eniposide, epirubicin, etoposide, idarubicin, mitoxantrone, teniposide, and topotecan.

13. The method of claim 10, wherein the drug is etoposide.

14. The method of claim 10, wherein the compound is of the following formula:

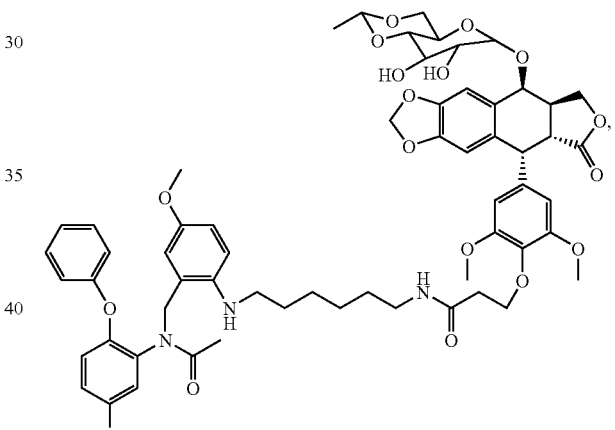

15. A pharmaceutical composition comprising a compound of claim 1, and a pharmaceutically acceptable carrier.

16. A pharmaceutical composition comprising a compound of claim 4, and a pharmaceutically acceptable carrier.

* * * * *